United States Patent
Kawamura et al.

(10) Patent No.: US 9,837,615 B2
(45) Date of Patent: Dec. 5, 2017

(54) NITROGEN-CONTAINING HETEROCYCLIC DERIVATIVE, ORGANIC ELECTROLUMINESCENCE ELEMENT MATERIAL USING SAME, AND ORGANIC ELECTROLUMINESCENCE ELEMENT AND ELECTRONIC DEVICE USING SAME

(71) Applicant: IDEMITSU KOSAN CO., LTD., Tokyo (JP)

(72) Inventors: Masahiro Kawamura, Chiba (JP); Yumiko Mizuki, Ichihara (JP); Hirokatsu Ito, Ichihara (JP); Tomoharu Hayama, Utsunomiya (JP); Tasuku Haketa, Ichihara (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 14/716,429

(22) Filed: May 19, 2015

(65) Prior Publication Data
US 2015/0255726 A1    Sep. 10, 2015

Related U.S. Application Data

(63) Continuation of application No. PCT/JP2014/064883, filed on Jun. 4, 2014.

(30) Foreign Application Priority Data

Jun. 4, 2013    (JP) .................................. 2013-117795

(51) Int. Cl.
*H01L 51/00* (2006.01)
*C09K 11/06* (2006.01)
(Continued)

(52) U.S. Cl.
CPC ........ *H01L 51/0054* (2013.01); *C07D 209/56* (2013.01); *C07D 209/80* (2013.01);
(Continued)

(58) Field of Classification Search
None
See application file for complete search history.

(56) References Cited

U.S. PATENT DOCUMENTS

2004/0247933 A1    12/2004  Thoms
2008/0122344 A1    5/2008   Shin et al.
(Continued)

FOREIGN PATENT DOCUMENTS

CN    103524398 A    1/2014
EP    2 871 686 A1   5/2015
(Continued)

OTHER PUBLICATIONS

Office Action dated Jul. 14, 2015, in Japanese Patent Application No. 2015-518686.
(Continued)

*Primary Examiner* — J. L. Yang
(74) *Attorney, Agent, or Firm* — Oblon, McClelland, Maier & Neustadt, L.L.P.

(57) ABSTRACT

A nitrogen-containing heterocyclic derivative in which an indole structure is fused to a benzophenanthrene ring is a novel material useful as a material for organic electroluminescence devices for the production of organic electroluminescence devices and electronic equipment.

21 Claims, 1 Drawing Sheet

(51) Int. Cl.
| | |
|---|---|
| *C07D 403/04* | (2006.01) |
| *C07D 209/56* | (2006.01) |
| *C07D 403/10* | (2006.01) |
| *C07D 209/80* | (2006.01) |
| *H01L 51/50* | (2006.01) |

(52) U.S. Cl.
CPC ......... *C07D 403/04* (2013.01); *C07D 403/10* (2013.01); *C09K 11/06* (2013.01); *H01L 51/0067* (2013.01); *H01L 51/0072* (2013.01); *H01L 51/0085* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/0059* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 2008/0124455 A1 | 5/2008 | Shin et al. |
| 2010/0096982 A1 | 4/2010 | Eum et al. |
| 2011/0084256 A1 | 4/2011 | Kim et al. |
| 2011/0108821 A1 | 5/2011 | Kaiser et al. |
| 2011/0114889 A1 | 5/2011 | Buesing et al. |
| 2011/0210318 A1 | 9/2011 | Bae et al. |
| 2012/0132899 A1 | 5/2012 | Kawamura et al. |
| 2012/0211735 A1 | 8/2012 | Imada et al. |
| 2012/0217485 A1 | 8/2012 | Lee et al. |
| 2013/0048975 A1 | 2/2013 | Hong et al. |
| 2014/0117326 A1 | 5/2014 | Lee et al. |
| 2015/0228905 A1 | 8/2015 | Buesing et al. |
| 2015/0255726 A1 | 9/2015 | Kawamura et al. |

FOREIGN PATENT DOCUMENTS

| | | |
|---|---|---|
| EP | 2 907 803 A1 | 8/2015 |
| JP | H11-149987 A | 6/1999 |
| JP | 2002-069044 A | 3/2002 |
| JP | 2004-142131 A | 5/2004 |
| JP | 2010-059158 A | 3/2010 |
| JP | 2011-079822 A | 4/2011 |
| JP | 2011-529614 A | 12/2011 |
| JP | 2014-045101 A | 3/2014 |
| JP | 2014-183315 A | 9/2014 |
| KR | 10-2012-0021203 | 3/2012 |
| KR | 10-2012-0095765 A | 8/2012 |
| KR | 10-2012-0104067 A | 9/2012 |
| KR | 10-1219492 | 1/2013 |
| KR | 10-2013-0016163 A | 2/2013 |
| KR | 10-2013-0080827 A | 7/2013 |
| KR | 10-2014-032823 A | 3/2014 |
| KR | 10-2014-0103391 A | 8/2014 |
| WO | WO 2010/114264 A2 | 10/2010 |
| WO | WO 2011/037429 A2 | 3/2011 |
| WO | WO 2011/139125 A2 | 11/2011 |
| WO | WO 2012/036482 A1 | 3/2012 |
| WO | WO 2012/050347 A1 | 4/2012 |
| WO | WO 2013/122364 A2 | 8/2013 |
| WO | WO 2014/014310 A1 | 1/2014 |
| WO | WO 2014/038867 A1 | 3/2014 |
| WO | WO 2014/054596 A1 | 4/2014 |
| WO | WO 2014/137104 A1 | 9/2014 |
| WO | WO 2014/157574 A1 | 10/2014 |
| WO | WO 2014/178434 A1 | 11/2014 |

OTHER PUBLICATIONS

Kimio Hirano et al., Gold(I)-Catalyzed Polycyclizations of Polyenyne-Type Anilines Based on Hydroamination and Consecutive Hydroarylation Cascade, Journal of Organic Chemistry, 2011, vol. 76, No. 21, pp. 9068-9080.

International Search Report dated Jul. 22, 2014, in PCT/JP2014/064883 filed Jun. 4, 2014.

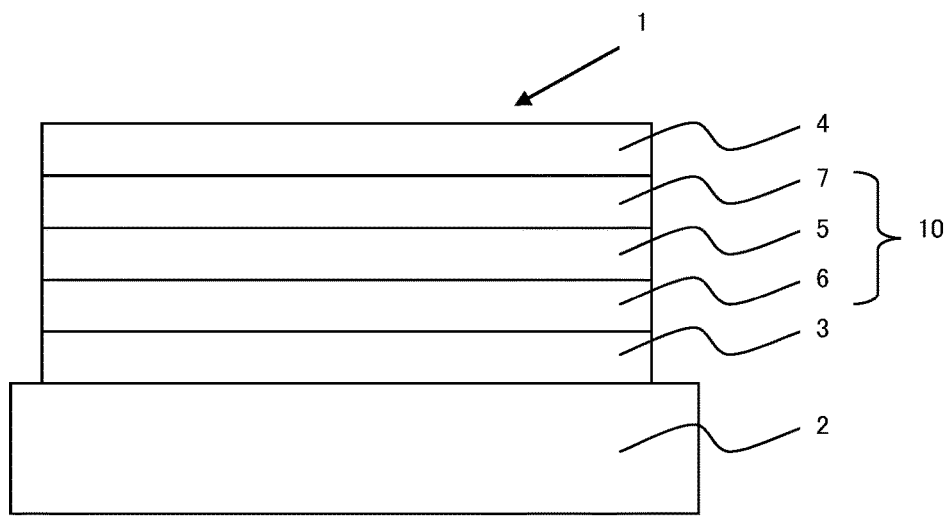

NITROGEN-CONTAINING HETEROCYCLIC DERIVATIVE, ORGANIC ELECTROLUMINESCENCE ELEMENT MATERIAL USING SAME, AND ORGANIC ELECTROLUMINESCENCE ELEMENT AND ELECTRONIC DEVICE USING SAME

CROSS-REFERENCE TO RELATED APPLICATIONS

The present application is a continuation application of International Application No. PCT/JP2014/064883, filed Jun. 4, 2014, which claims priority to Japanese Patent Application No. 2013-117795, filed Jun. 4, 2013. The contents of these applications are incorporated herein by reference in their entirety.

TECHNICAL FIELD

The present invention relates to nitrogen-containing heterocyclic derivatives, materials for organic electroluminescence devices comprising the derivative, organic electroluminescence devices comprising the derivative, and electronic equipment.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, blue colors has been made most actively, and the intensive research has been made to improve their properties.

PRIOR ART

Patent Documents

Patent Document 1: KR 10-2012-0021203A
Patent Document 2: WO 2011/037429

SUMMARY OF THE INVENTION

Problems to be Solved by the Invention

The present invention has been made to solve the above problems and an object of the invention is to provide a new material useful for organic EL devices.

Means for Solving the Problem

As a result of extensive research, the inventors have found that a nitrogen-containing heterocyclic derivative in which an indole structure is bonded to a benzophenanthrene ring is useful as a material for organic EL devices.

In an aspect of the present invention, the following (1) to (4) are provided:

(1) a nitrogen-containing heterocyclic derivative represented by formula (1):

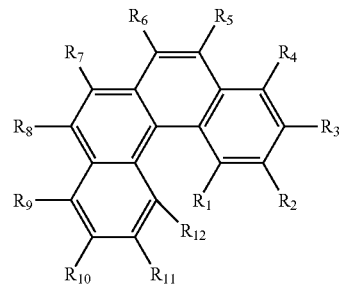

(1)

wherein each of $R_1$ to $R_{12}$ independently represents a hydrogen atom or a substituent group, and a pair of adjacent two groups selected from $R_1$ to $R_{12}$ may be bonded to each other to form a saturated or unsaturated divalent group which completes a ring, provided that at least one pair of the adjacent two groups selected from $R_1$ to $R_{12}$ are bonded to each other to form a ring structure represented by formula (a):

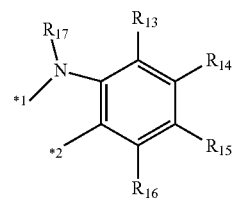

(a)

wherein each of $R_{13}$ to $R_{17}$ independently represents a hydrogen atom or a substituent group, a pair of adjacent two groups selected from $R_{13}$ to $R_{17}$ may be bonded to each other to form a saturated or unsaturated divalent group which completes a ring, and *1 and *2 are bonded to carbon atoms to which the at least one pair of the adjacent two groups selected from $R_1$ to $R_{12}$ are bonded;

(2) a material for organic electroluminescence devices comprising the nitrogen-containing heterocyclic derivative mentioned above;

(3) an organic electroluminescence device which comprises an organic thin film layer between a cathode and an anode, wherein the organic thin film layer comprises one or more layers and comprises a light emitting layer, and at least one layer of the organic thin film layer comprises the nitrogen-containing heterocyclic derivative mentioned above; and (4) an electronic equipment comprising the organic electroluminescence device mentioned above.

Effects of the Invention

The present invention provides a novel material useful as a material for organic EL devices and an organic EL device comprising the material.

BRIEF DESCRIPTION OF THE DRAWINGS

The FIG. 1s a schematic illustration showing an example of the structure of an organic electroluminescence device according to an embodiment of the invention.

MODE FOR CARRYING OUT THE INVENTION

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each of "XX" and "YY" represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each of "XX" and "YY" represents an integer of 1 or more.

The term of "unsubstituted group ZZ" referred to by "a substituted or unsubstituted group ZZ" used herein means the group ZZ wherein no hydrogen atom is substituted by a substituent.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

A substituted or unsubstituted carbazolyl group referred to herein includes the following carbazolyl groups:

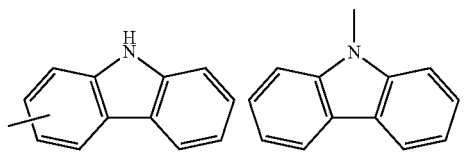

and a carbazolyl group substituted by an optional substituent mentioned below, and further includes, for example, the following substituted carbazolyl groups:

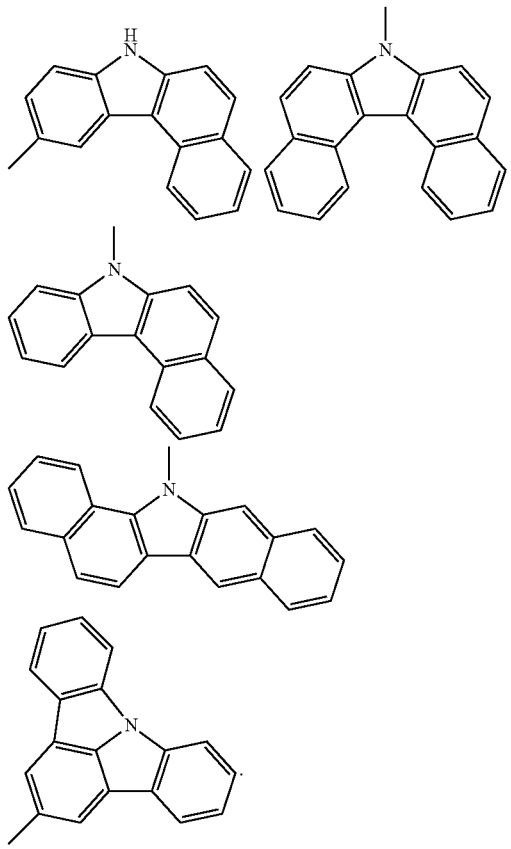

A substituted or unsubstituted dibenzofuranyl group and a substituted or unsubstituted dibenzothiophenyl group referred to herein include the following dibenzofuranyl group and the following dibenzothiophenyl group:

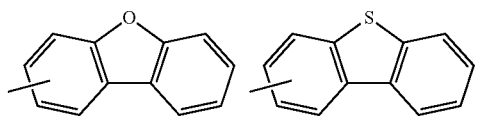

and a dibenzofuranyl group and a dibenzothiophenyl group each being substituted by an optional substituent mentioned below, and further includes, for example, the following substituted dibenzofuranyl groups and the following substituted dibenzothiophenyl groups:

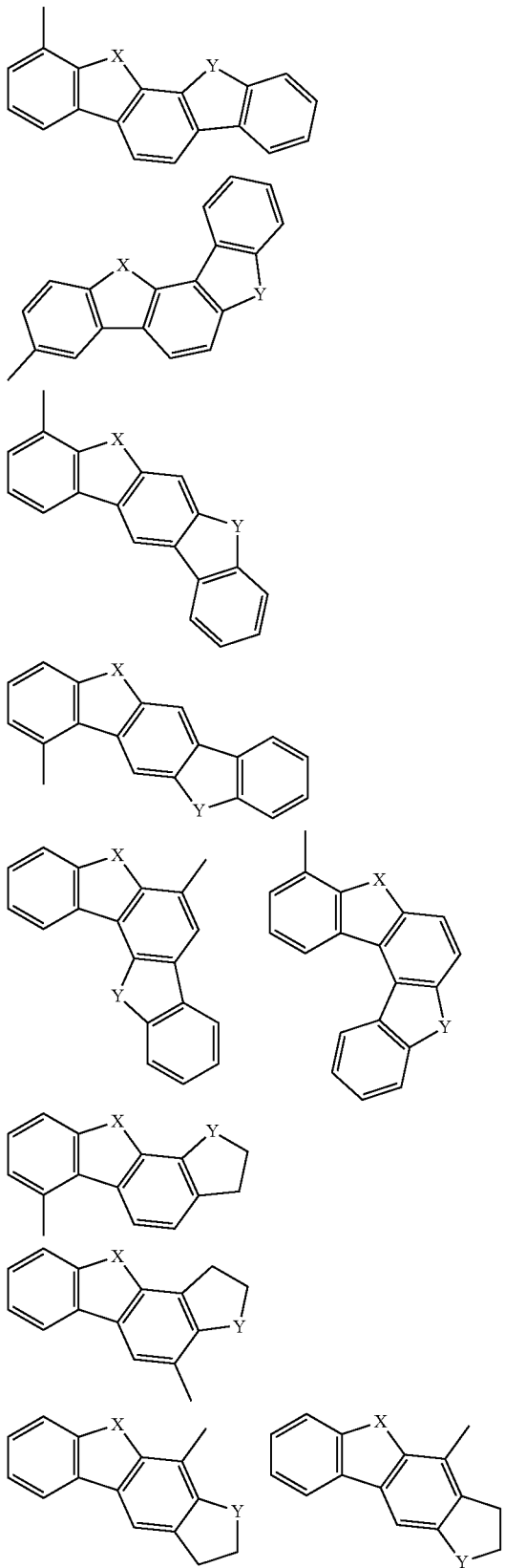

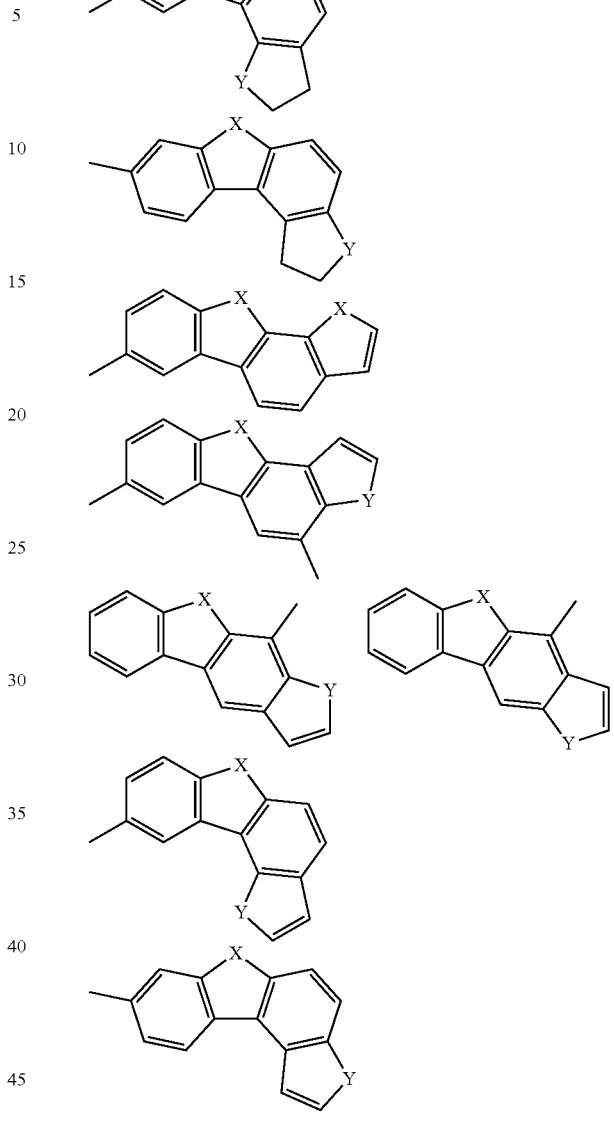

wherein X represents an oxygen atom or a sulfur atom and Y represents an oxygen atom, a sulfur atom, NH, $NR^a$ wherein $R^a$ represents an alkyl group or an aryl group, $CH_2$, or $CR^b{}_2$ wherein $R^b$ represents an alkyl group or an aryl group.

The group or the substituent referred to by "a group" or "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

The optional substituent may be further substituted with an optional substituent mentioned above. The optional substituents may be bonded to each other to form a ring.

The term "unsubstituted" referred to by "substituted or unsubstituted" means that a hydrogen atom is not substituted by the group mentioned above.

Nitrogen-Containing Heterocyclic Derivative

The nitrogen-containing heterocyclic derivative in an aspect of the invention is represented by formula (1):

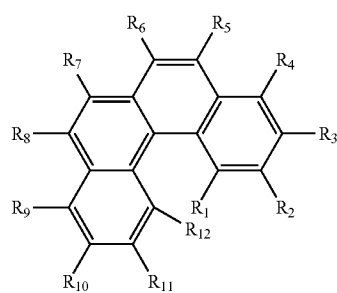

wherein each of $R_1$ to $R_{12}$ independently represents a hydrogen atom or a substituent group, and a pair of adjacent groups selected from $R_1$ to $R_{12}$ may be bonded to each other to form a saturated or unsaturated divalent group which completes a ring, provided that at least one pair of the adjacent groups selected from $R_1$ to $R_{12}$ are bonded to each other to form a ring structure represented by formula (a):

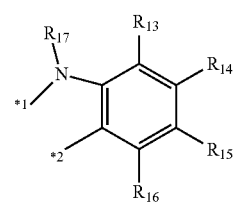

wherein each of $R_{13}$ to $R_{17}$ independently represents a hydrogen atom or a substituent group, a pair of adjacent groups selected from $R_{13}$ to $R_{17}$ may be bonded to each other to form a saturated or unsaturated divalent group which completes a ring, and *1 and *2 are bonded to carbon atoms to which the at least one pair of the adjacent groups selected from $R_1$ to $R_{12}$ are bonded For example, when the adjacent two groups selected from $R_1$ to $R_{12}$ are $R_5$ and $R_6$, *1 is bonded to the carbon atom to which $R_6$ is bonded and *2 is bonded to the carbon atom to which $R_5$ is bonded, or *1 is bonded to the carbon atom to which $R_5$ is bonded and *2 is bonded to the carbon atom to which $R_6$ is bonded.

The nitrogen-containing heterocyclic derivative may be a polymer comprising a repeating unit represented by formula (b) or (d).

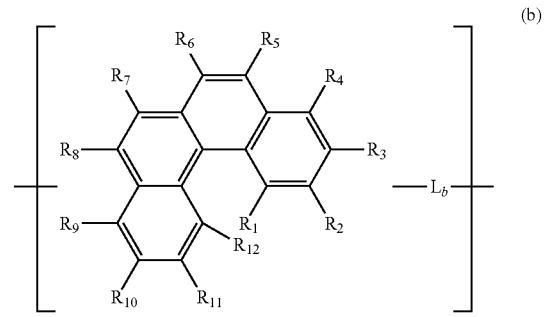

wherein $R_1$ to $R_{12}$ are as defined in formula (1) and $L_b$ represents a single bond or a divalent linking group.

Examples of the divalent linking group represented by $L_b$ include a substituted or unsubstituted arylene group having 6 to 60 ring carbon atoms, a substituted or unsubstituted heteroarylene group having 3 to 60 ring atoms and a substituted or unsubstituted alkylene group having 1 to 50 carbon atoms.

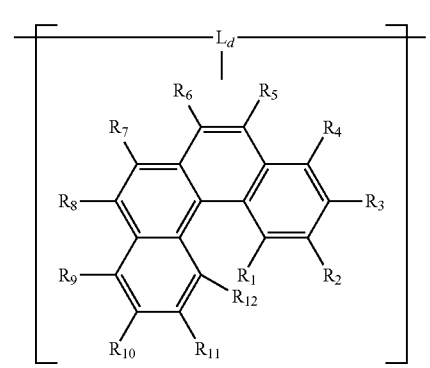

wherein $R_1$ to $R_{12}$ are as defined in formula (1) and $L_d$ represents a trivalent organic group.

The nitrogen-containing heterocyclic derivative is more preferably represented by formula (c):

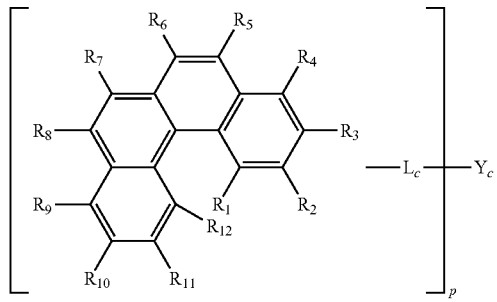

(c)

wherein:

$R_1$ to $R_{12}$ are as defined in formula (1);

$Y_c$ represents a substituted or unsubstituted p-valent aromatic hydrocarbon group having 6 to 60 ring carbon atoms or a substituted or unsubstituted p-valent heterocyclic group having 3 to 60 ring atoms;

$L_c$ represents a single bond, a substituted or unsubstituted arylene group having 6 to 60 ring carbon atoms, a substituted or unsubstituted heteroarylene group having 3 to 60 ring atoms or a substituted or unsubstituted alkylene group having 1 to 50 carbon atoms; and p represents an integer of 1 to 6.

A nitrogen-containing heterocyclic derivative represented by formula (1) wherein any of $R_1$ and $R_2$, $R_2$ and $R_3$, $R_3$ and $R_4$, $R_5$ and $R_6$, $R_7$ and $R_8$, $R_9$ and $R_{10}$, $R_{10}$ and $R_{11}$, and $R_{11}$ and $R_{12}$ forms the ring structure represented by formula (a) is preferred, and a nitrogen-containing heterocyclic derivative represented by formula (2) or (3) wherein $R_5$ and $R_6$ form the ring structure represented by formula (a) is more preferred.

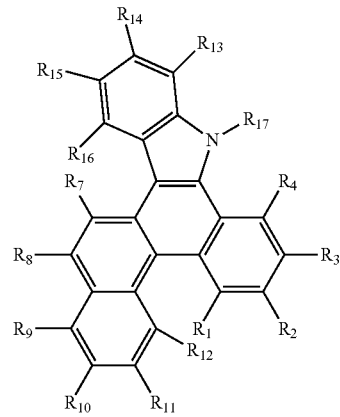

(3)

wherein $R_1$ to $R_4$ and $R_7$ to $R_{17}$ are as defined above and a pair of adjacent two groups selected from $R_1$ to $R_4$ and $R_7$ to $R_{17}$ may be bonded to each other to form a saturated or unsaturated divalent group which completes a ring.

Examples of the pair referred to by "a pair of adjacent two groups selected from $R_1$ to $R_4$ and $R_7$ to $R_{17}$" include $R_1$ and $R_2$, $R_2$ and $R_3$, $R_3$ and $R_4$, $R_7$ and $R_8$, $R_8$ and $R_9$, $R_9$ and $R_{10}$, $R_{10}$ and $R_{11}$, $R_{11}$ and $R_{12}$, $R_{13}$ and $R_{14}$, $R_{14}$ and $R_{15}$, $R_{15}$ and $R_{16}$, $R_1$ and $R_{12}$, $R_{13}$ and $R_{17}$, $R_7$ and $R_{17}$, $R_4$ and $R_{17}$, $R_4$ and $R_{16}$, and $R_7$ and $R_{16}$. Two or more pairs may form two or more saturated or unsaturated divalent groups each of which completes a ring.

The nitrogen-containing heterocyclic derivative of formula (1) is also preferably represented by any of formulae (4) to (21).

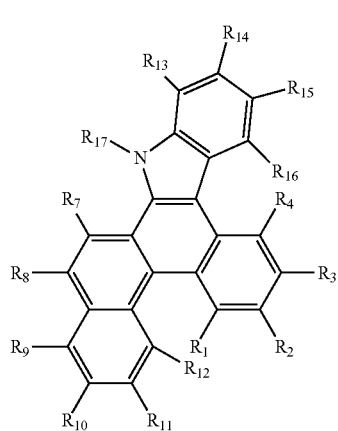

(2)

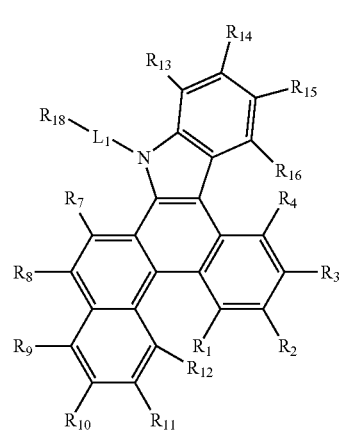

(4)

(5)

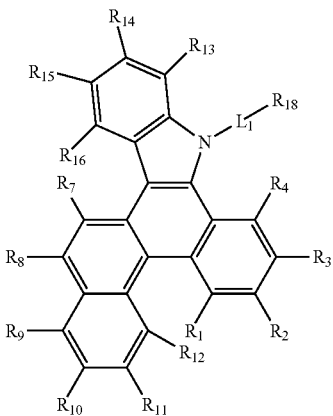

wherein $R_1$ to $R_4$ and $R_7$ to $R_{16}$ are as defined above; a pair of adjacent two groups selected from $R_1$ to $R_4$ and $R_7$ to $R_{16}$ may be bonded to each other to form a saturated or unsaturated divalent group which completes a ring; $R_{18}$ represents a substituted or unsubstituted aryl group having 6 to 30 ring carbon atoms or a substituted or unsubstituted nitrogen-containing heterocyclic group having 5 to 30 ring atoms; and $L_1$ represents a single bond or a substituted or unsubstituted arylene group having 6 to 30 ring carbon atoms.

Examples of the pair referred to by "a pair of adjacent two groups selected from $R_1$ to $R_4$ and $R_7$ to $R_{16}$" include $R_1$ and $R_2$, $R_2$ and $R_3$, $R_3$ and $R_4$, $R_7$ and $R_8$, $R_8$ and $R_9$, $R_9$ and $R_{10}$, $R_{10}$ and $R_{11}$, $R_{11}$ and $R_{12}$, $R_{13}$ and $R_{14}$, $R_{14}$ and $R_{15}$, $R_{15}$ and $R_{16}$, $R_1$ and $R_{12}$, $R_4$ and $R_{16}$, and $R_7$ and $R_{16}$. Two or more pairs may form two or more saturated or unsaturated divalent groups each of which completes a ring.

(6)

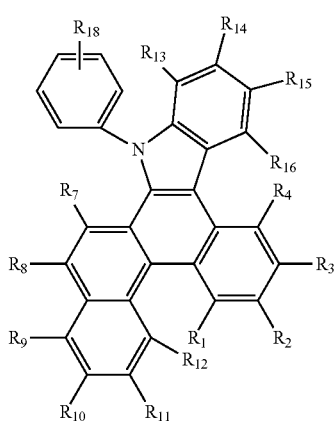

(7)

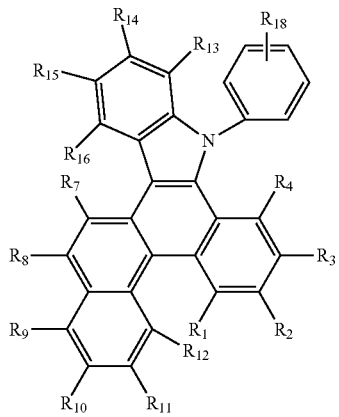

wherein $R_1$ to $R_4$, $R_7$ to $R_{16}$ and $R_{18}$ are as defined above and a pair of adjacent two groups selected from $R_1$ to $R_4$, $R_7$ to $R_{16}$ and $R_{18}$ may be bonded to each other to form a saturated or unsaturated divalent group which completes a ring.

Examples of the pair referred to by "a pair of adjacent two groups selected from $R_1$ to $R_4$, $R_7$ to $R_{16}$ and $R_{18}$" include $R_1$ and $R_2$, $R_2$ and $R_3$, $R_3$ and $R_4$, $R_7$ and $R_8$, $R_8$ and $R_9$, $R_9$ and $R_{10}$, $R_{10}$ and $R_{11}$, $R_{11}$ and $R_{12}$, $R_{13}$ and $R_{14}$, $R_{14}$ and $R_{15}$, $R_{15}$ and $R_{16}$, $R_1$ and $R_{12}$, $R_4$ and $R_{16}$, $R_7$ and $R_{16}$, $R_{13}$ and $R_{18}$, $R_7$ and $R_{18}$, and $R_4$ and $R_{18}$. Two or more pairs may form two or more saturated or unsaturated divalent groups each of which completes a ring.

(8)

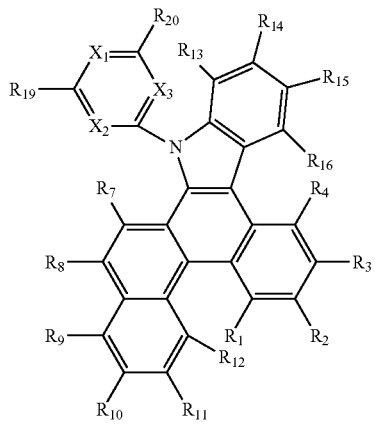

(9)

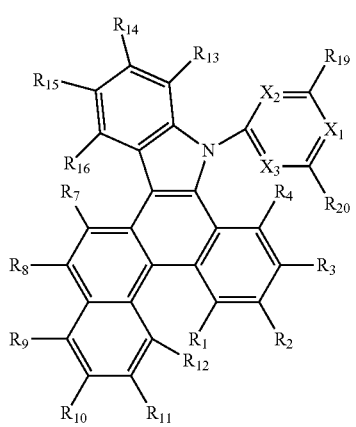

wherein each of $X_1$ to $X_3$ independently represents $C(R_{21})$ or a nitrogen atom; $R_1$ to $R_4$, $R_7$ to $R_{16}$ are as defined above; a pair of adjacent two groups selected from $R_1$ to $R_4$ and $R_7$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms, or a substituted or unsubstituted nitrogen-containing heterocyclic group having 5 to 30 ring atoms, and a pair of adjacent two groups selected from $R_{19}$ to $R_{21}$ may be bonded to each other to form a saturated or unsaturated divalent group which completes a ring.

Examples of the pair referred to by "a pair of adjacent two groups selected from $R_1$ to $R_4$ and $R_7$ to $R_{16}$" are the same as those mentioned above with respect to formulae (4) and (5).

Examples of the pair referred to by "a pair of adjacent two groups selected from $R_{19}$ to $R_{21}$" include $R_{21}$ and $R_{19}$, and $R_{21}$ and $R_{20}$ when $X_1$ is $C(R_{21})$, $R_{21}$ and $R_{19}$ when $X_2$ is $C(R_{21})$, and $R_{21}$ and $R_{20}$ when $X_3$ is $C(R_{21})$. Two or more pairs may form two or more saturated or unsaturated divalent groups each of which completes a ring.

Preferably, each of $R_{19}$ and $R_{20}$ in formulae (8) and (9) independently represents a substituted or unsubstituted aryl group having 6 to 30 ring carbon atoms or a substituted or unsubstituted nitrogen-containing heterocyclic group having 5 to 30 ring atoms.

wherein each of $X_1$ to $X_3$ independently represents $C(R_{21})$ or a nitrogen atom; $R_1$ to $R_4$ and $R_7$ to $R_{16}$ are as defined above; a pair of adjacent two groups selected from $R_1$ to $R_4$ and $R_7$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ to $R_{21}$ may be bonded to each other to form a saturated or unsaturated divalent group which completes a ring.

Examples of the pair referred to by "a pair of adjacent two groups selected from $R_1$ to $R_4$ and $R_7$ to $R_{16}$" are the same as those mentioned above with respect to formulae (4) and (5), and examples of the pair referred to by "a pair of adjacent two groups selected from $R_{19}$ to $R_{21}$" are the same as those mentioned above with respect to formulae (8) and (9).

Preferably, each of $R_{19}$ and $R_{20}$ in formulae (10) and (11) independently represents a substituted or unsubstituted aryl group having 6 to 30 ring carbon atoms or a substituted or unsubstituted nitrogen-containing heterocyclic group having 5 to 30 ring atoms.

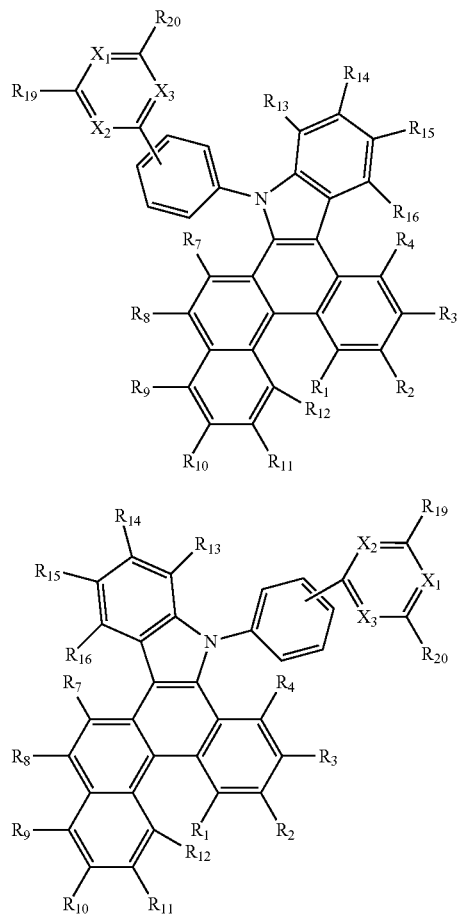

(10)

(11)

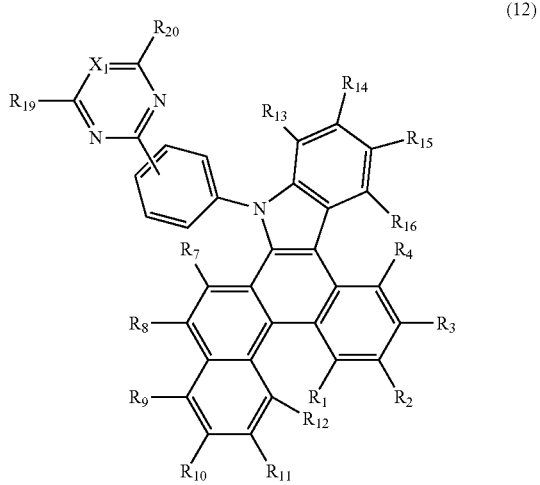

(12)

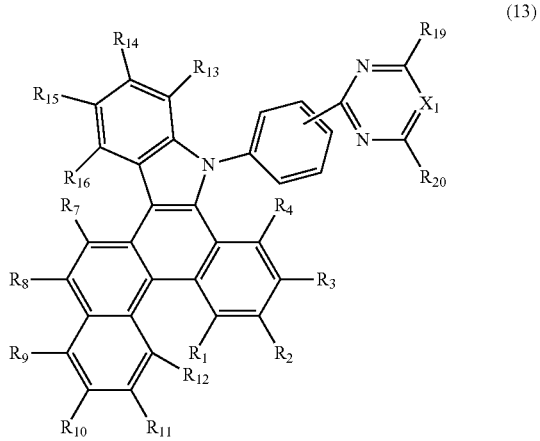

(13)

wherein $X_1$ represents $C(R_{21})$ or a nitrogen atom; $R_1$ to $R_4$ and $R_7$ to $R_{16}$ are as defined above; a pair of adjacent two groups selected from $R_1$ to $R_4$ and $R_7$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ to $R_{21}$ may be bonded to each other to form a saturated or unsaturated divalent group which completes a ring.

Examples of the pair referred to by "a pair of adjacent two groups selected from $R_1$ to $R_4$ and $R_7$ to $R_{16}$" are the same as those mentioned above with respect to formulae (4) and (5).

Examples of the pair referred to by "a pair of adjacent two groups selected from $R_{19}$ to $R_{21}$" include $R_{21}$ and $R_{19}$, and $R_{21}$ and $R_{20}$ when $X_1$ is $C(R_{21})$. Two or more pairs may form two or more saturated or unsaturated divalent groups each of which completes a ring.

Preferably, each of $R_{19}$ and $R_{20}$ in formulae (12) and (13) independently represents a substituted or unsubstituted aryl group having 6 to 30 ring carbon atoms or a substituted or unsubstituted nitrogen-containing heterocyclic group having 5 to 30 ring atoms.

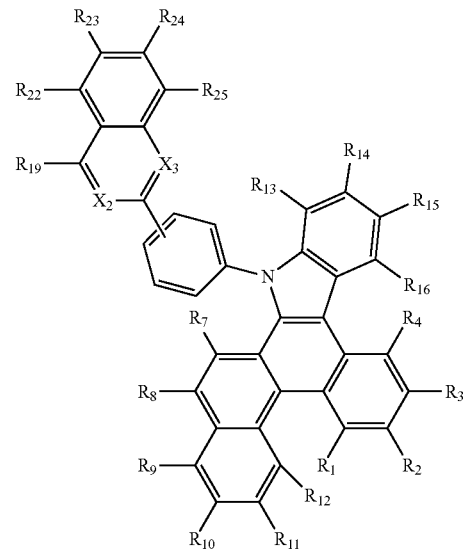

(14)

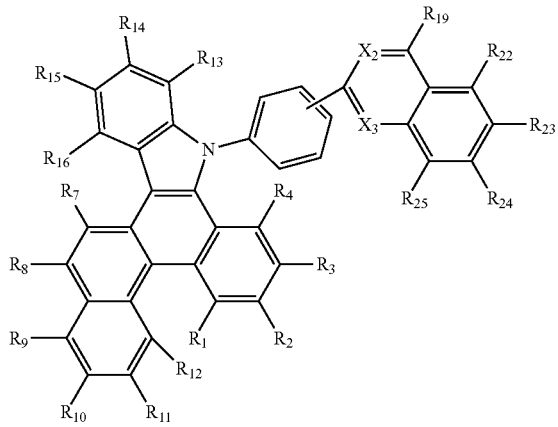

(15)

wherein each of $X_2$ to $X_3$ independently represents $C(R_{21})$ or a nitrogen atom; $R_1$ to $R_4$ and $R_7$ to $R_{16}$ are as defined above;

a pair of adjacent two groups selected from $R_1$ to $R_4$ and $R_7$ to $R_{16}$ may be bonded to each other to form a saturated or unsaturated divalent group which completes a ring; each of $R_{19}$, $R_{21}$ to $R_{25}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ and $R_{21}$ to $R_{25}$ may be bonded to each other to form a saturated or unsaturated divalent group which completes a ring.

Examples of the pair referred to by "a pair of adjacent two groups selected from $R_1$ to $R_4$ and $R_7$ to $R_{16}$" are the same as those mentioned above with respect to formulae (4) and (5).

$R^{19}$ in formulae (14) and (15) preferably represents a substituted or unsubstituted aryl group having 6 to 30 ring carbon atoms or a substituted or unsubstituted nitrogen-containing heterocyclic group having 5 to 30 ring atoms.

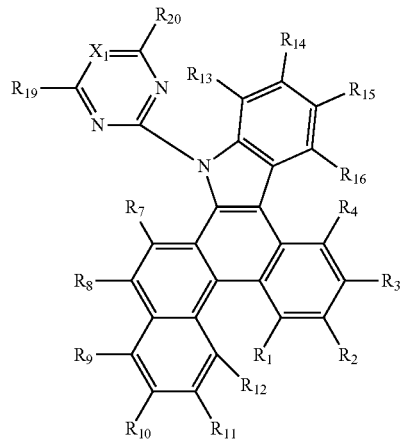

(16)

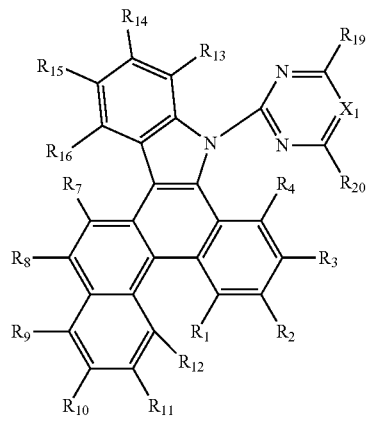

(17)

wherein $X_1$ represents $C(R_{21})$ or a nitrogen atom; $R_1$ to $R_4$ and $R_7$ to $R_{16}$ are as defined above, a pair of adjacent two groups selected from $R_1$ to $R_4$ and $R_7$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ to $R_{21}$ may be bonded to each other to form a saturated or unsaturated divalent group which completes a ring.

Examples of the pair referred to by "a pair of adjacent two groups selected from $R_1$ to $R_4$ and $R_7$ to $R_{16}$" are the same as those mentioned above with respect to formulae (4) and (5), and examples of the pair referred to by "a pair of adjacent two groups selected from $R_{19}$ to $R_{21}$" are the same as those mentioned above with respect to formulae (12) and (13).

Preferably, each of $R_{19}$ and $R_{20}$ in formulae (16) and (17) independently represents a substituted or unsubstituted aryl group having 6 to 30 ring carbon atoms or a substituted or unsubstituted nitrogen-containing heterocyclic group having 5 to 30 ring atoms.

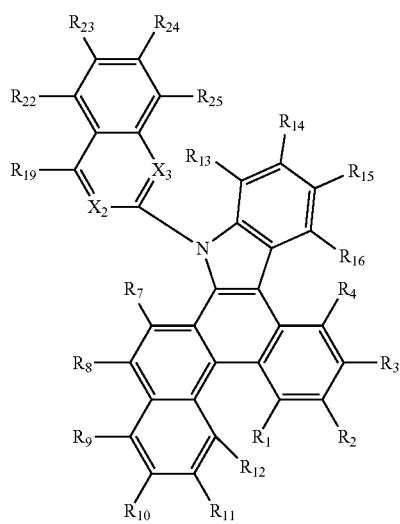

(18)

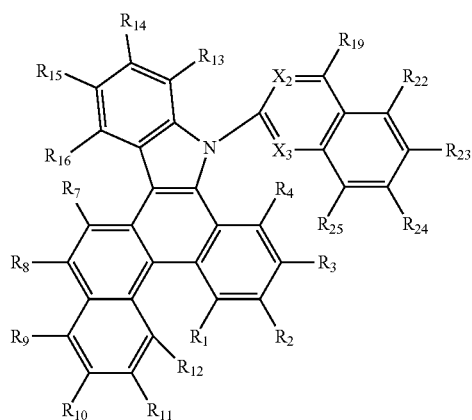

(19)

wherein each of $X_2$ to $X_3$ independently represents $C(R_{21})$ or a nitrogen atom; $R_1$ to $R_4$ and $R_7$ to $R_{16}$ are as defined above; a pair of adjacent two groups selected from $R_1$ to $R_4$ and $R_7$ to $R_{16}$ may be bonded to each other to form a saturated or unsaturated divalent group which completes a ring; each of $R_{19}$ and $R_{21}$ to $R_{25}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ and $R_{21}$ to $R_{25}$ may be bonded to each other to form a saturated or unsaturated divalent group which completes a ring.

Examples of the pair referred to by "a pair of adjacent two groups selected from $R_1$ to $R_4$ and $R_{16}$" are the same as those mentioned above with respect to formulae (4) and (5).

$R_{19}$ in formulae (18) and (19) preferably represents a substituted or unsubstituted aryl group having 6 to 30 ring carbon atoms or a substituted or unsubstituted nitrogen-containing heterocyclic group having 5 to 30 ring atoms.

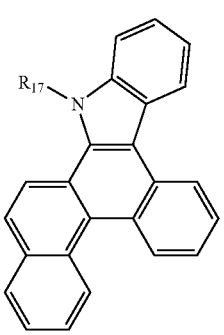

(20)

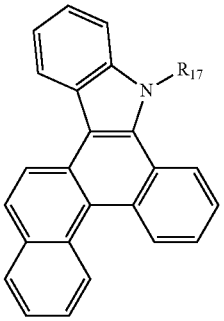

(21)

wherein $R_{17}$ is as defined above.

The substituent group represented by any of $R_1$ to $R_{17}$ and $R_{22}$ to $R_{25}$ in formulae (1) to (21) and (b) to (d) is independently selected preferably from the group (A), more preferably from the group (B), still more preferably from the group (C), and particularly preferably from the group (D).

The group (A) consists of a substituted or unsubstituted alkyl group having 1 to 50 carbon atoms, a substituted or unsubstituted cycloalkyl group having 3 to 50 ring carbon atoms, a substituted or unsubstituted aryl group (a synonym for an aromatic hydrocarbon group and the same applies below) having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group (a synonym for a heterocyclic group and the same applies below) having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, a alkyl- or aryl-substituted carbonyl group, a carboxyl group, a vinyl group, a (meth)acryloyl group, an epoxy group, and an oxetanyl group.

The group (B) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 51 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a substituted or unsubstituted alkyl group having 1 to 50 carbon atoms, and a substituted or unsubstituted aryl group having 6 to 60 ring carbon atoms.

The group (C) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 51 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, and a nitro group.

The group (D) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a halogen atom, and a cyano group.

Examples of the alkyl group having 1 to 50, preferably 1 to 18, more preferably 1 to 8 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontanyl group. Preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. More preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups).

Examples of the cycloalkyl group having 3 to 50, preferably 3 to 10, more preferably 3 to 8, still more preferably 5 or 6 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 60, preferably 6 to 25, more preferably 6 to 18 ring carbon atoms include a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, and a dibenzanthryl group.

The heteroaryl group having 5 to 60, preferably 5 to 24, more preferably 5 to 13 ring atoms include at least one, preferably 1 to 5, more preferably 1 to 3, and still more preferably 1 or 2 hetero atoms, for example, a nitrogen atom, a sulfur atom, an oxygen atom, and a phosphorus atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isooxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, and a dinaphthothienothiophenyl group.

In addition, examples of the heteroaryl group having 5 to 60 ring atoms preferably include mono-valent groups derived from the following compounds by removing one hydrogen atom:

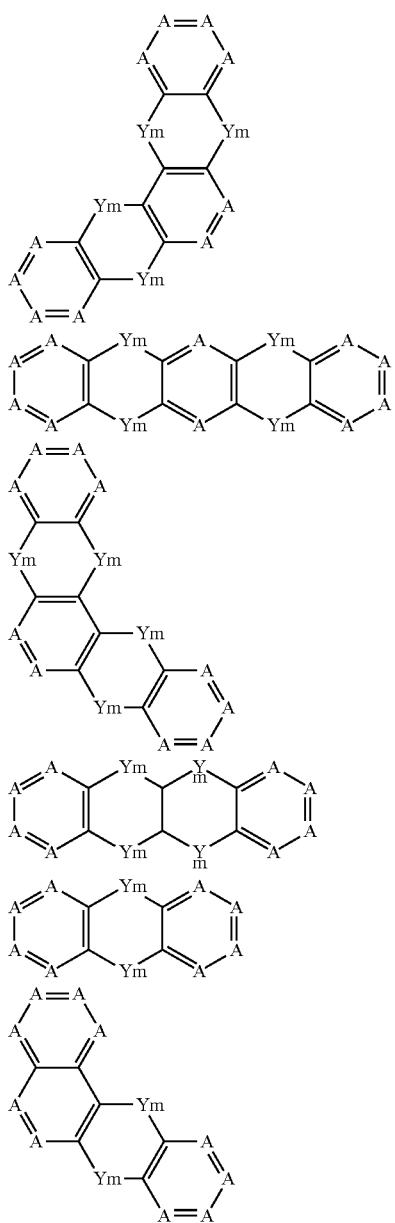

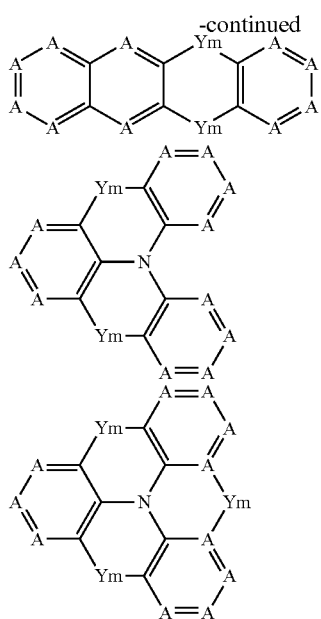

wherein:
each A independently represents $CR^{100}$ or a nitrogen atom;
each $R^{100}$ independently represents a hydrogen atom or a substituent group;
each Y independently represents a single bond, $C(R^{101})(R^{102})$, an oxygen atom, a sulfur atom, or $N(R^{103})$;
each of $R^{101}$, $R^{102}$ and $R^{103}$ independently represents a hydrogen atom or a substituent group; and
m independently represents 0 or 1.

The substituent group referred to above is selected from those mentioned above.

Examples of the aryl group having 6 to 60, preferably 6 to 25, more preferably 6 to 18 ring carbon atoms included in the aralkyl group having 7 to 61 total carbon atoms are the same as those mentioned above.

Examples of the alkyl group having 1 to 50, preferably 1 to 18, more preferably 1 to 8 carbon atoms and the aryl group having 6 to 60, preferably 6 to 25, more preferably 6 to 18 ring carbon atoms each included in the mono- or di-substituted amino group are the same as those mentioned above.

Examples of the alkyl group having 1 to 50, preferably 1 to 18, more preferably 1 to 8 carbon atoms included in the alkoxy group are the same as those mentioned above.

Examples of the aryl group having 6 to 60, preferably 6 to 25, more preferably 6 to 18 ring carbon atoms included in the aryloxy group are the same as those mentioned above.

Examples of the alkyl group having 1 to 50, preferably 1 to 18, more preferably 1 to 8 carbon atoms and the aryl group having 6 to 60, preferably 6 to 25, more preferably 6 to 18 ring carbon atoms each included in the mono-, di- or tri-substituted silyl group are the same as those mentioned above.

Examples of the haloalkyl group having 1 to 50, preferably 1 to 18, more preferably 1 to 8 carbon atoms include those obtained by replacing one or more hydrogen atoms of the alkyl groups mentioned above with a halogen atom, such as a fluorine atom, a chlorine atom, a bromine atom and an iodine atom.

Examples of the alkyl group having 1 to 50, preferably 1 to 18, more preferably 1 to 8 carbon atoms and the aryl group having 6 to 60, preferably 6 to 25, more preferably 6 to 18 ring carbon atoms each included in the substituted sulfonyl group are the same as those mentioned above.

Examples of the alkyl group having 1 to 50, preferably 1 to 18, more preferably 1 to 8 carbon atoms and the aryl group having 6 to 60, preferably 6 to 25, more preferably 6 to 18 ring carbon atoms each included in the di-substituted phosphoryl group are the same as those mentioned above.

Examples of the substituted or unsubstituted arylene group having 6 to 60 ring carbon atoms represented by $L_b$ of formula (b), and examples of the substituted or unsubstituted arylene group having 6 to 60 ring carbon atoms represented by $L_c$ of formula (c) include those obtained by removing one hydrogen atom from the aryl groups mentioned above.

Examples of the substituted or unsubstituted heteroarylene group having 3 to 60 ring atoms represented by $L_b$ of formula (b), and examples of the substituted or unsubstituted heteroarylene group having 3 to 60 ring atoms represented by $L_c$ of formula (c) include those obtained by removing one hydrogen atom from the heteroaryl groups mentioned above.

Examples of the substituted or unsubstituted alkylene group having 1 to 50 carbon atoms represented by $L_b$ of formula (b), and examples of the substituted or unsubstituted alkylene group having 1 to 50 carbon atoms represented by $L_c$ of formula (c) include those obtained by removing one hydrogen atom from the alkyl groups mentioned above.

Examples of the trivalent organic group represented by $L_d$ of formula (d) include those obtained by removing one hydrogen atom from the divalent groups mentioned above with respect to $L_b$ and $L_c$.

When the pair of adjacent two groups selected from $R_1$ to $R_{25}$ of formulae (1) to (21) are bonded to each other to form a ring, the nitrogen-containing heterocyclic derivative in an aspect of the invention may include a substituted or unsubstituted arylene group having 6 to 60 ring carbon atoms or a substituted or unsubstituted heteroarylene group having 5 to 60 ring atoms.

Examples of the substituted or unsubstituted arylene group having 6 to 60 ring carbon atoms include those obtained by removing one hydrogen atom from the aryl groups mentioned above.

Examples of the substituted or unsubstituted heteroarylene group having 5 to 60 ring atoms include those obtained by removing one hydrogen atom from the heteroaryl groups mentioned above.

In the nitrogen-containing heterocyclic derivative in an aspect of the invention, the group preferably includes a ring-containing group, particularly, $R_{17}$ preferably includes the ring-containing group.

A material for organic EL devices which comprises a nitrogen-containing heterocyclic derivative including the ring-containing group exhibits an effect of, for example, improving the film properties of an organic thin film which comprises the material.

Examples of the ring-containing group include those having a group selected from a substituted or unsubstituted cycloalkyl group having 5 to 60, preferably 3 to 6, and more preferably 5 or 6 ring carbon atoms, a substituted or unsubstituted aryl group having 6 to 60, preferably 6 to 24, and more preferably 6 to 18 ring carbon atoms, an aralkyl group having 7 to 61 carbon atoms in total, which includes a substituted or unsubstituted aryl group having 6 to 60, preferably 6 to 24, and more preferably 6 to 18 ring carbon atoms, an amino group having a substituted or unsubstituted aryl group having 6 to 60, preferably 6 to 24, and more preferably 6 to 18 ring carbon atoms, an aryloxy group having a substituted or unsubstituted aryl group having 6 to 60, preferably 6 to 24, and more preferably 6 to 18 ring carbon atoms, a silyl group having a substituted or unsubstituted aryl group having 6 to 60, preferably 6 to 24, and more preferably 6 to 18 ring carbon atoms, a substituted or unsubstituted heteroaryl group having 5 to 60, preferably 5 to 24, and more preferably 5 to 13 ring atoms, a sulfonyl group substituted with a substituted or unsubstituted aryl group having 6 to 60, preferably 6 to 24, and more preferably 6 to 18 ring carbon atoms, and a phosphonyl group substituted with a substituted or unsubstituted aryl group having 6 to 60, preferably 6 to 24, and more preferably 6 to 18 ring carbon atoms. Preferred are those including a substituted or unsubstituted aryl group having 6 to 60 ring carbon atoms, a substituted or unsubstituted heteroaryl group having 5 to 60 ring atoms, or a mono- or disubstituted amino group having a substituted or unsubstituted aryl group having 6 to 60 ring carbon atoms. The details of the above groups are the same as those mentioned above.

Of the above, a substituted or unsubstituted aryl group having 6 to 60 ring carbon atoms and a substituted or unsubstituted heteroaryl group having 5 to 60 ring atoms are preferred.

The ring-containing group may be a substituent group having a ring-containing group thereon. Examples of such a substituent group are those as mentioned above.

$R_{17}$ is preferably a group represented by formula (I) and more preferably a group represented by formula (II) or (III);

$$*\text{-}L_1\text{-}R_{18} \quad (I)$$

wherein $L_1$ represents a single bond or a substituted or unsubstituted arylene group having 6 to 30 ring carbon atoms, $R_{18}$ represents a substituted or unsubstituted aryl group having 6 to 30 ring carbon atoms or a substituted or unsubstituted nitrogen-containing heterocyclic group having 5 to 30 ring atoms, and * represents a bonding site;

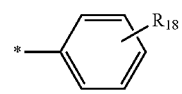

(II)

wherein $R_{18}$ represents a substituted or unsubstituted aryl group having 6 to 30 ring carbon atoms or a substituted or unsubstituted nitrogen-containing heterocyclic group having 5 to 30 ring atoms and * represents a bonding site;

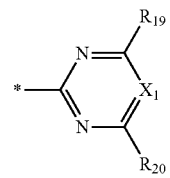

(III)

wherein $X_1$ represents $C(R_{21})$ or a nitrogen atom, each of $R_{19}$ and $R_{20}$ independently represents a substituted or unsubstituted aryl group having 6 to 30 ring carbon atoms or a substituted or unsubstituted nitrogen-containing heterocyclic group having 5 to 30 ring atoms, adjacent groups may be bonded to each other to form a saturated or unsaturated ring structure, and * represents a bonding site.

Namely, the nitrogen-containing heterocyclic derivative represented by formula (4) or (5) is a compound wherein $R_{17}$ is a group represented by formula (I).

The nitrogen-containing heterocyclic derivative represented by formula (6) or (7) is a compound wherein $R_{17}$ is a group represented by formula (II), and the nitrogen-containing heterocyclic derivative represented by formula (16) or (17) is a compound wherein $R_{17}$ is a group represented by formula (III).

Examples of the aryl group in the substituted or unsubstituted aryl group having 6 to 30 ring carbon atoms which is represented by $R_{18}$ to $R_{25}$ of formulae (I) to (III) and (4) to (19) include those having 6 to 30 ring carbon atoms which are selected from the aryl groups mentioned above.

Examples of the nitrogen-containing heterocyclic group in the substituted or unsubstituted nitrogen-containing heterocyclic group having 5 to 30 ring atoms which is represented by $R_{18}$ to $R_{25}$ of formulae (I) to (III) and (4) to (19) include those having 5 to 30 ring atoms including a nitrogen atom which are selected from the heteroaryl groups mentioned above, such as a pyridyl group, a pyrimidyl group, a triazinyl group, a pyrazinyl group, a quinolyl group, an isoquinolyl group, a quinoxalinyl group, a quinazolyl group, a phenanthrolinyl group, a dibenzoquinoxalinyl group, a pyrrolyl group, an indolyl group, a carbazolyl group, an imidazolyl group, a benzimidazolyl group, an imidazopyridinyl group, an indolizinyl group, a benzocarbazolyl group, and a dibenzocarbazolyl group.

In $L_1$ of formula (I), (4) or (5), examples of the substituted or unsubstituted arylene group having 6 to 30 ring carbon atoms include divalent groups obtained by removing one hydrogen atom from the aryl groups mentioned above, and examples of the substituted or unsubstituted nitrogen-containing heterocyclic group having 5 to 30 ring atoms include divalent groups obtained by removing one hydrogen atom from the nitrogen-containing heterocyclic groups mentioned above with respect to $R_{16}$ to $R_{19}$.

Example of $R_{18}$ to $R_{21}$ is preferably a group represented by formula (i), more preferably a group represented by formula (ii), and still more preferably a group represented by formula (iii):

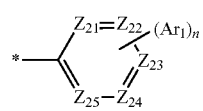

(i)

wherein:

each of $Z_{21}$ to $Z_{25}$ independently represents $C(R_1)$ or a nitrogen atom;

$R_1$ independently represents a hydrogen atom or a bond to $Ar_1$;

$Ar_1$ independently represents a substituent group, preferably a substituted or unsubstituted aryl group having 6 to 60 ring carbon atoms or a substituted or unsubstituted heteroaryl group having 5 to 60 ring atoms;

n represents an integer of 0 to 5; and

* represents a bonding site;

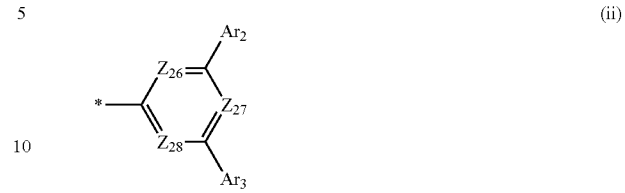

(ii)

wherein;

each of $Z_{26}$ to $Z_{28}$ independently represents MO or a nitrogen atom;

$R_1$ independently represents a hydrogen atom or a substituent group;

each of $Ar_2$ and $Ar_3$ independently represents a hydrogen atom or a substituent group, preferably a substituted or unsubstituted aryl group having 6 to 60 ring carbon atoms or a substituted or unsubstituted heteroaryl group having 5 to 60 ring atoms; and

* represents a bonding site; and

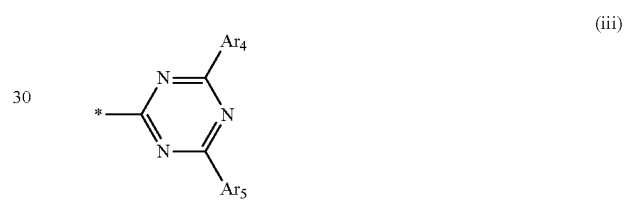

(iii)

wherein each of $Ar_4$ and $Ar_y$ independently represents a hydrogen atom or a substituent group, preferably a substituted or unsubstituted aryl group having 6 to 60 ring carbon atoms or a substituted or unsubstituted heteroaryl group having 5 to 60 ring atoms, and more preferably an aryl group having 6 to 18 ring carbon atoms or a heteroaryl group having 5 to 13 ring atoms, and * represents a bonding site.

The substituent group represented by $Ar_1$ of formula (i), $Ar_2$ and $Ar_3$ of formula (ii), and $Ar_4$ and $Ar_5$ of formula (iii) is selected from preferably the group (A), more preferably the group (B), still more preferably the group (C), and particularly preferably the group (D), each described above.

Examples of the nitrogen-containing heterocyclic derivatives represented by formulae (1) to (21) are shown below, although not limited thereto.

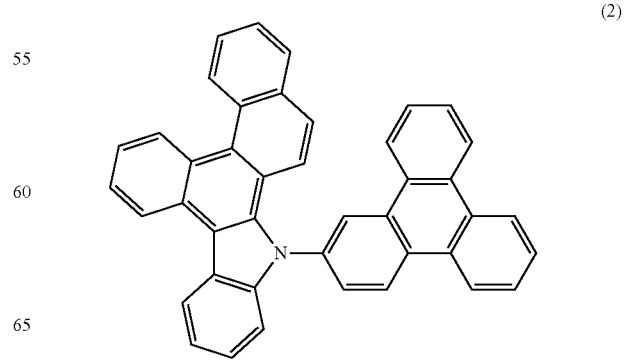

(2)

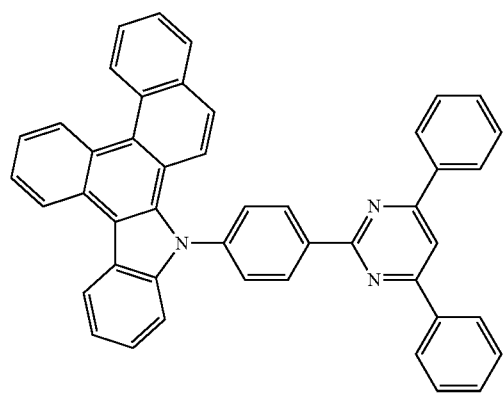
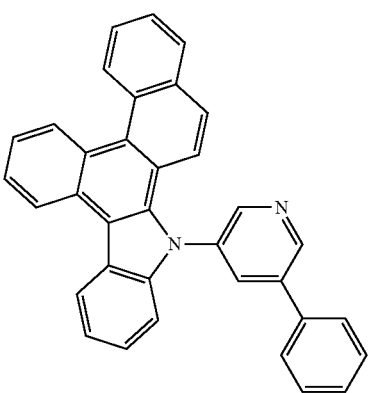
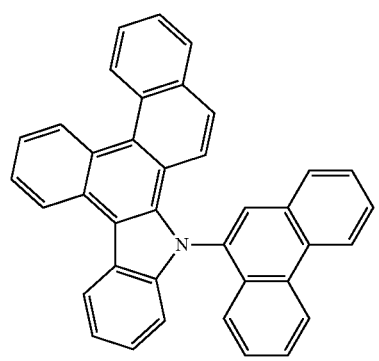
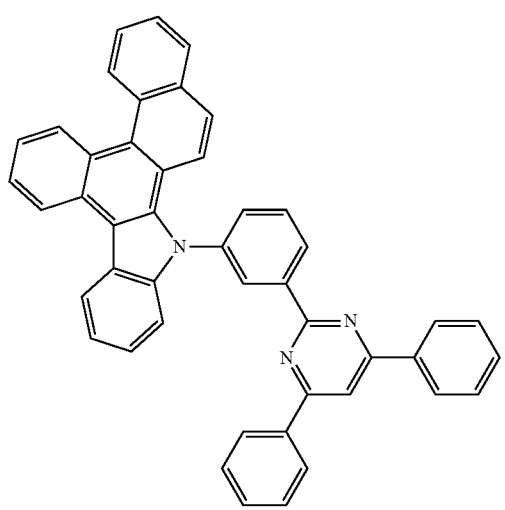
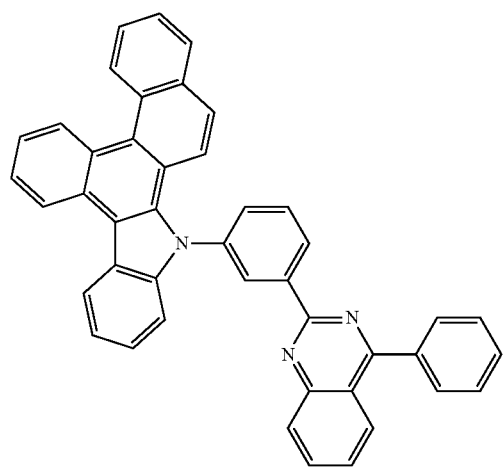
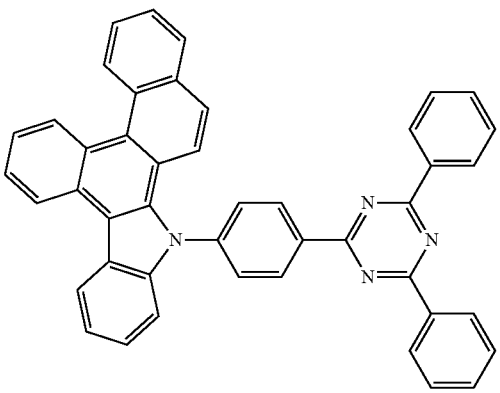
(6)
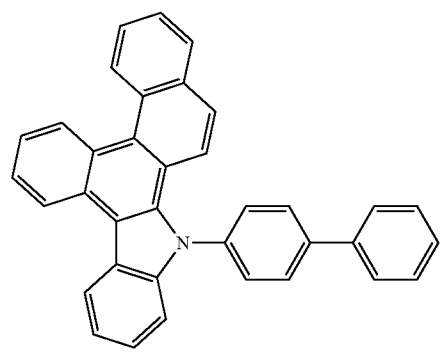
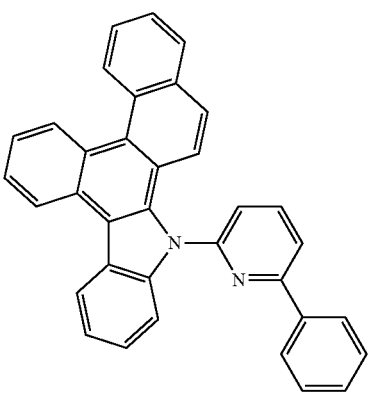

-continued
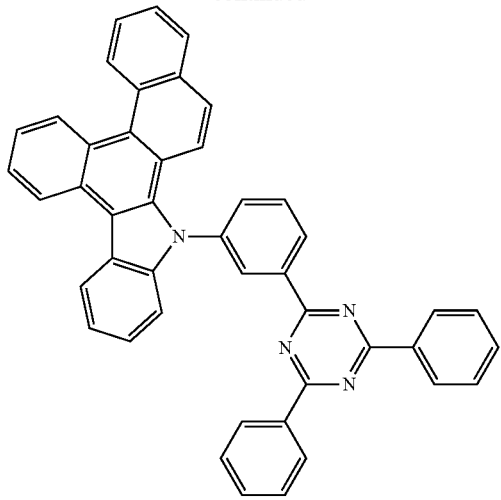
(7)
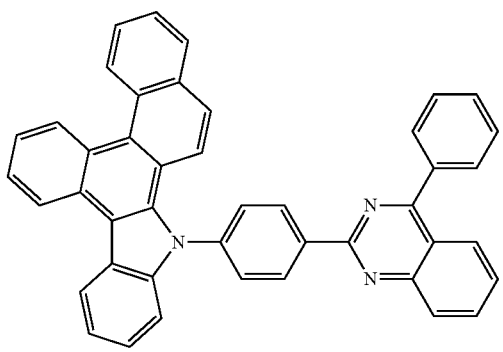
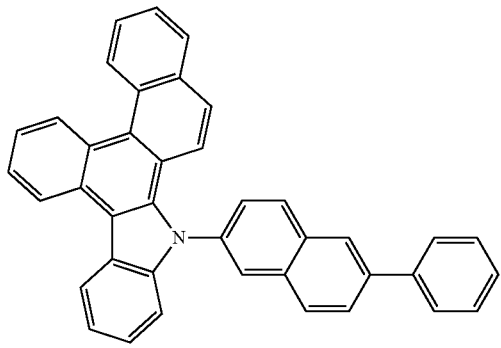
(4)
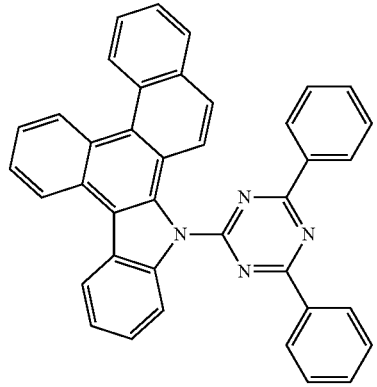
-continued
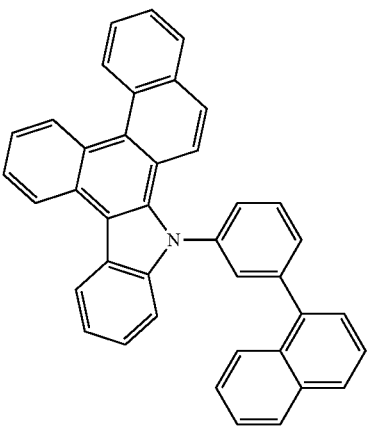
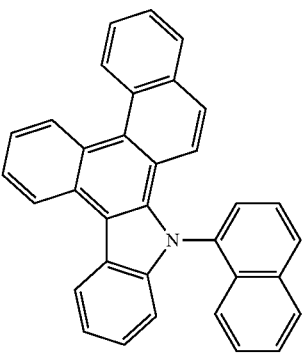
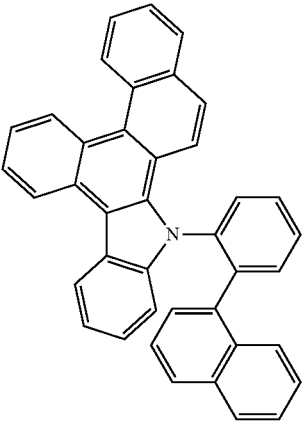
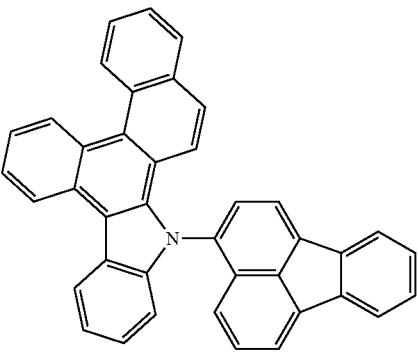

31
-continued
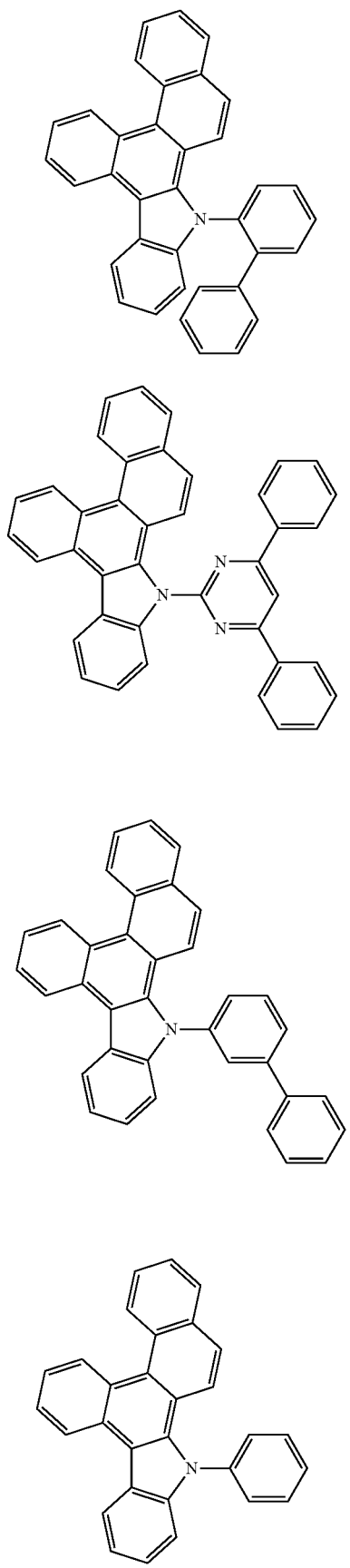
(3)
(1)
32
-continued
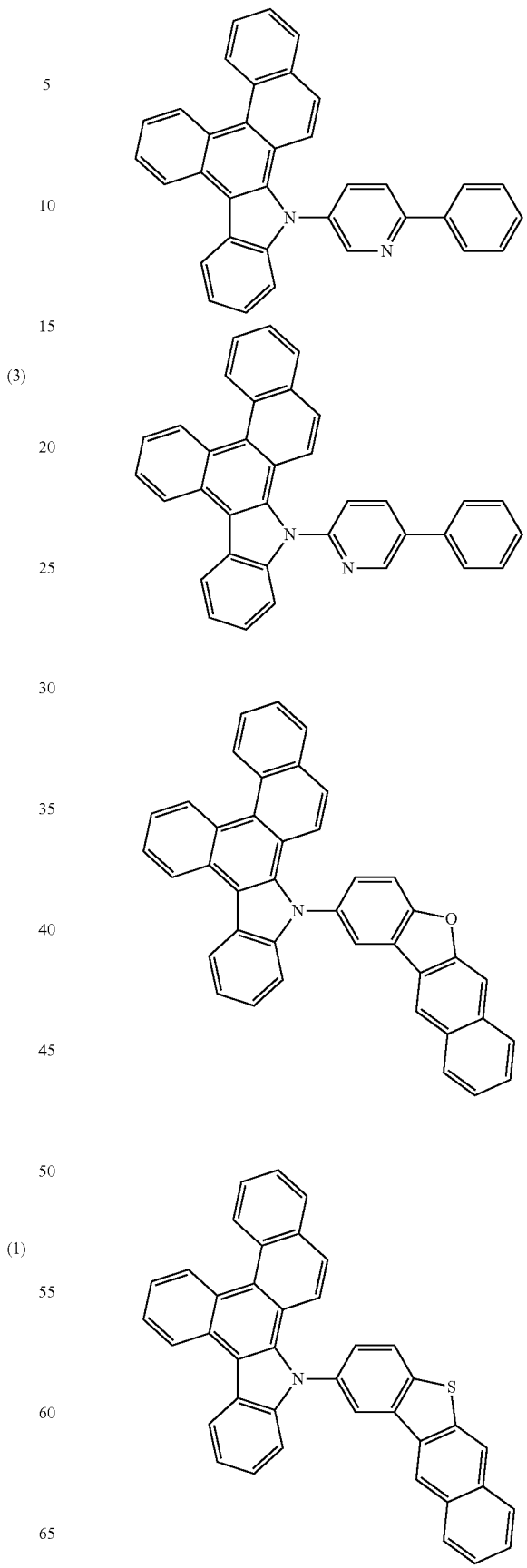

33
-continued
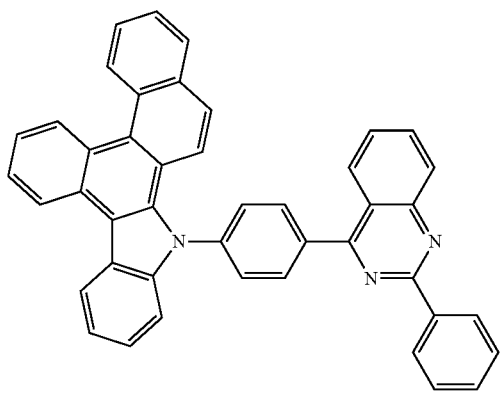
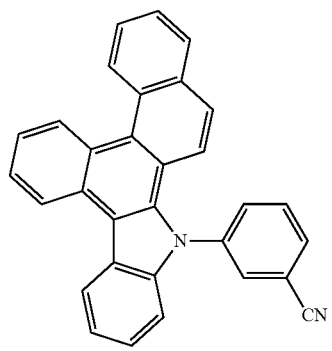
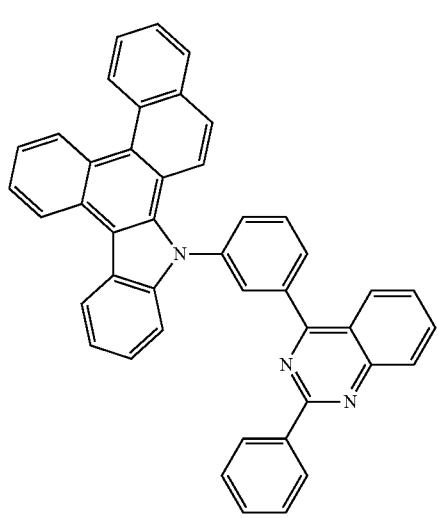
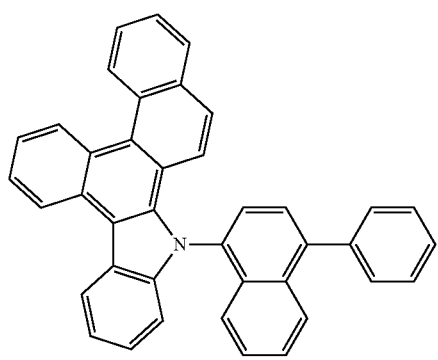
34
-continued
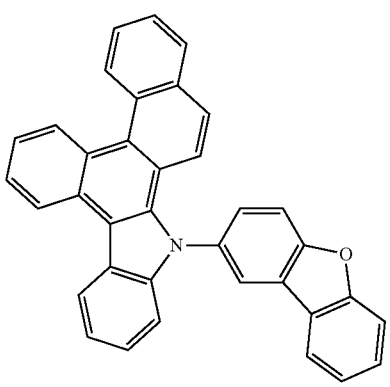
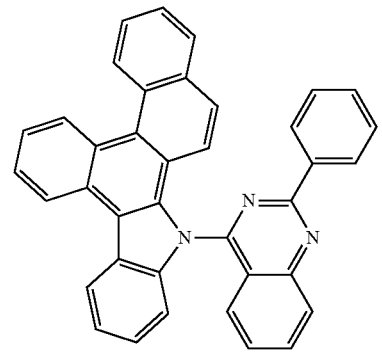
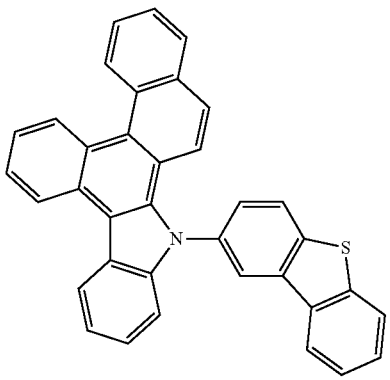
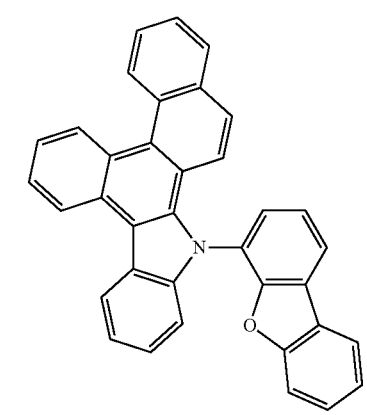

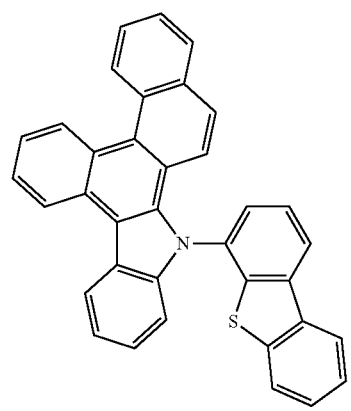
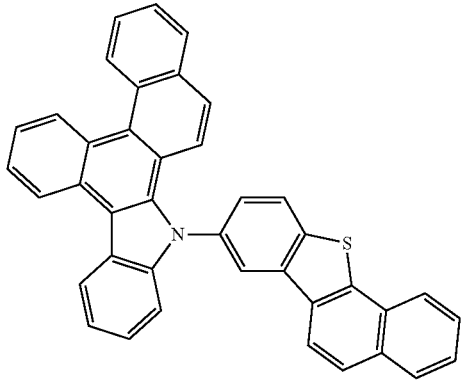
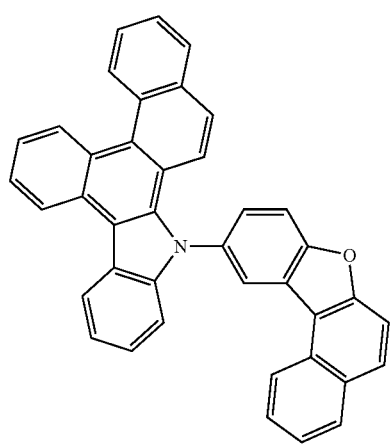
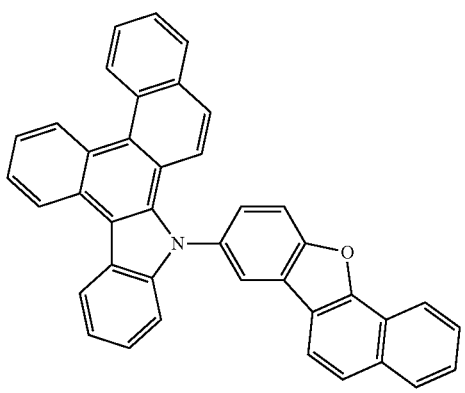
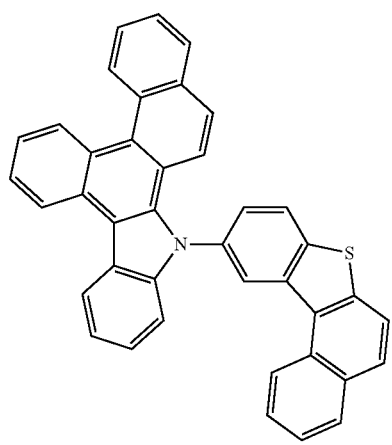
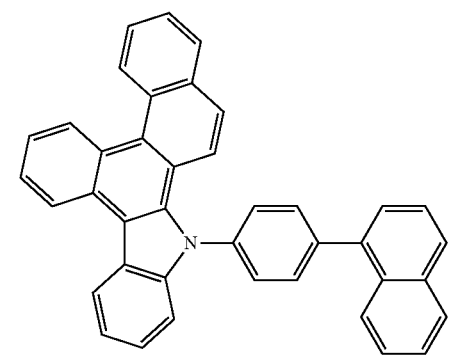
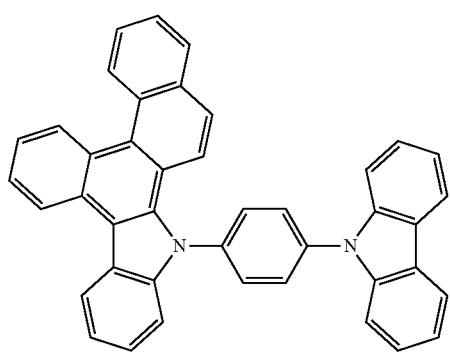
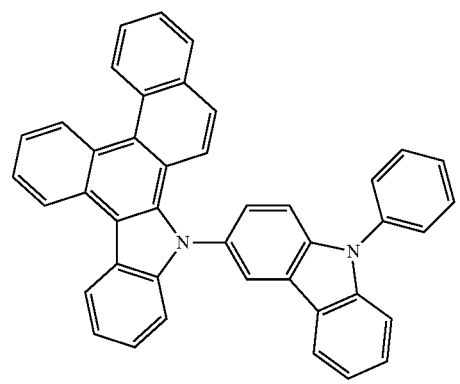

37
-continued
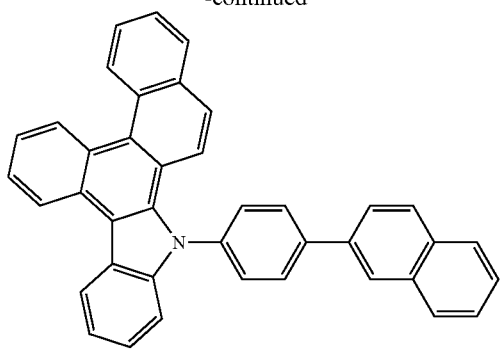
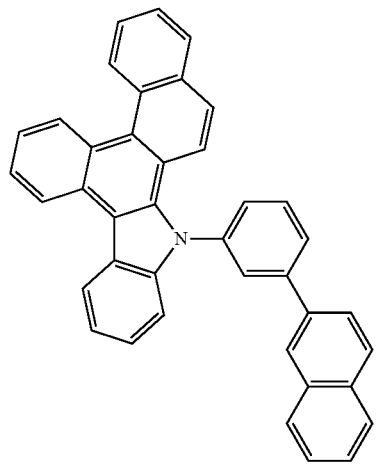
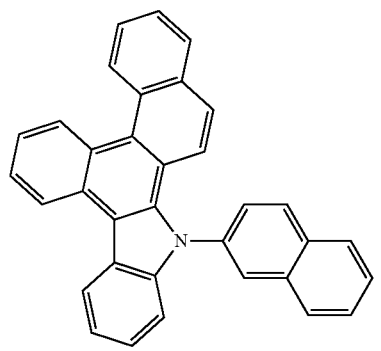
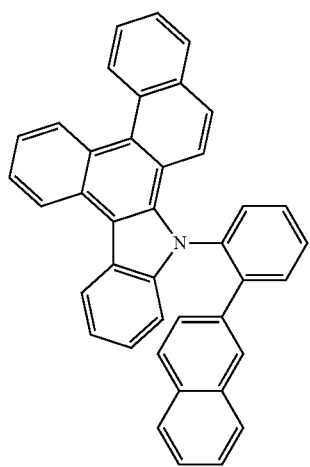
38
-continued
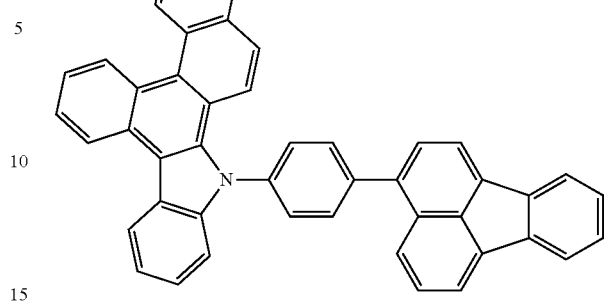
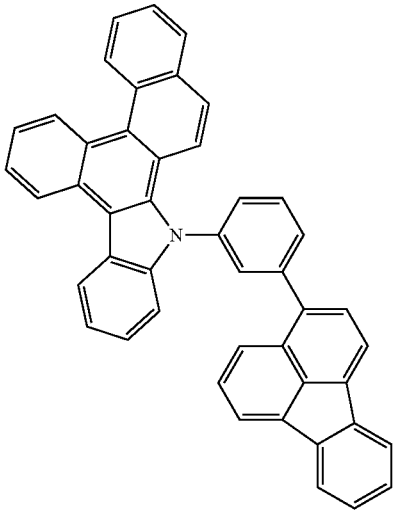
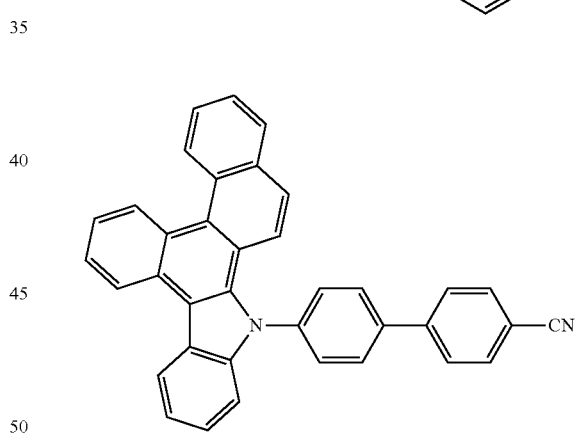
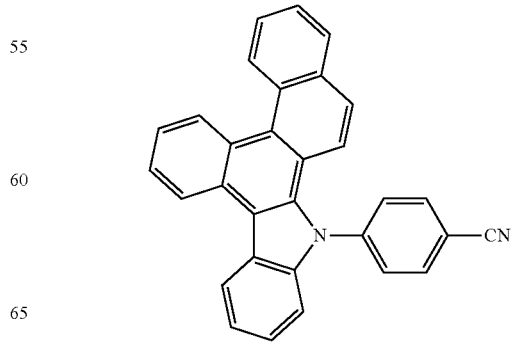

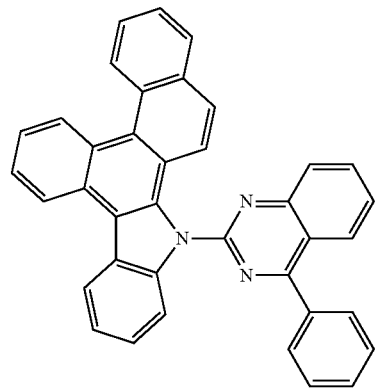
(5)
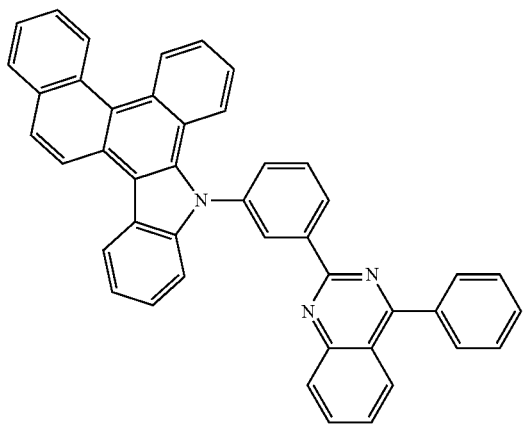
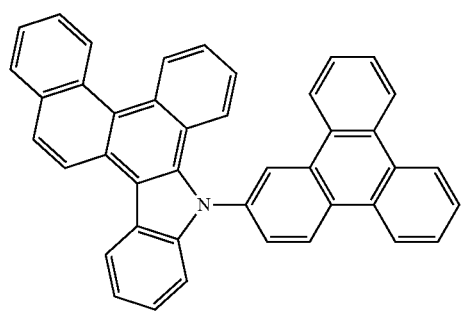
(9)
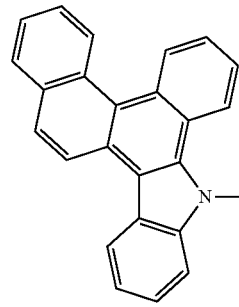
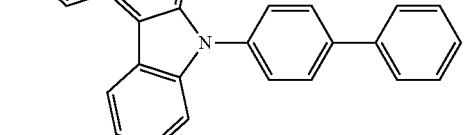
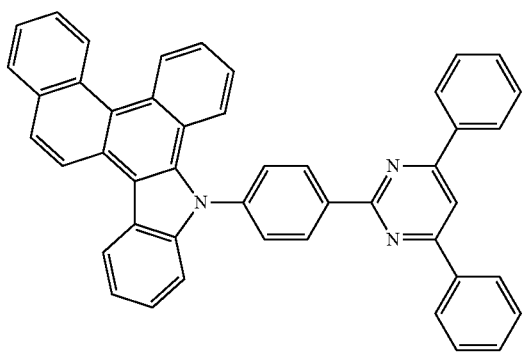
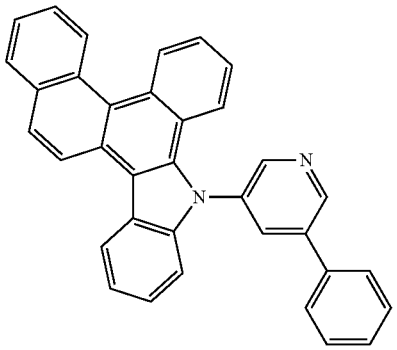
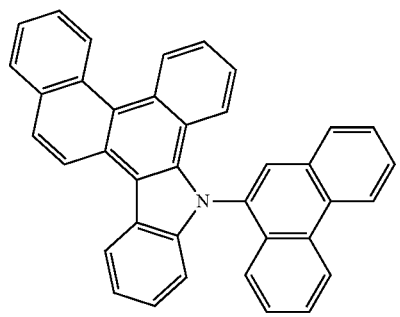
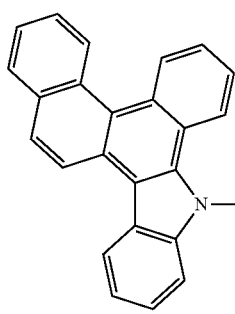
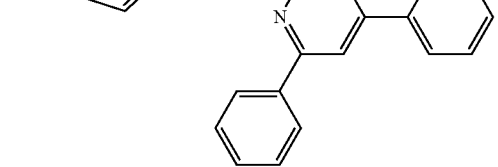

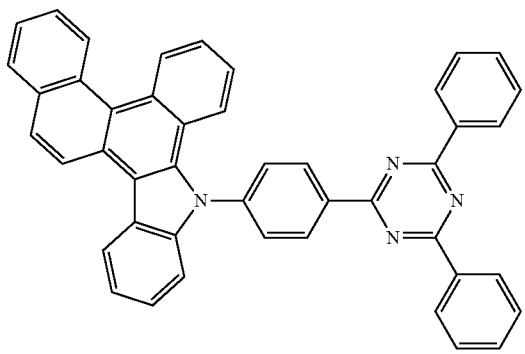
(13)
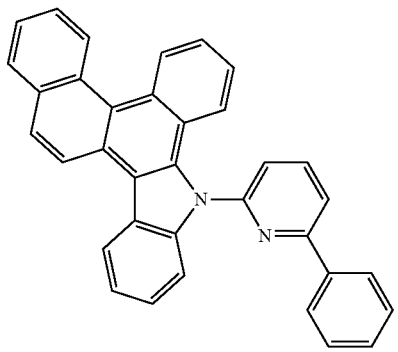
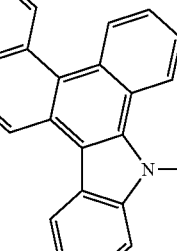
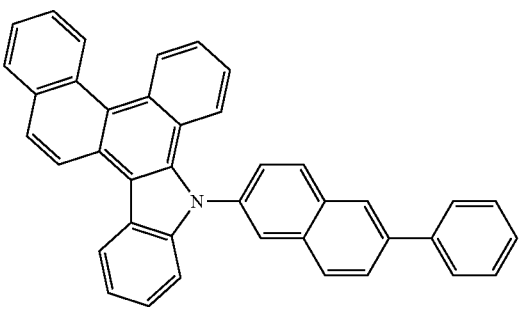
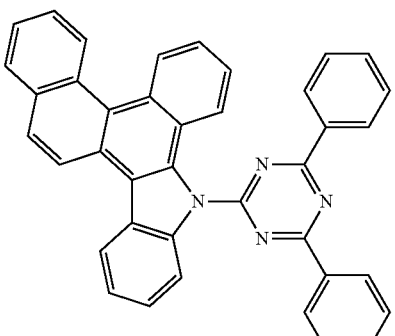
(11)
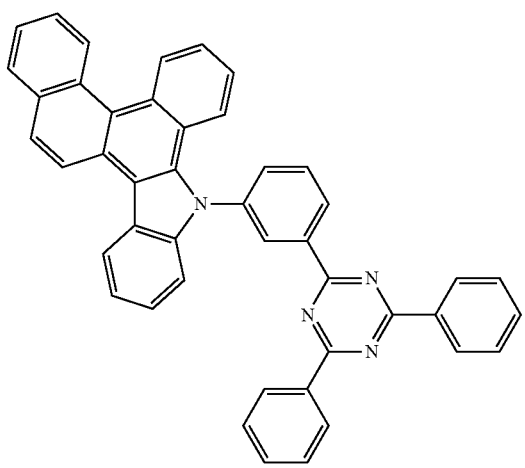
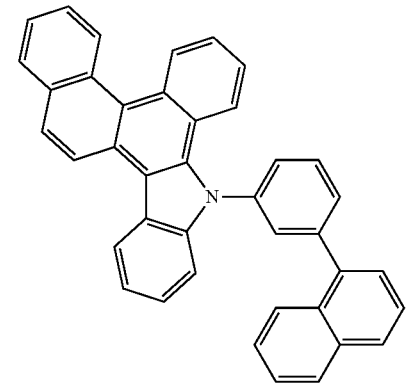
(14)
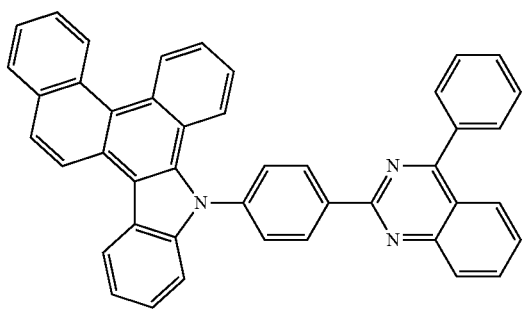
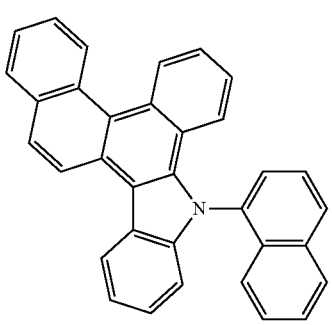

-continued
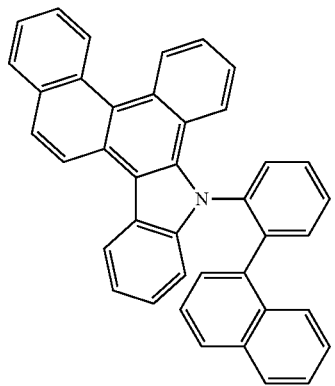
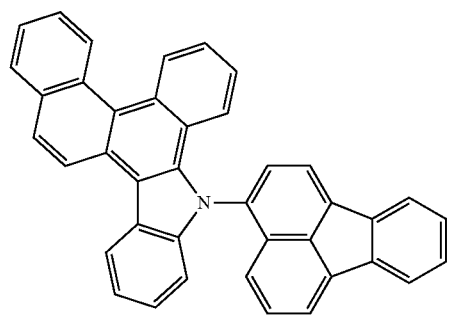
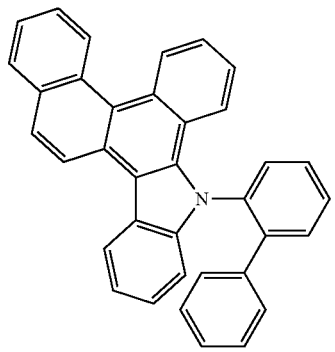
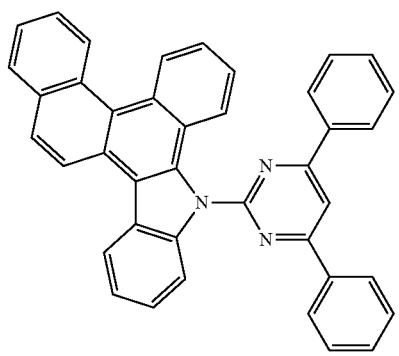
-continued
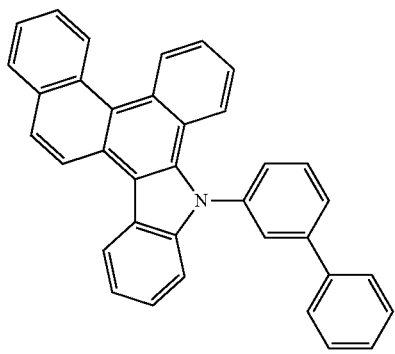
(8)
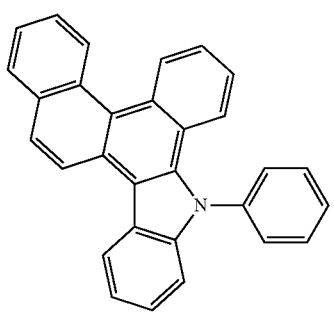
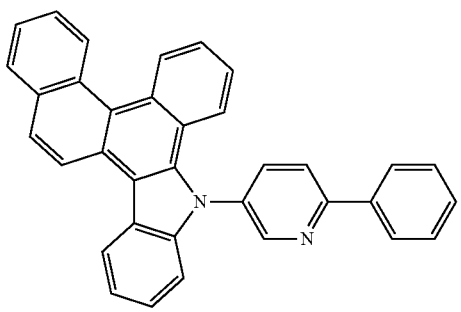
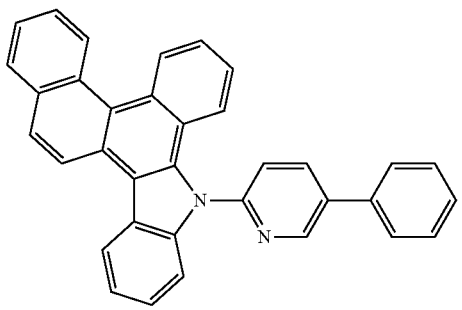
(10)
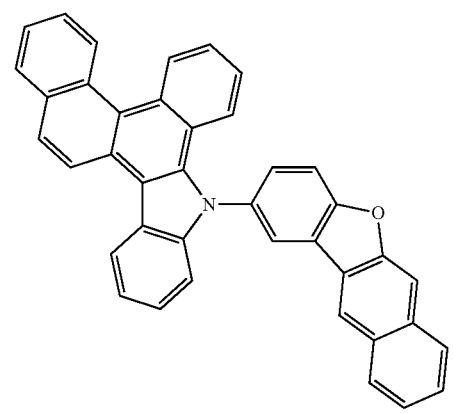

45
-continued
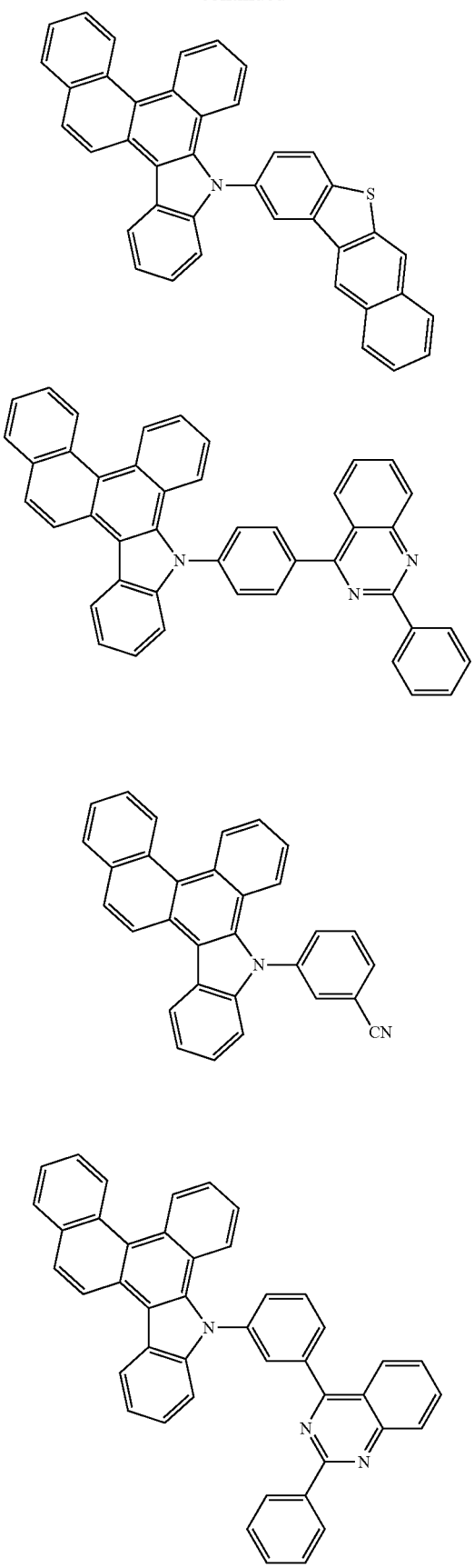
46
-continued
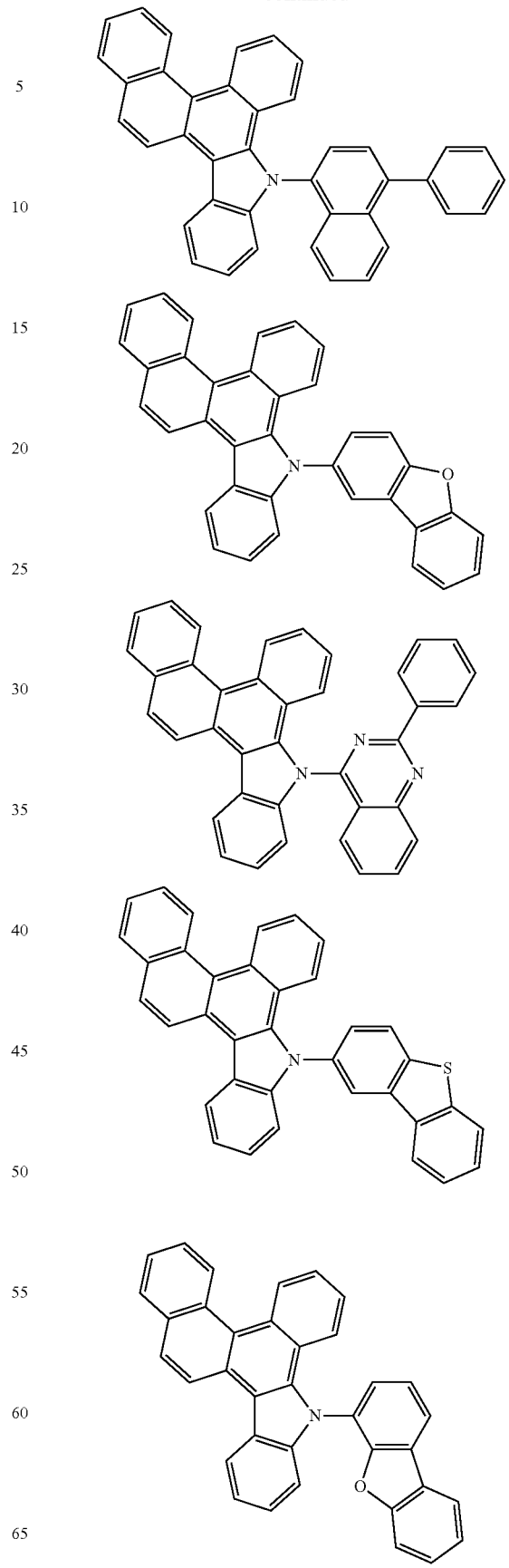

47
-continued
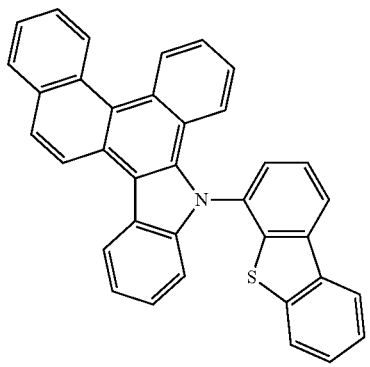
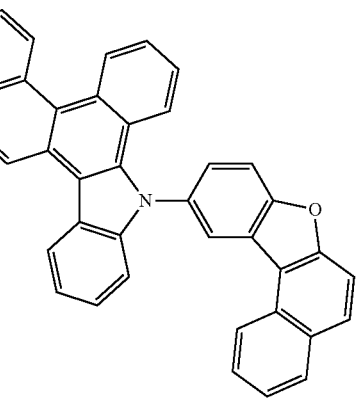
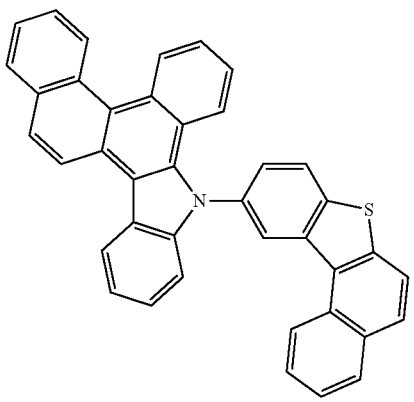
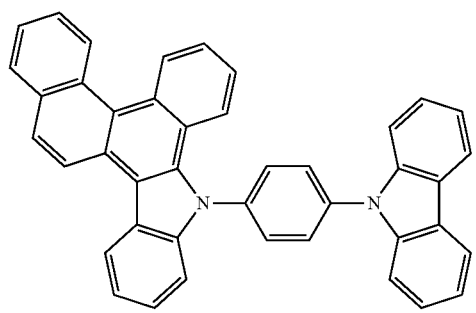
48
-continued
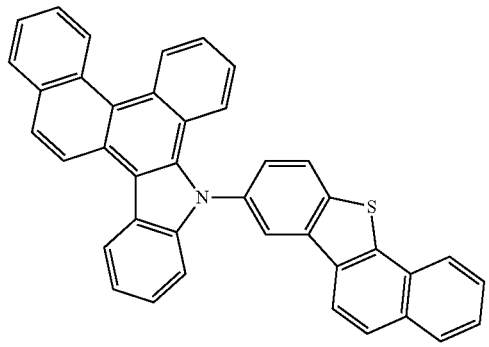
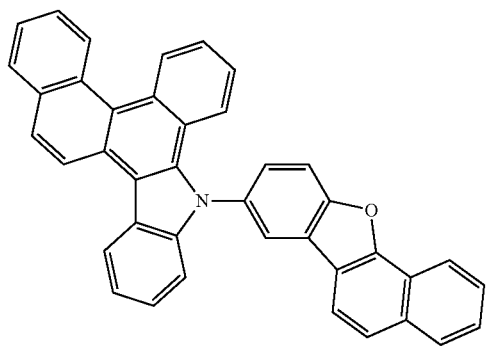
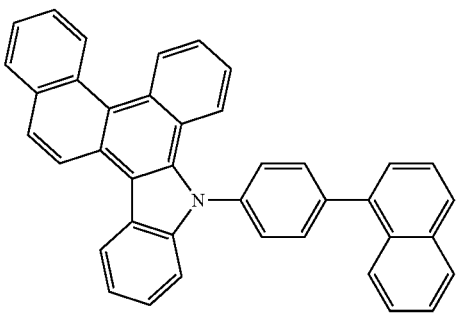
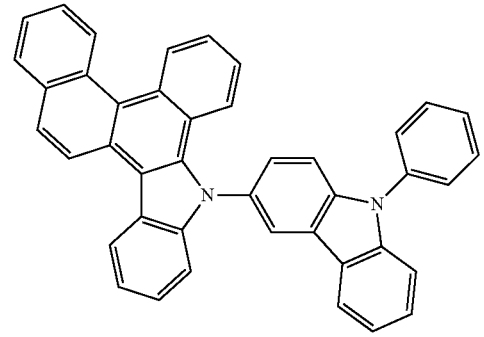
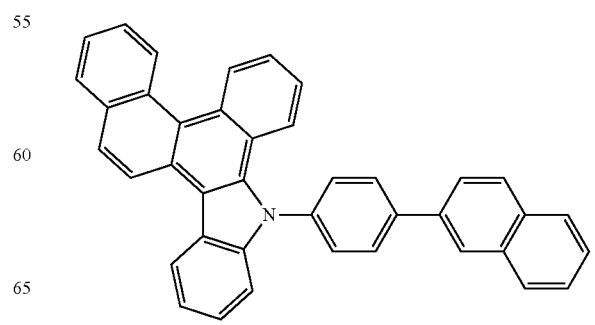

49
-continued
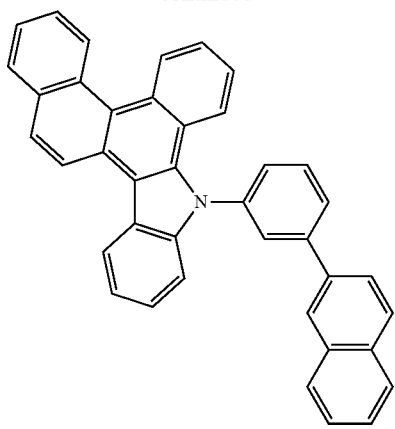
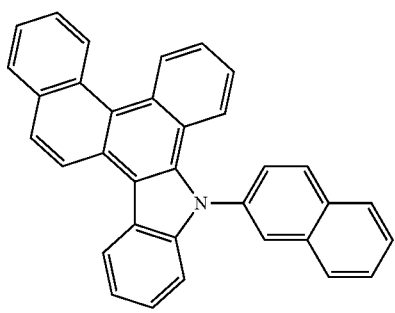
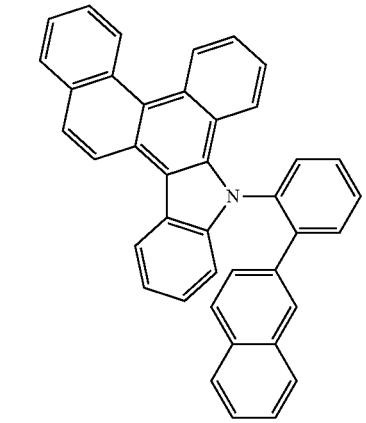
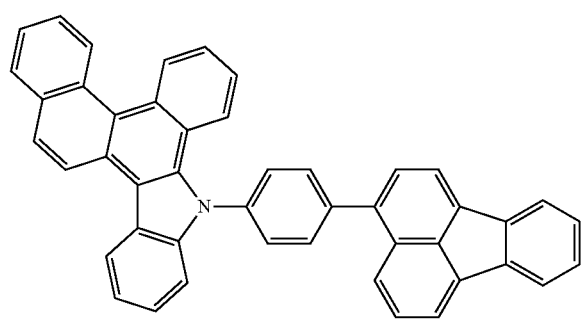
50
-continued
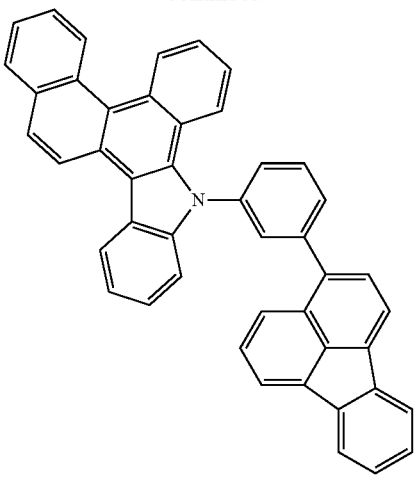
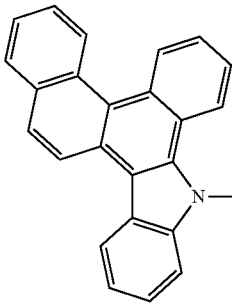
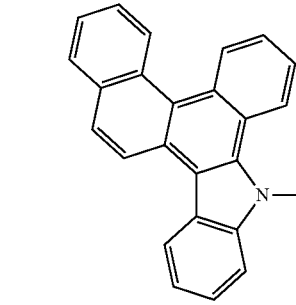
(12)
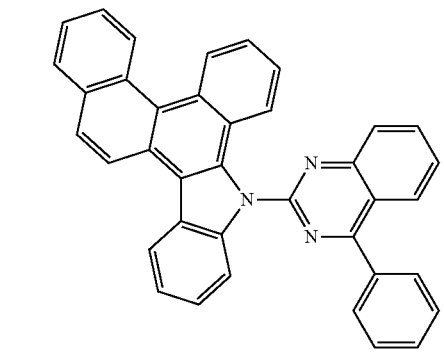

51
-continued
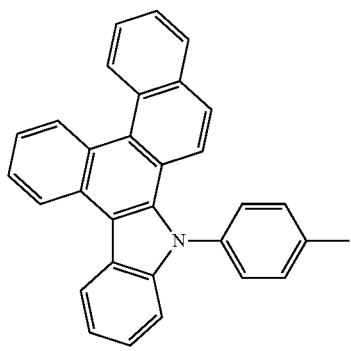
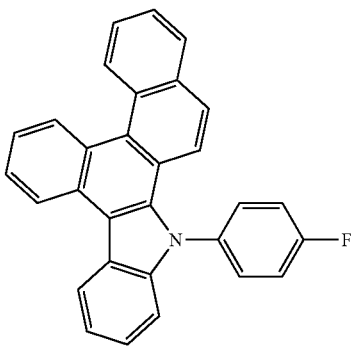
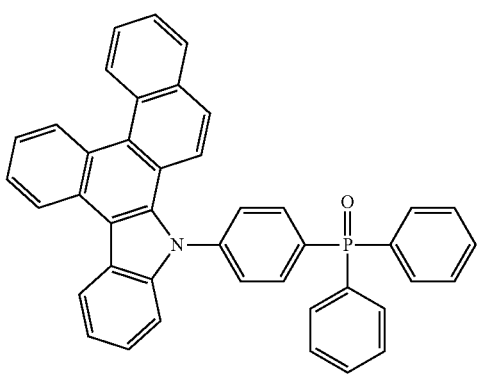
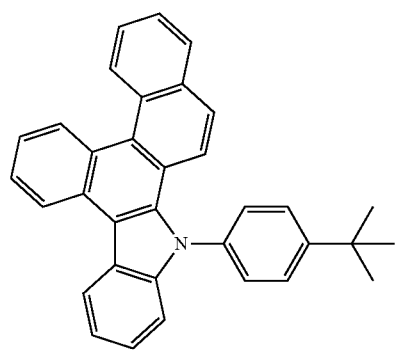
52
-continued
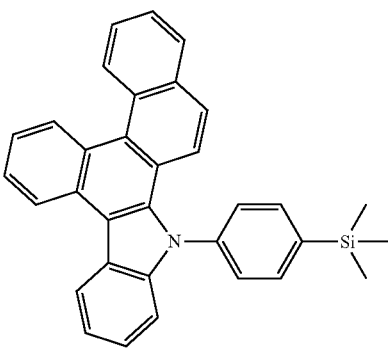
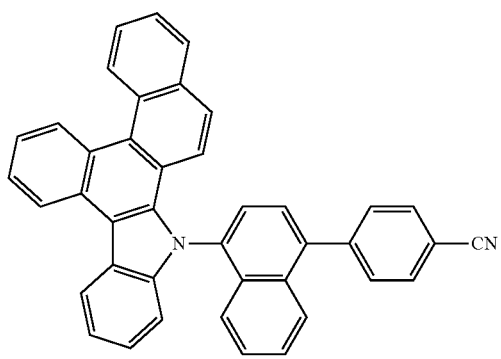
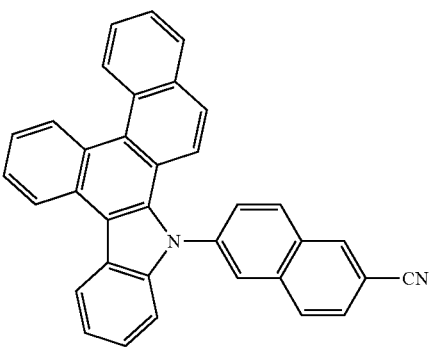
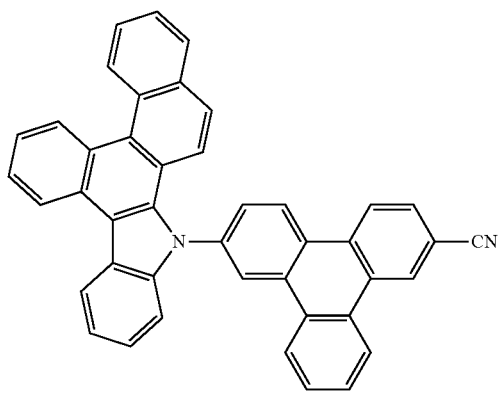

53
-continued
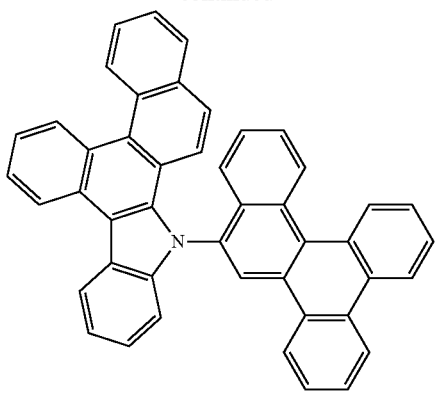
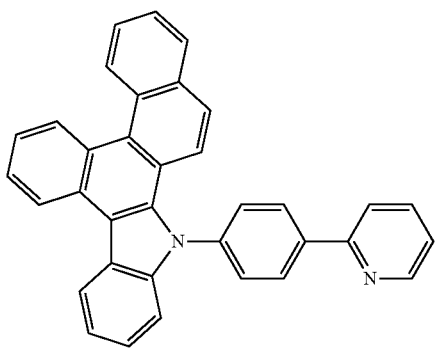
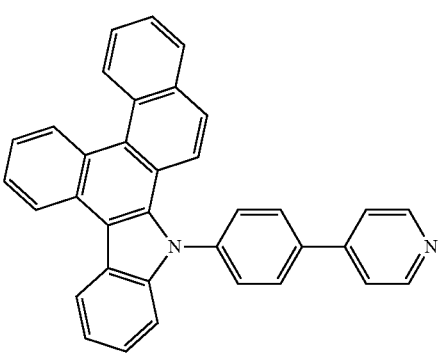
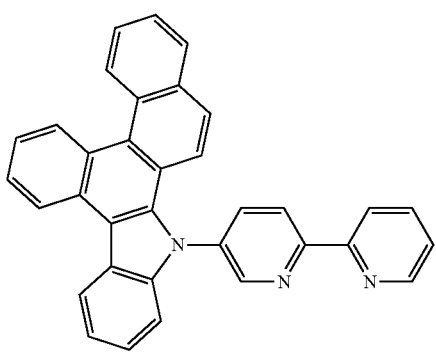
54
-continued
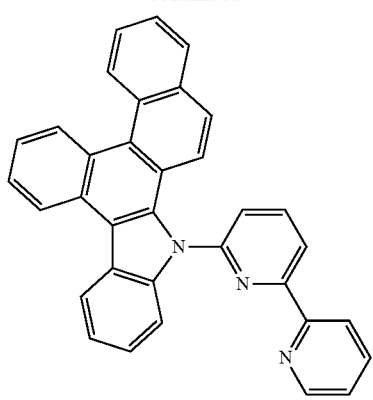
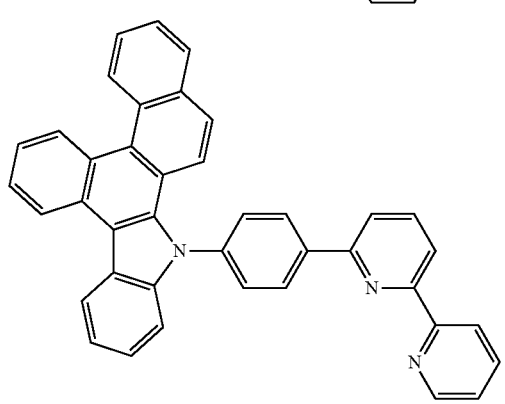
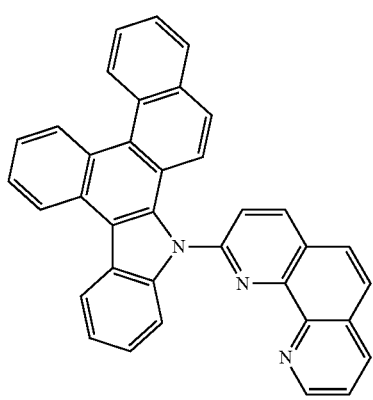
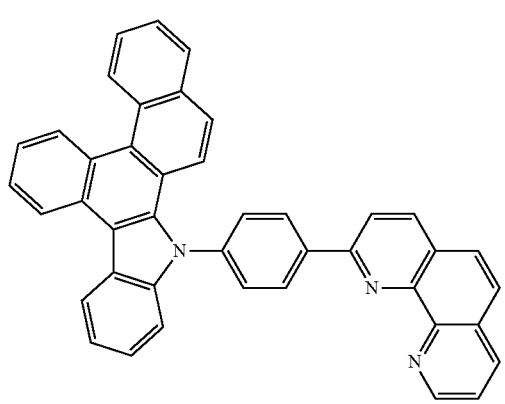

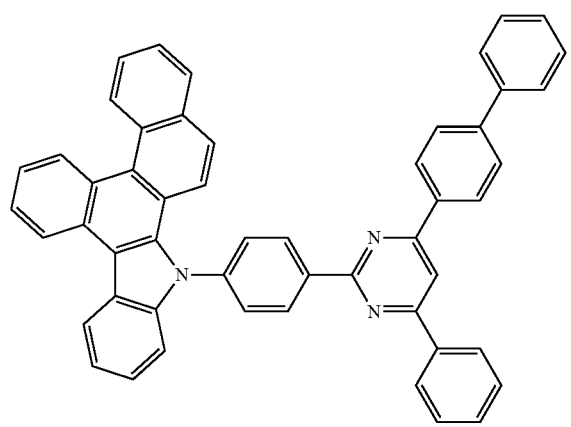
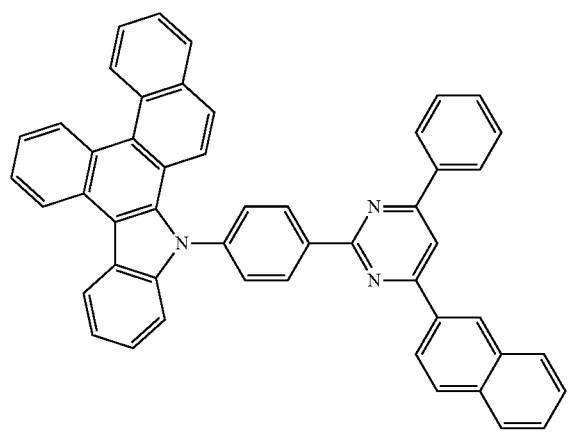
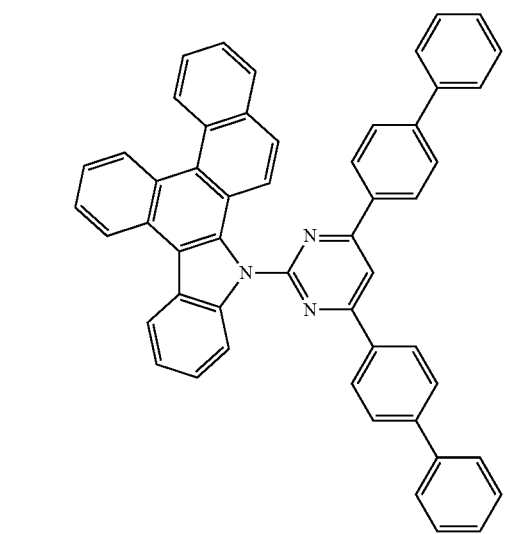
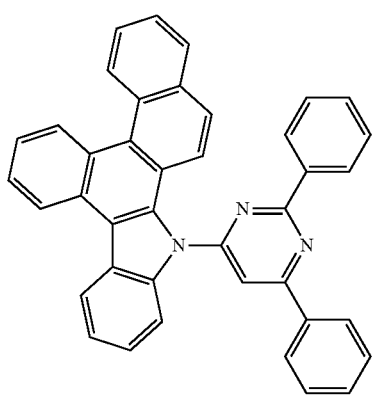
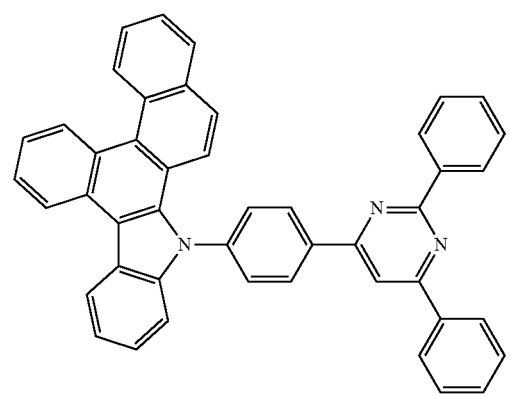
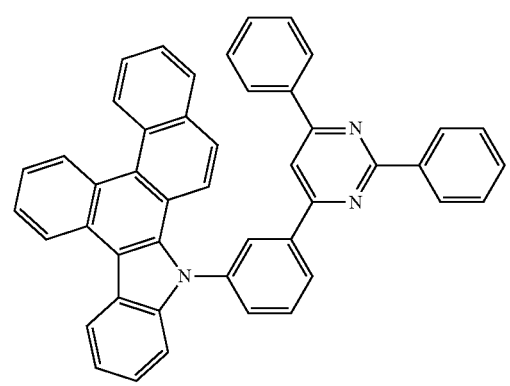
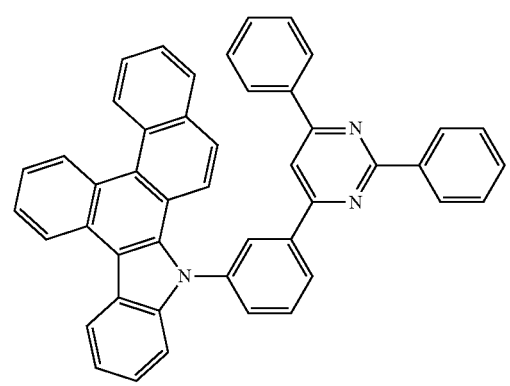
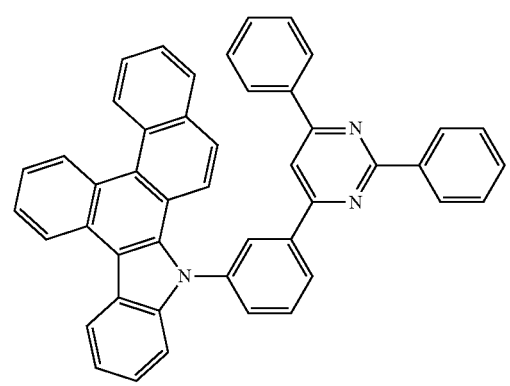

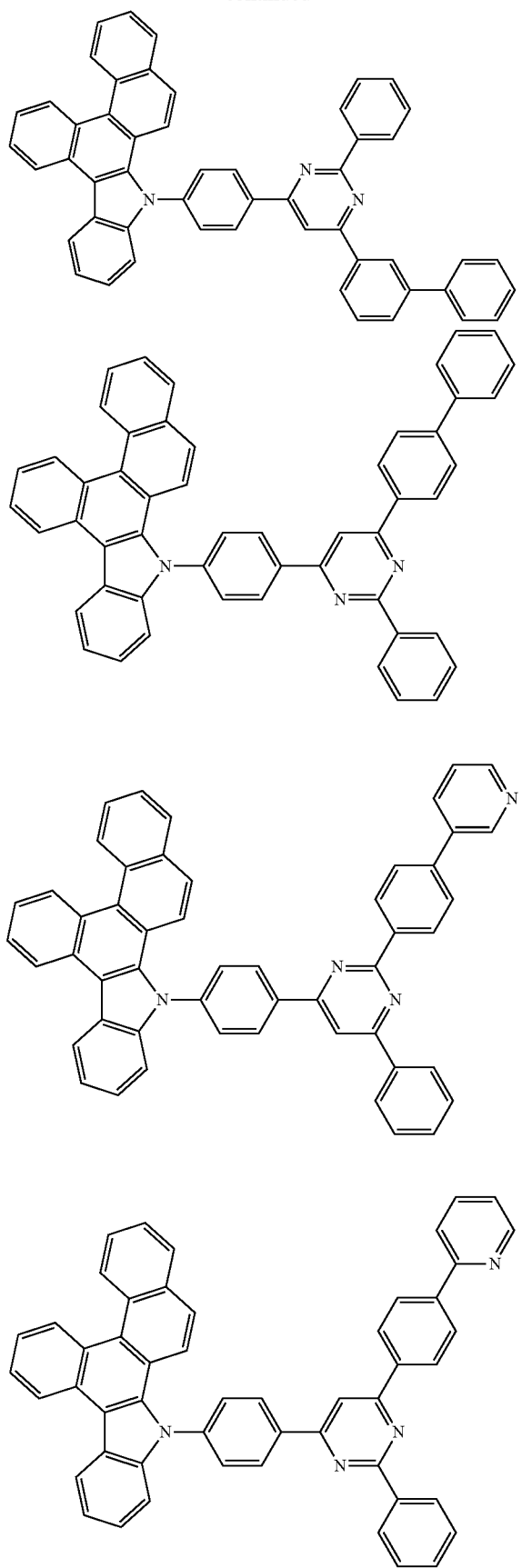
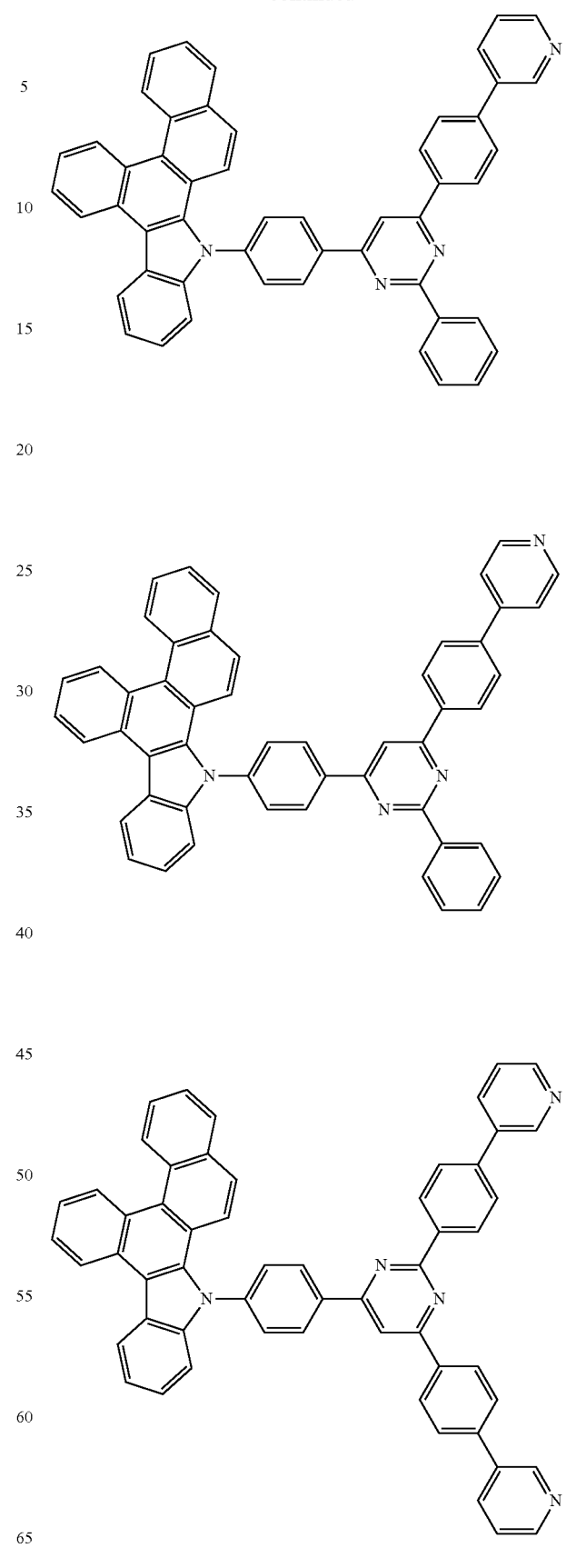

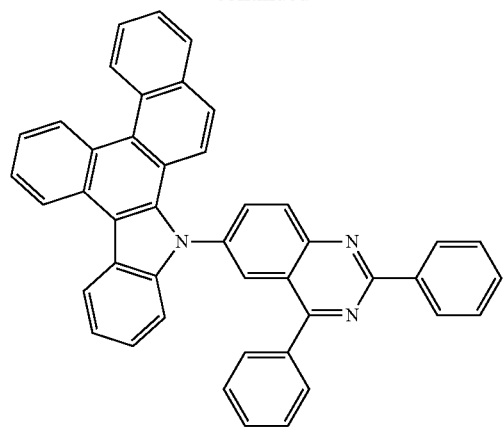
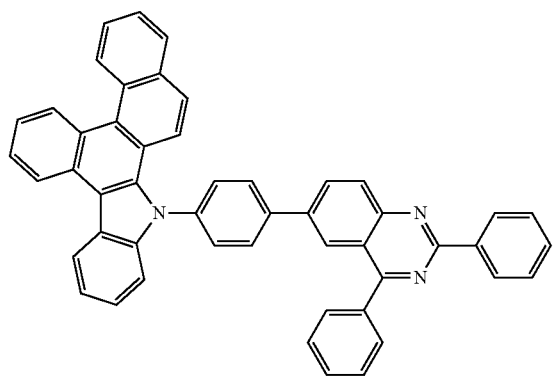
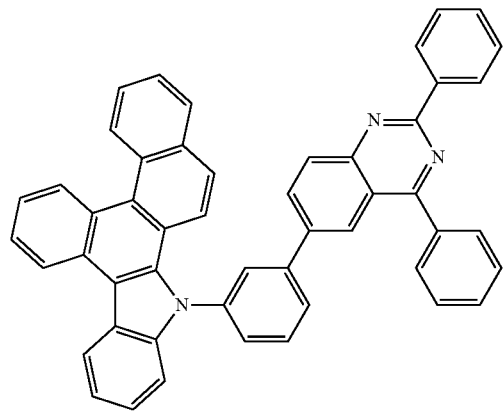
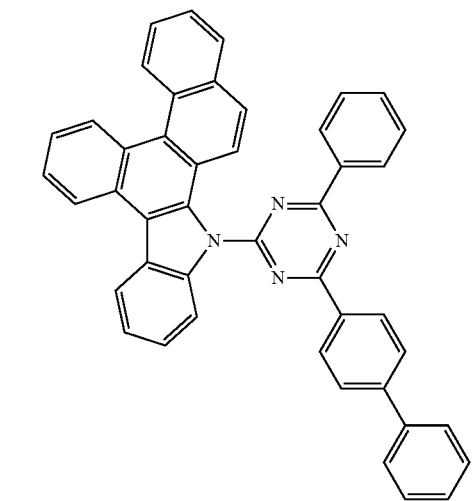
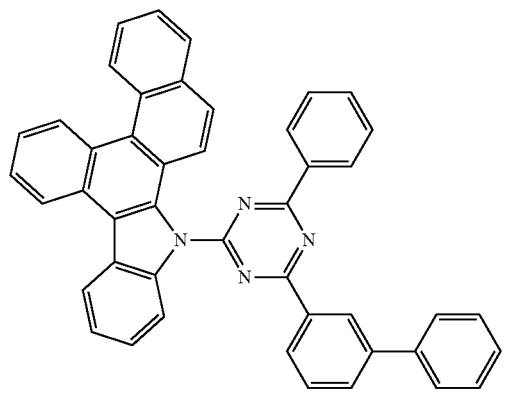
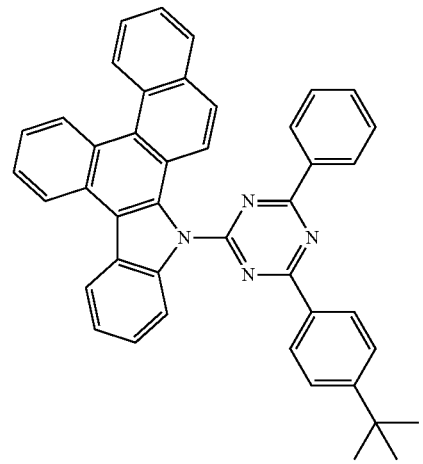
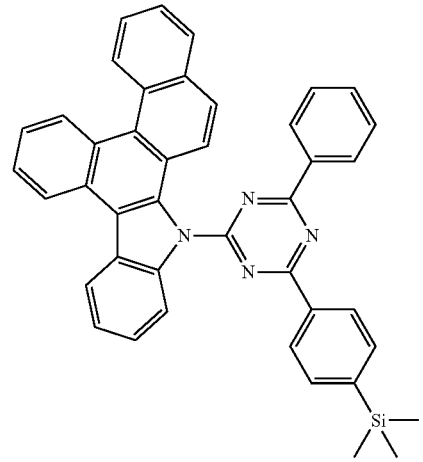

-continued
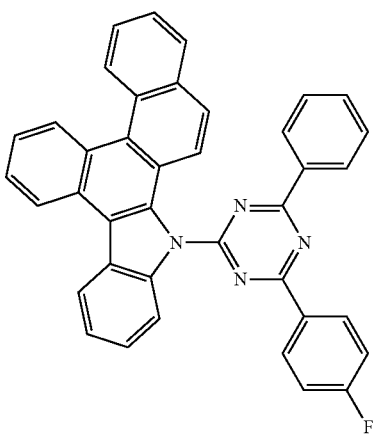
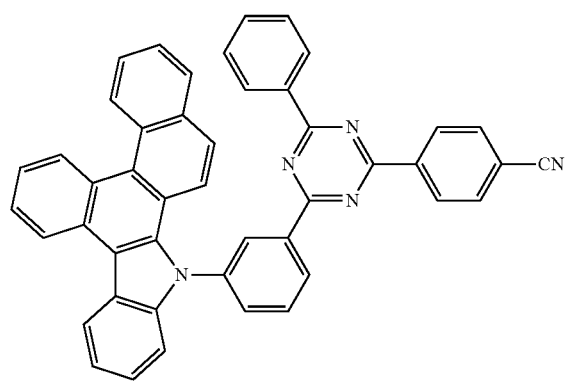
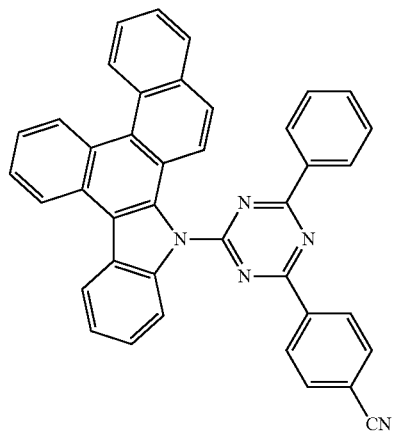
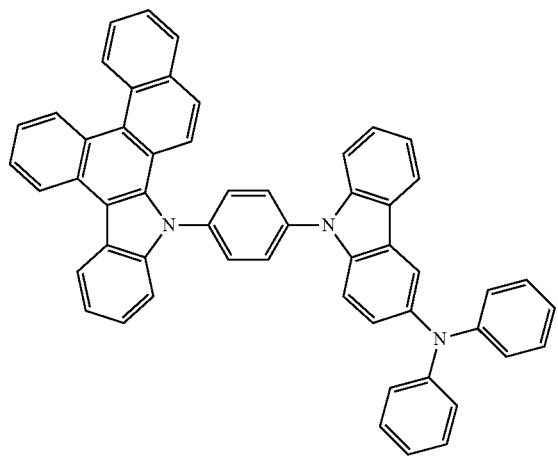
-continued
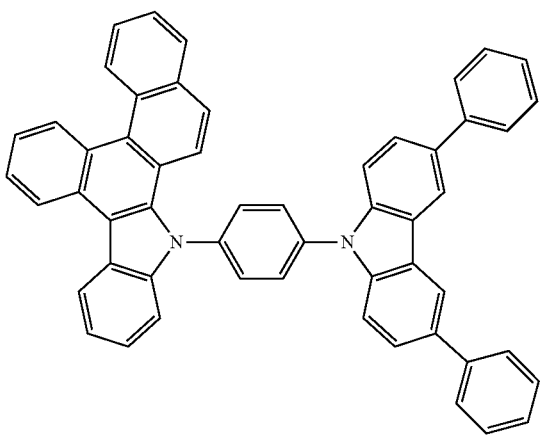
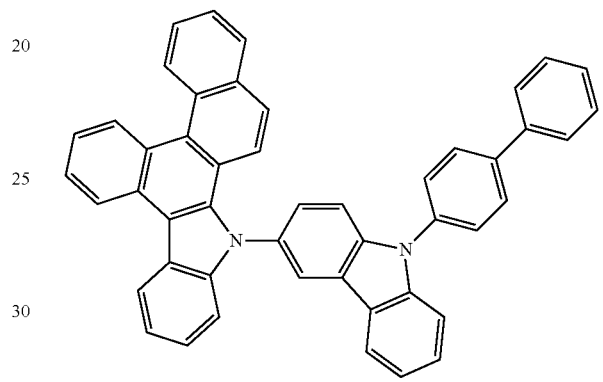
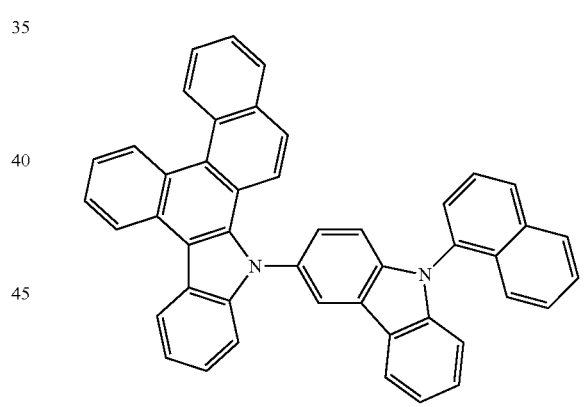
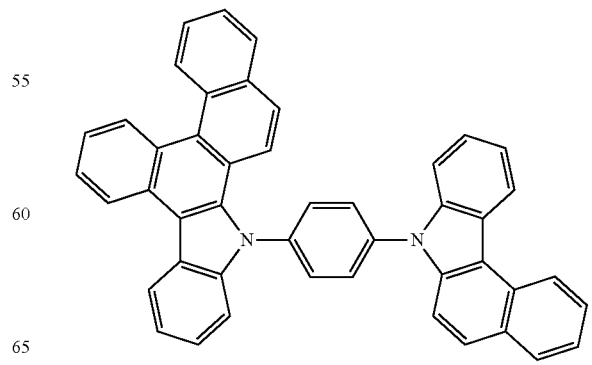

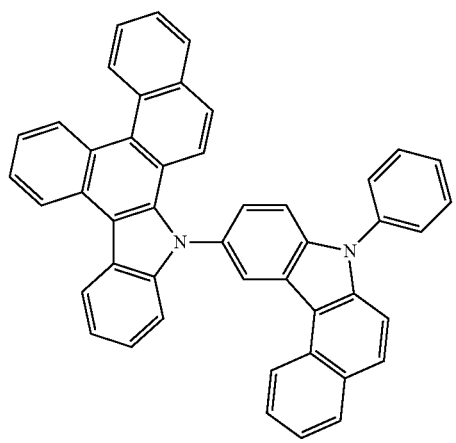
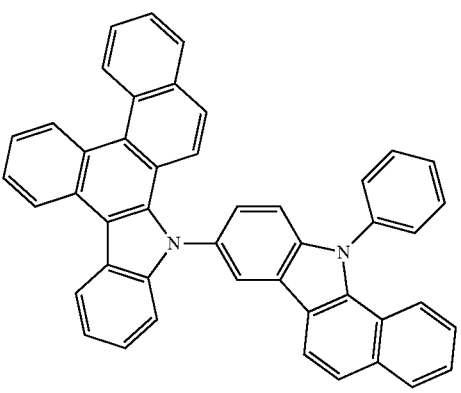
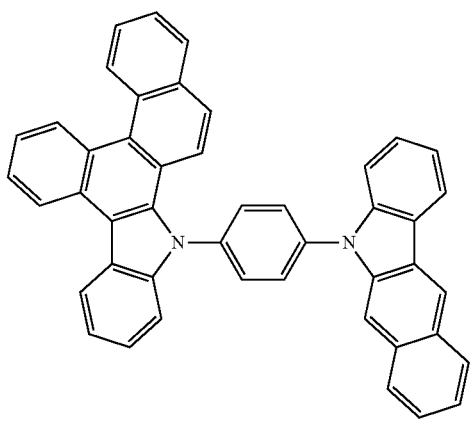
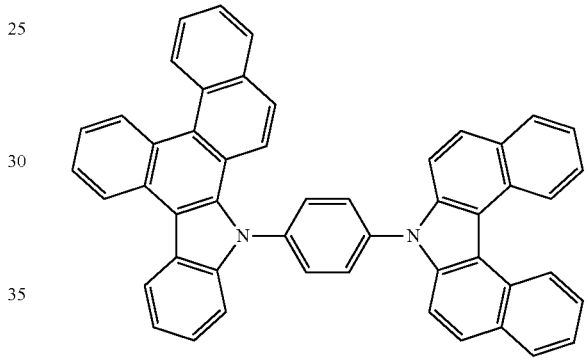
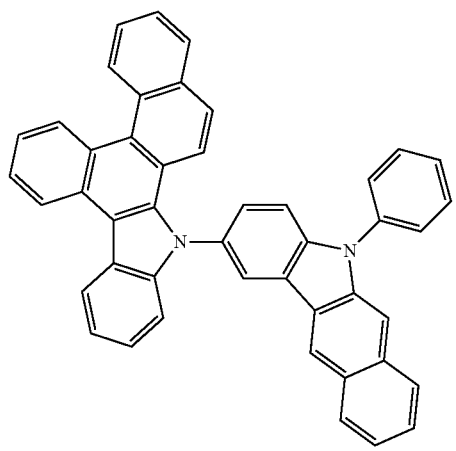
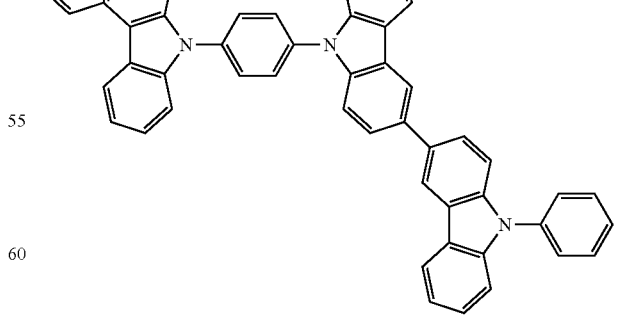

65
-continued
66
-continued
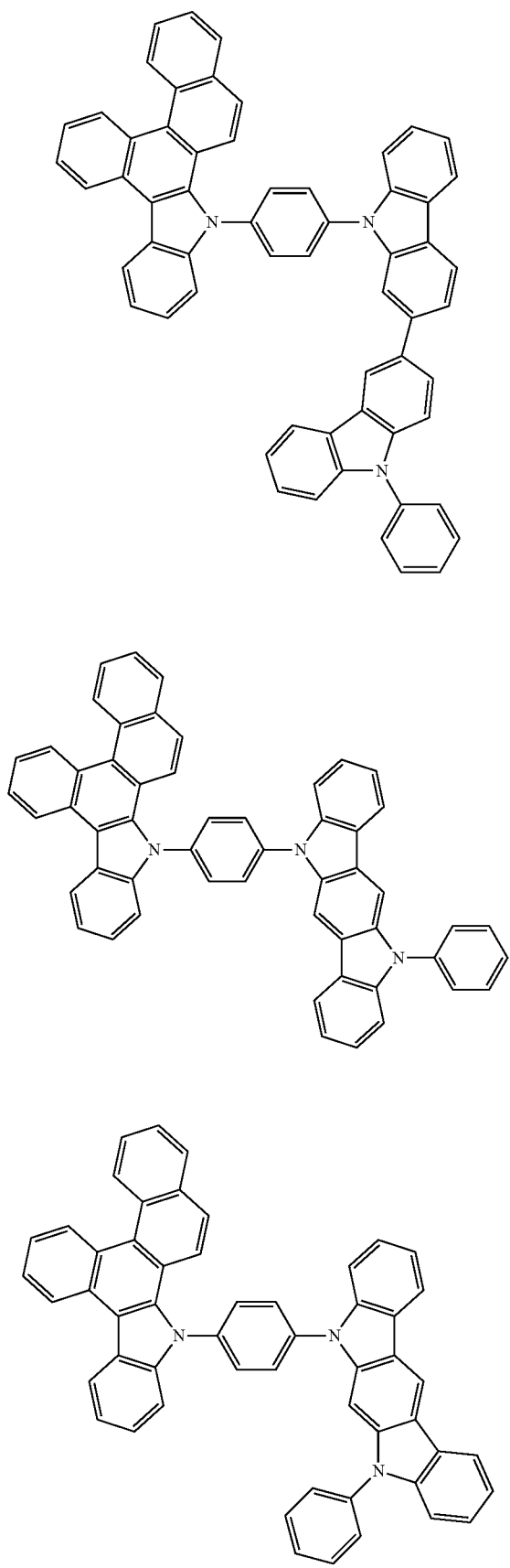
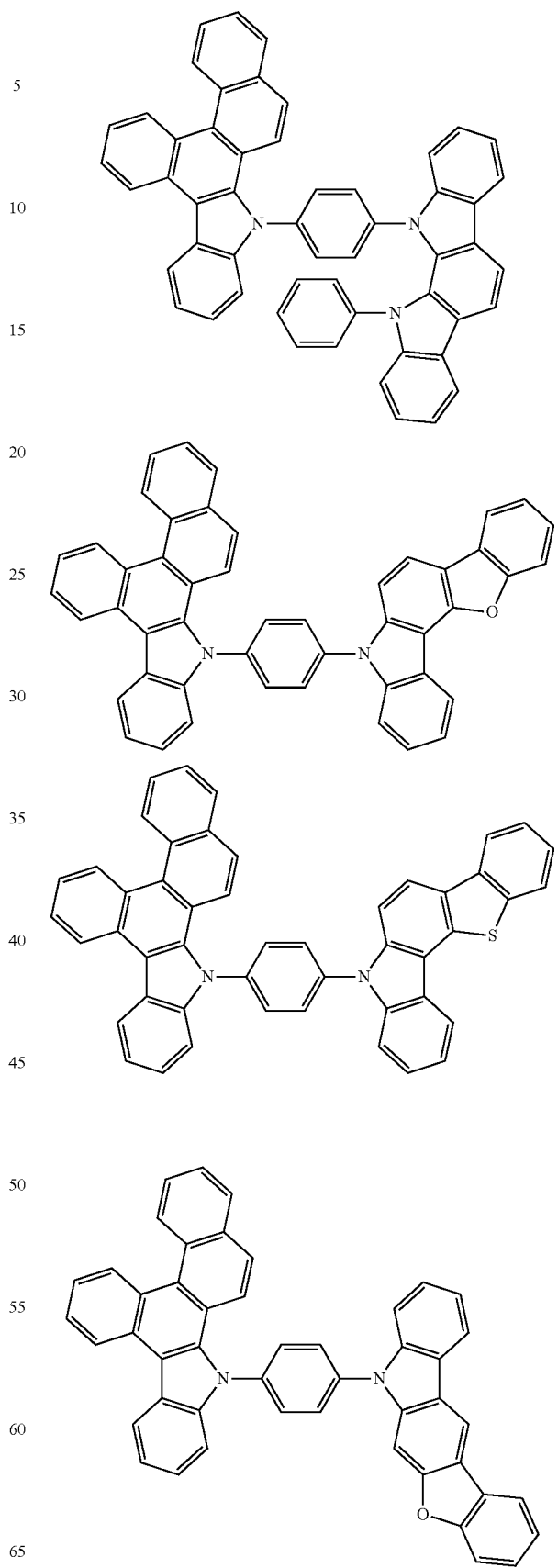

US 9,837,615 B2
67
-continued
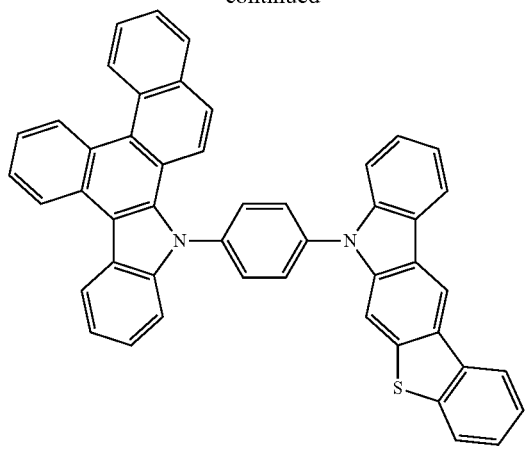
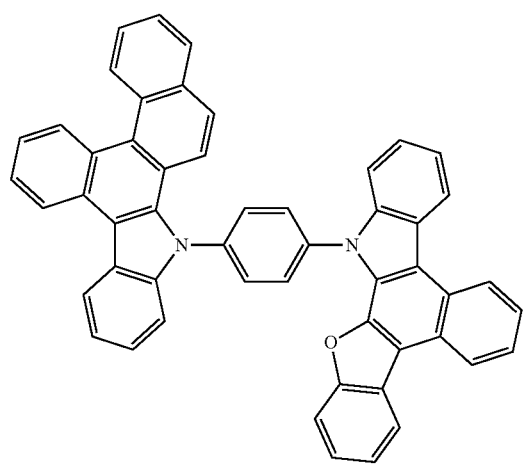
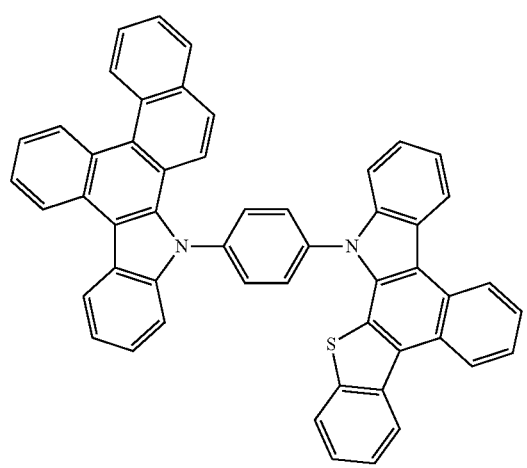
68
-continued
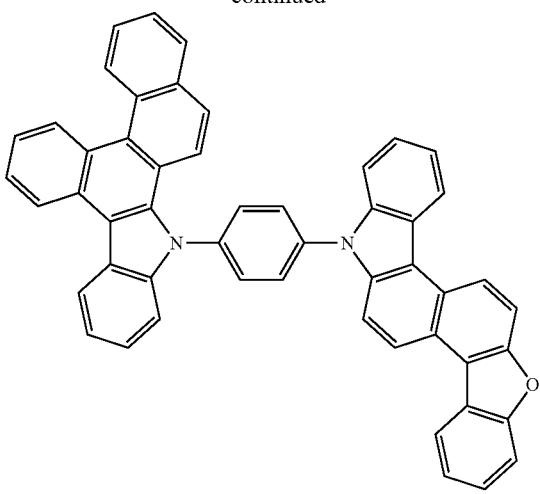
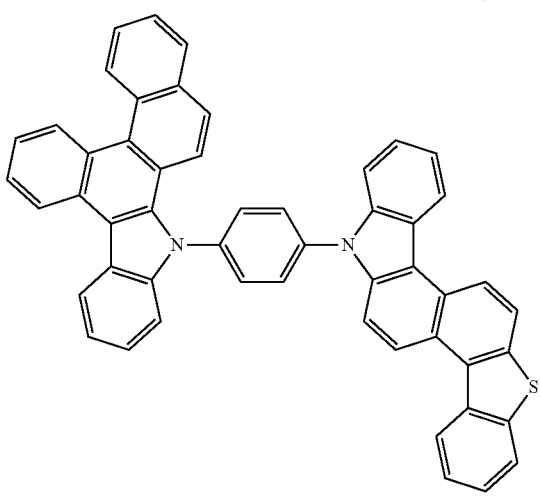
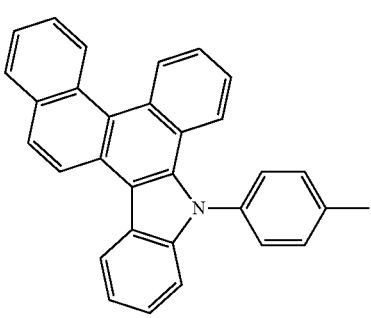
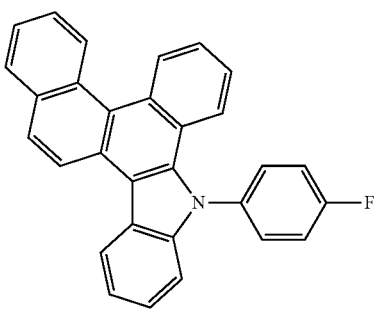

69
-continued
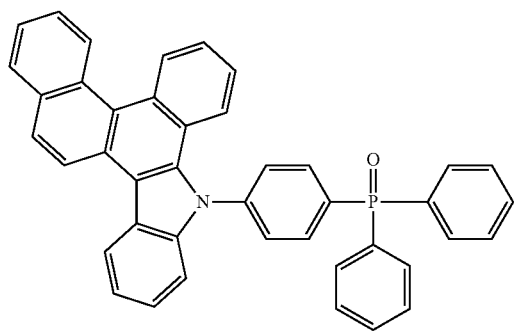
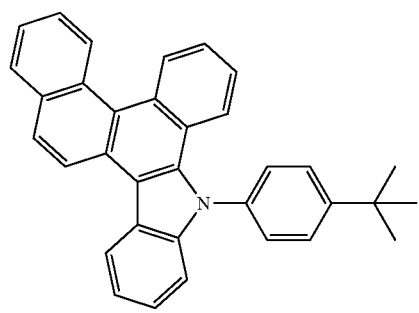
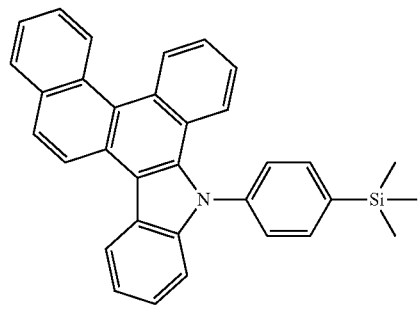
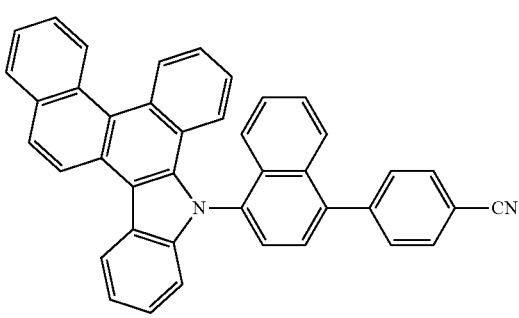
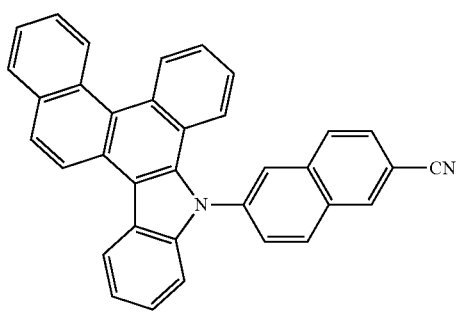
70
-continued
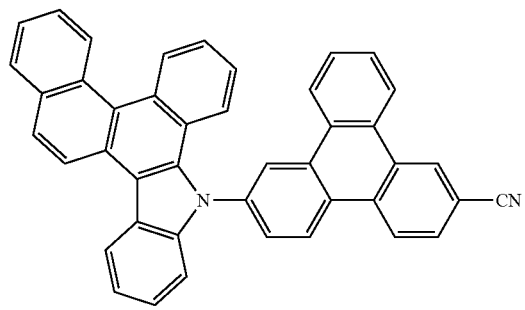
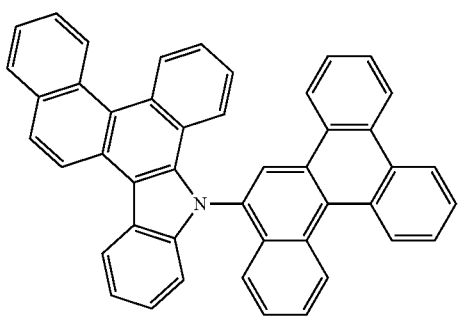
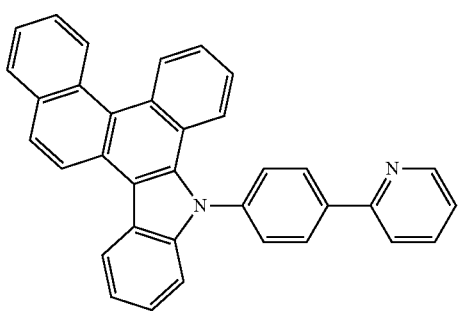
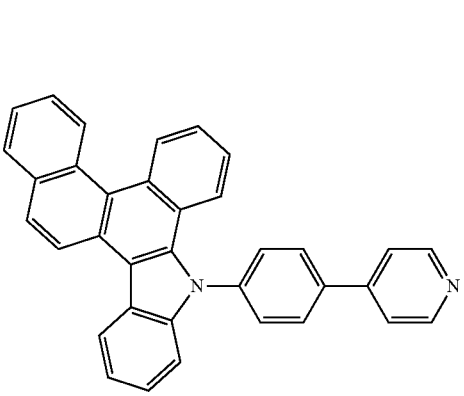
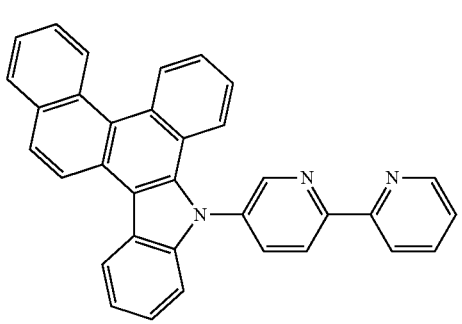

71
-continued
72
-continued
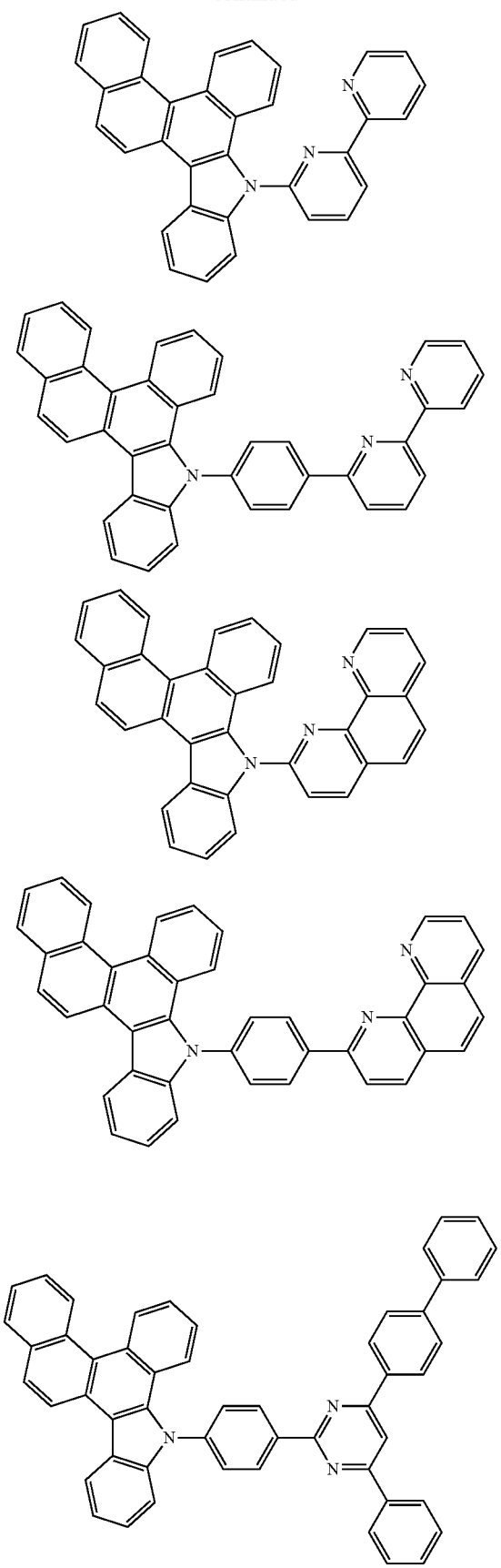
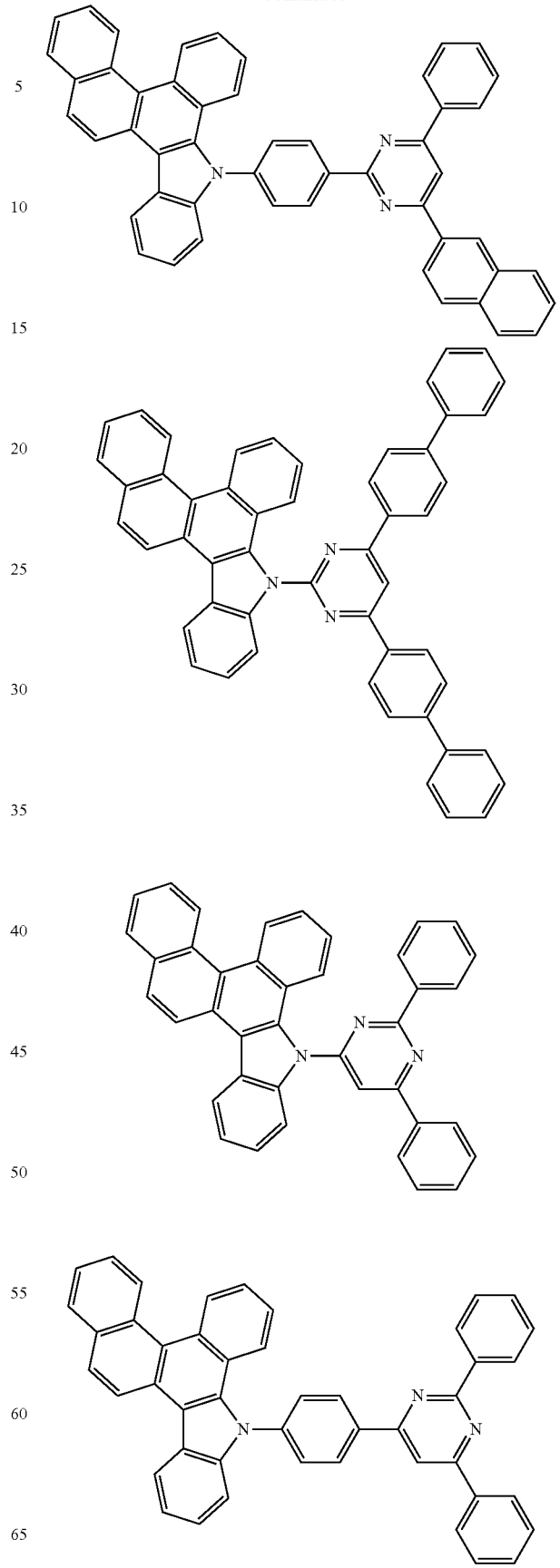

73
-continued
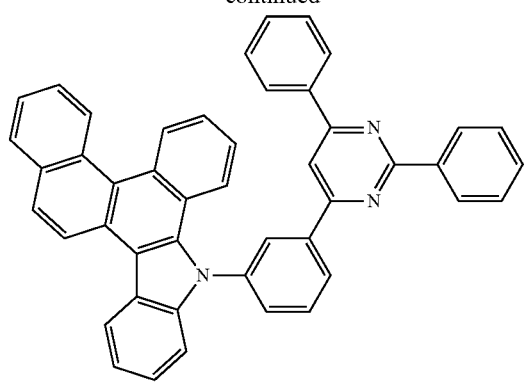
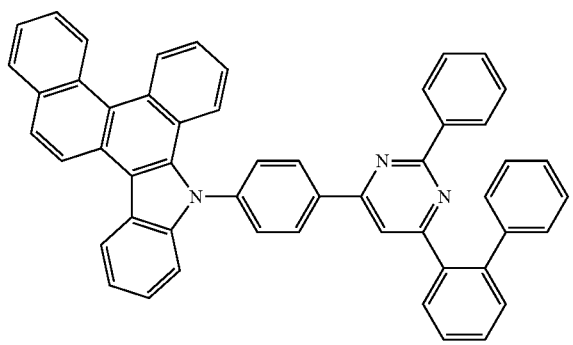
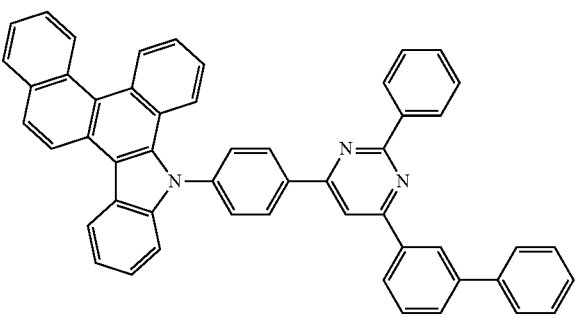
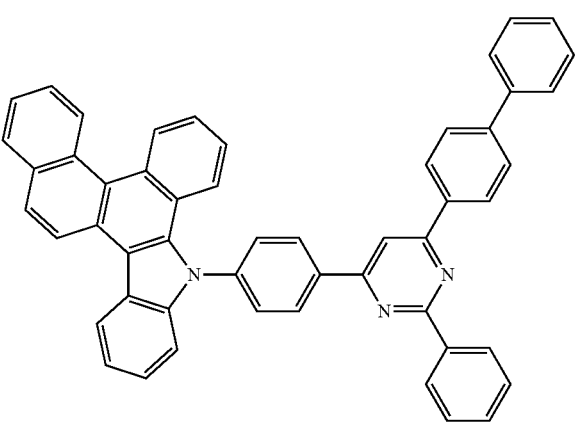
74
-continued
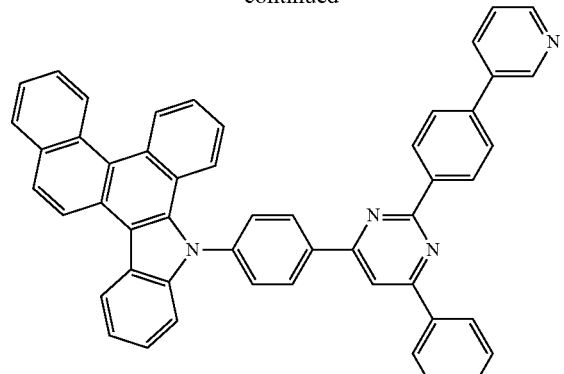
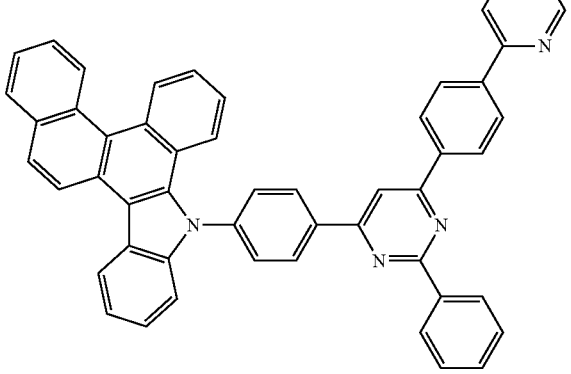
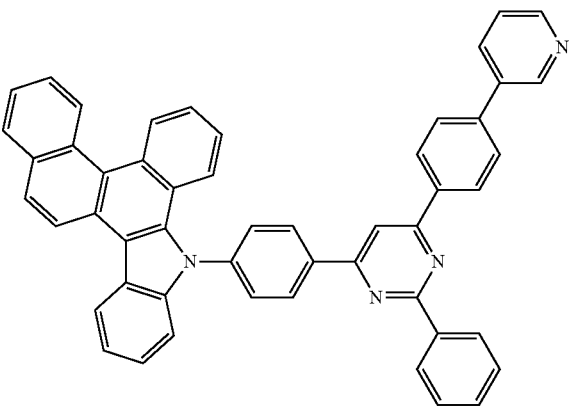
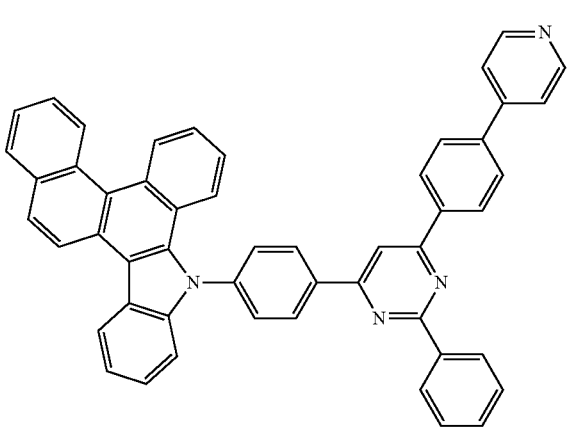

75
-continued
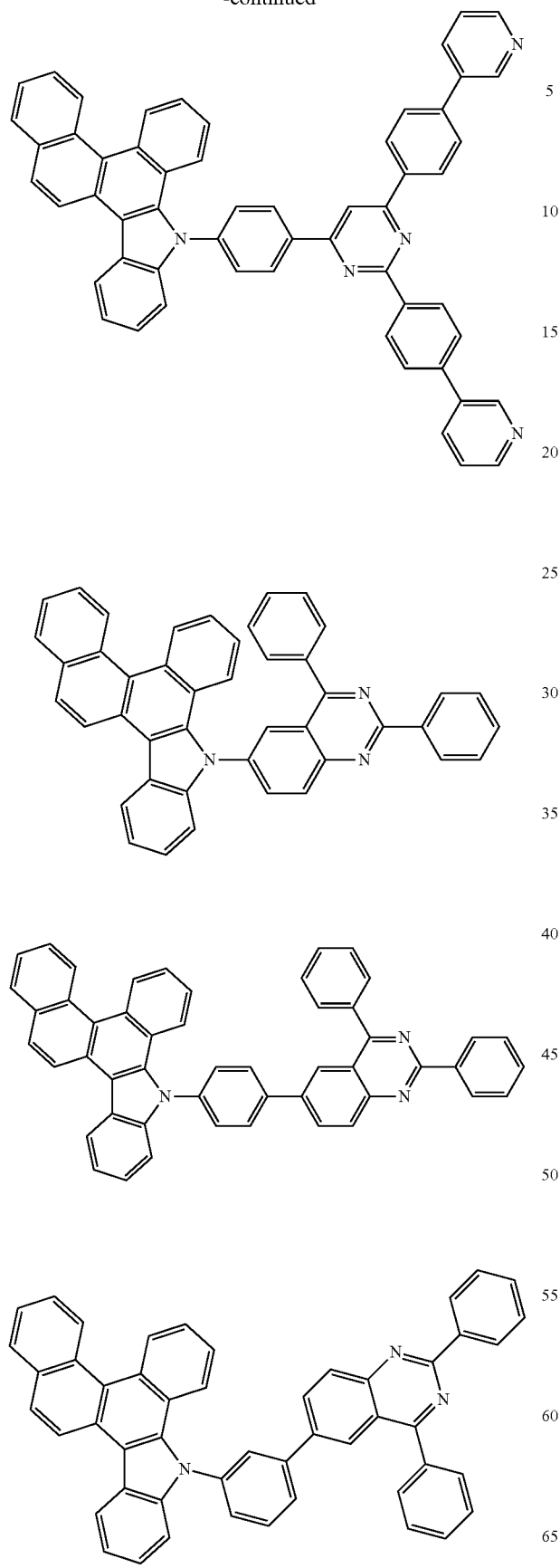
76
-continued
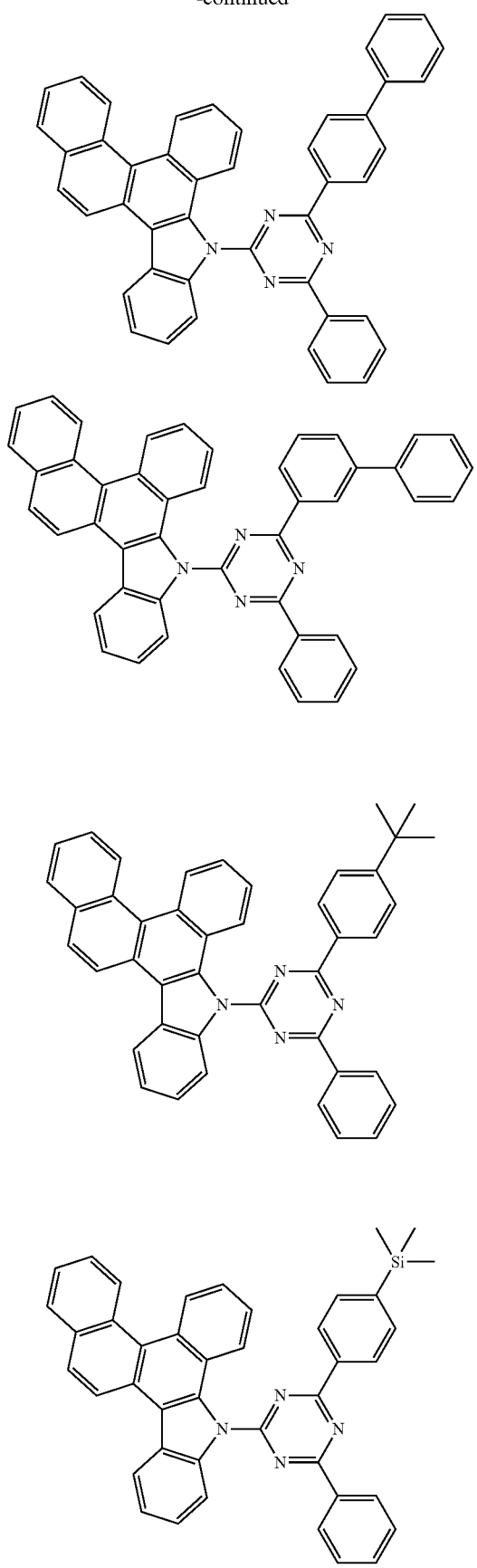

77
-continued
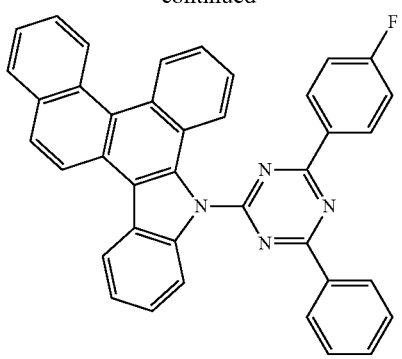
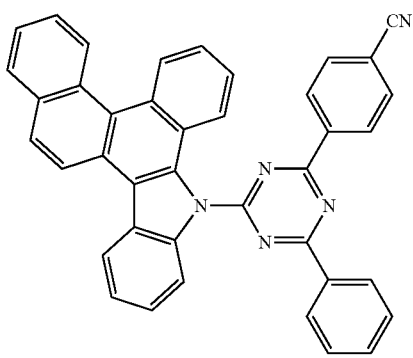
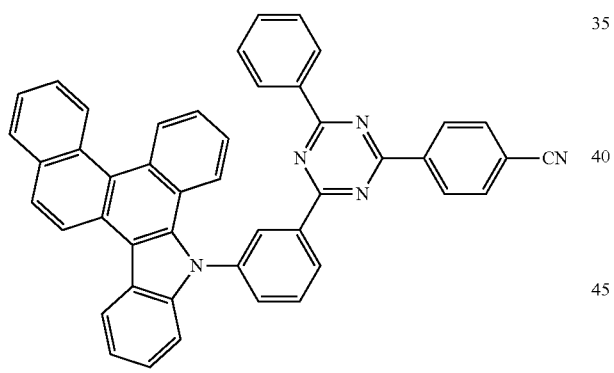
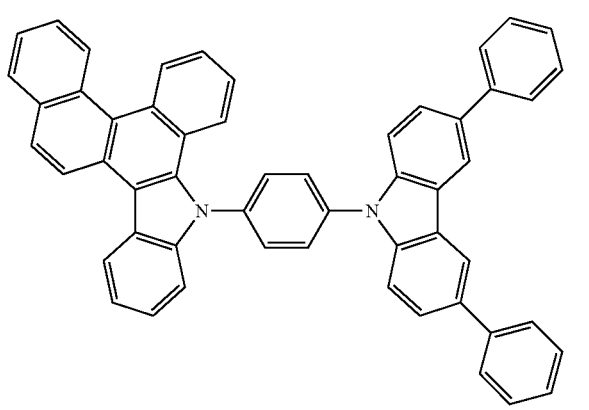
78
-continued
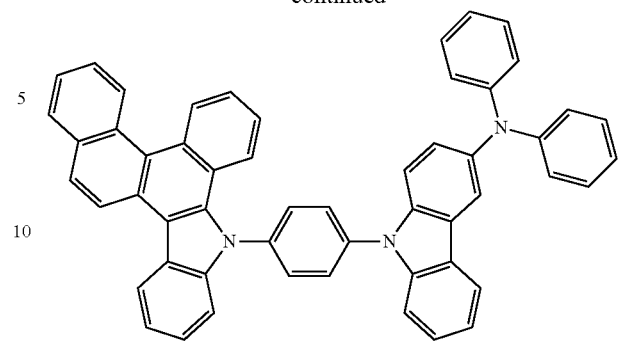
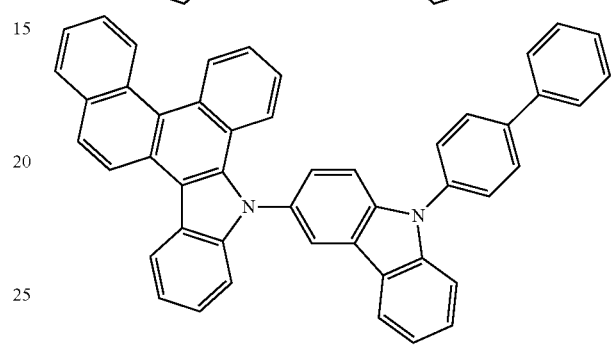
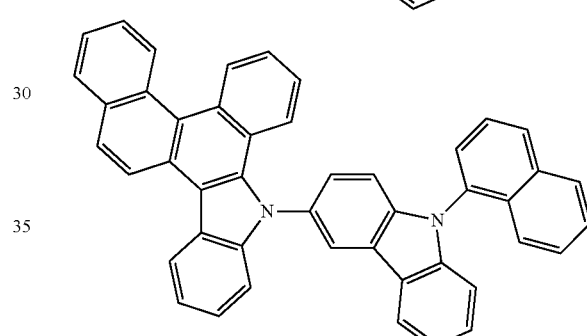
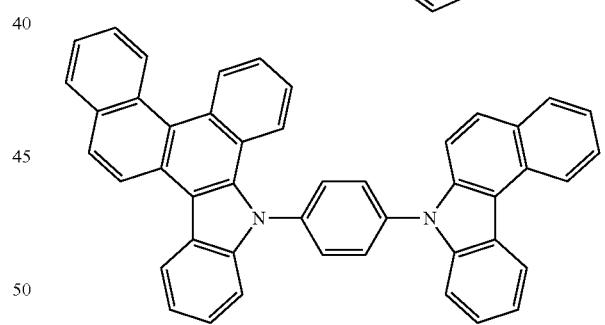
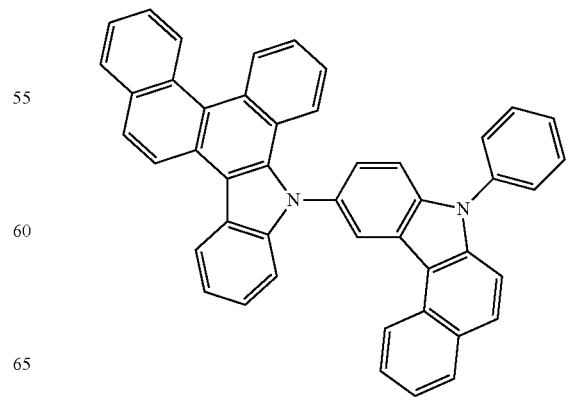

79
-continued
80
-continued
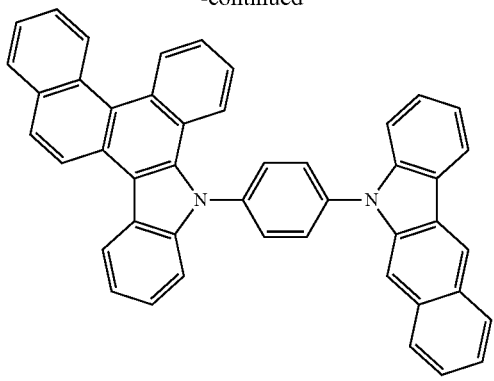
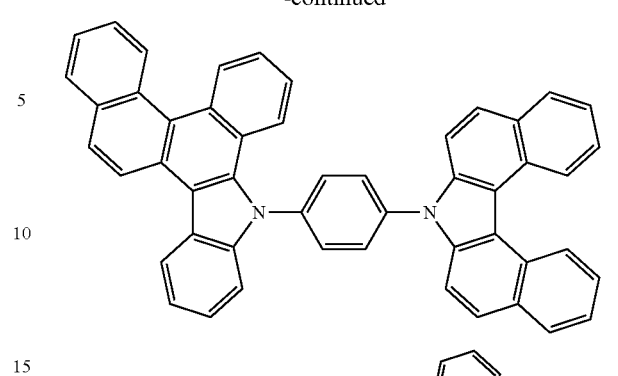
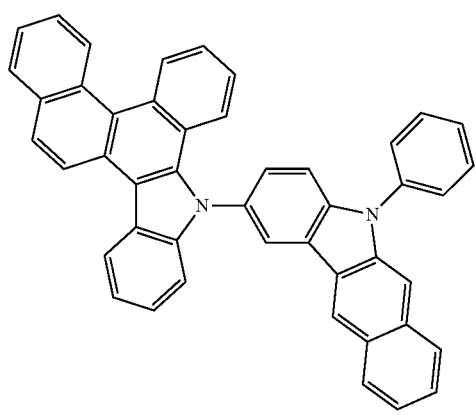
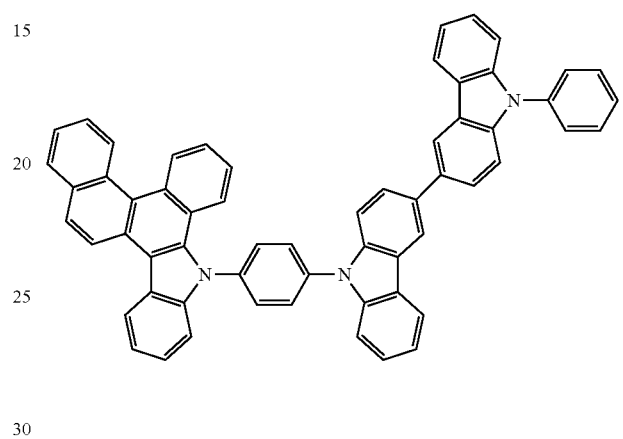
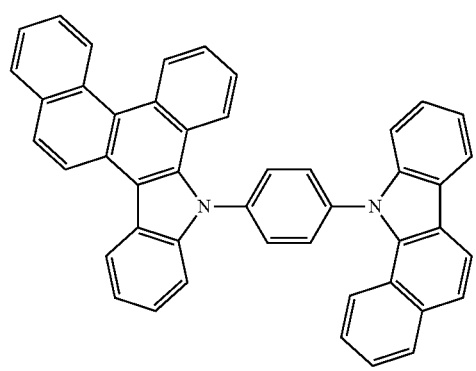
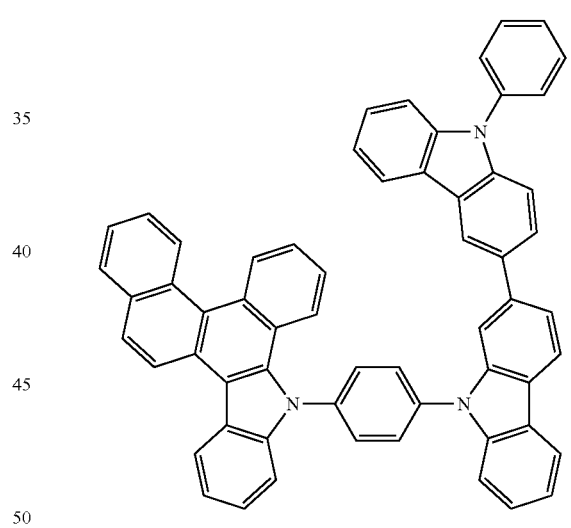
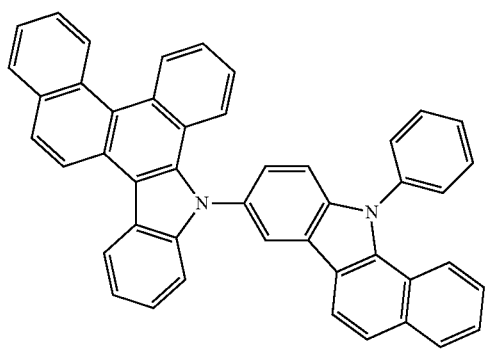
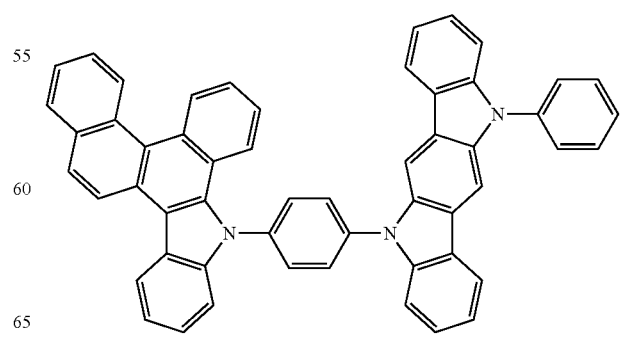

81
-continued
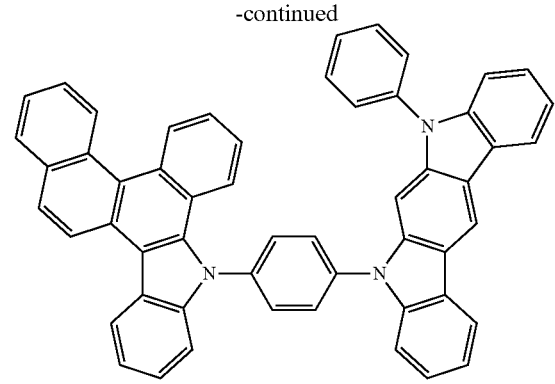
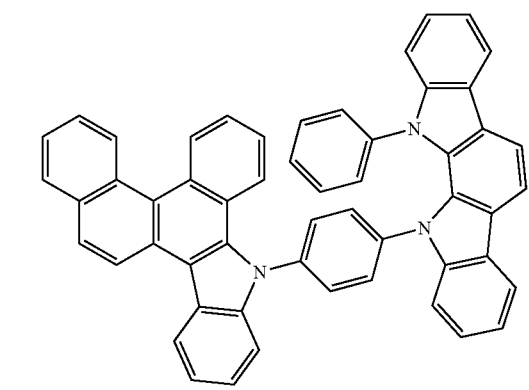
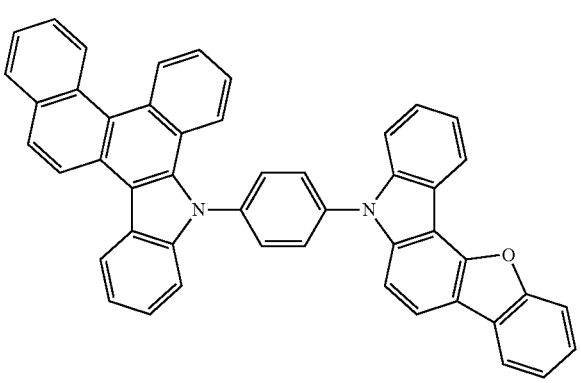
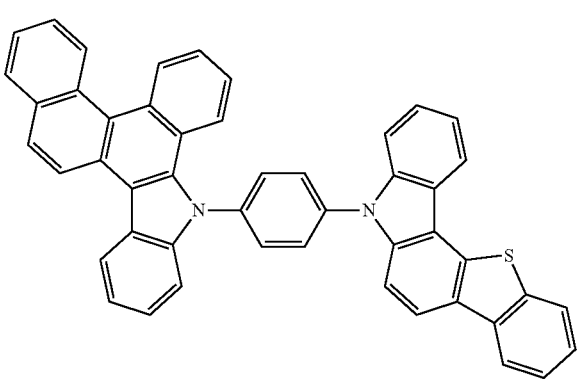
82
-continued
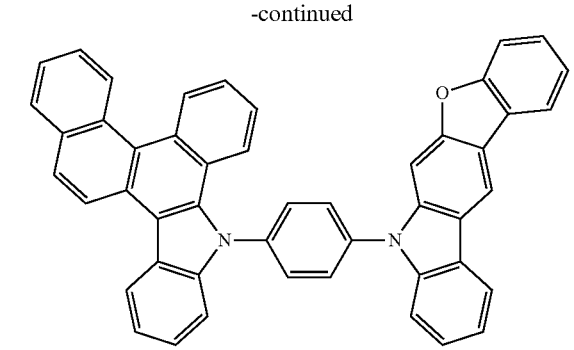
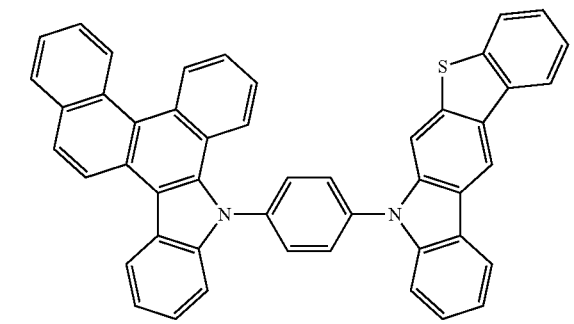
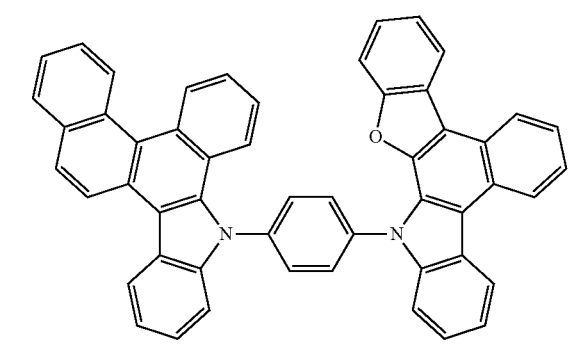
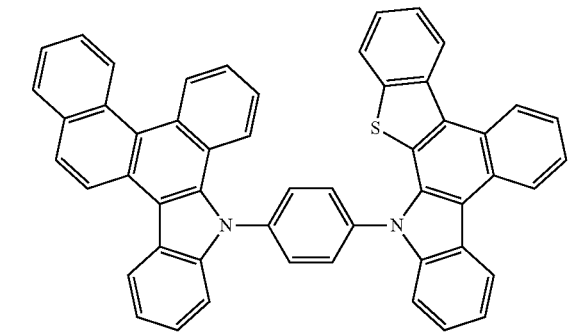
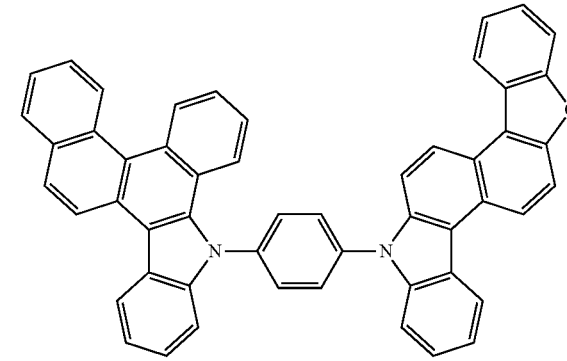

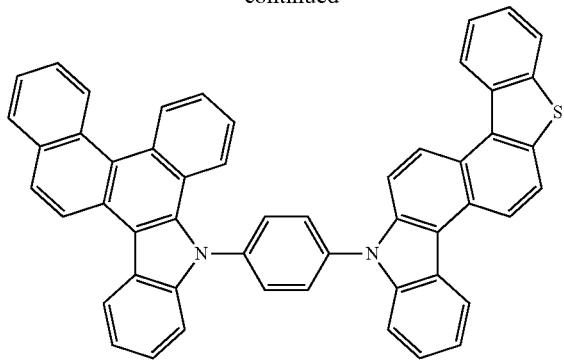

The compound in an aspect of the invention is useful as a material for organic EL devices and particularly useful as a material for forming a light emitting layer, a anode-side organic thin film layer (a hole transporting layer, a hole injecting layer, etc.), and a cathode-side organic thin film layer (an electron transporting layer, an electron injecting layer, etc.).

Material for Organic Electroluminescence Devices

The material for organic electroluminescence devices in an aspect of the invention comprises the nitrogen-containing heterocyclic derivative mentioned above. The content of the nitrogen-containing heterocyclic derivative in the material for organic electroluminescence devices is, but not particularly limited, 1% by mass or more, preferably 10% by mass or more, more preferably 50% by mass or more, still more preferably 80% by mass or more, and particularly preferably 90% by mass or more.

The material for organic EL devices of the invention is useful as a material for producing an organic EL device and may be used, for example, in a light emitting layer of a fluorescent emitting unit as a host material or a dopant material and in a light emitting layer of a phosphorescent emitting unit as a host material. In addition, in either a fluorescent emitting unit or a phosphorescent emitting unit, the material for organic EL devices of the invention is also useful as a material for an anode-side organic thin film layer which is formed between an anode and a light emitting layer and a material for a cathode-side organic thin film layer which is formed between a cathode and a light emitting layer, i.e., also useful as a material for a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein at least one layer is a light emitting layer.

Organic EL Device

The organic EL device in an aspect of the invention will be described below.

The organic EL device comprises an organic thin film layer between a cathode and an anode. The organic thin film layer comprises a light emitting layer and at least one layer of the organic thin film layer comprises the compound in an aspect of the invention.

Examples of the organic thin film layer comprising the compound in an aspect of the invention include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The compound in an aspect of the invention may be used in any of the above layers and preferably used in a light emitting layer of a fluorescent emitting unit as a host material or a dopant material or in a light emitting layer of a phosphorescent emitting unit as a host material. In addition, the compound in an aspect of the invention may be used in the anode-side organic thin film layer of an emission unit, such as a hole transporting layer and a hole injecting layer, or in the cathode-side organic thin film layer of an emission unit, such as an electron transporting layer and an electron injecting layer.

The organic EL device in an aspect of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the degree of charge recombination in the light emitting layer, thereby improving the lifetime.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device in an aspect of the invention is shown in the FIGURE wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer containing a phosphorescent host material and a phosphorescent dopant material (phosphorescent material). A hole injecting/transporting layer (an anode-side organic thin film layer) 6 may be disposed between the light emitting layer 5 and the anode 3, and an electron injecting/transporting layer (a cathode-side thin film layer) 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The organic EL device in an aspect of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds $\Omega/\square$ or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, such as an iridium complex, an osmium complex and a platinum complex, particularly an ortho-metallated complex comprising a metal selected from iridium, osmium and platinum being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.

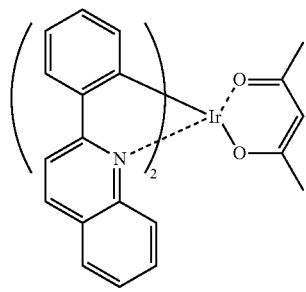

PQIr

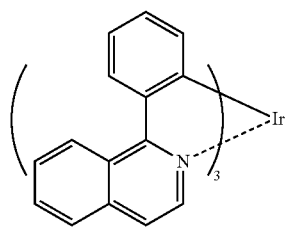

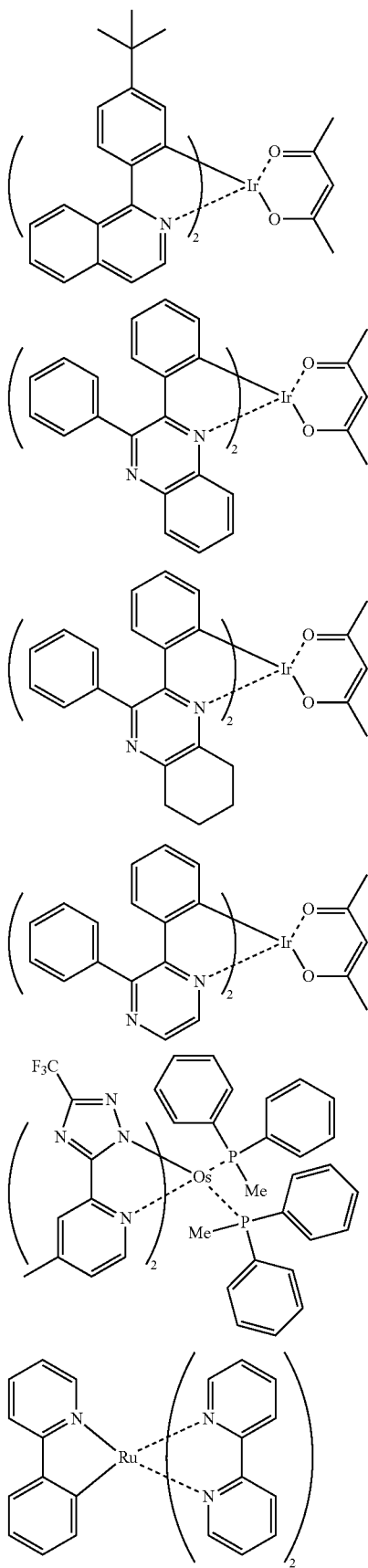

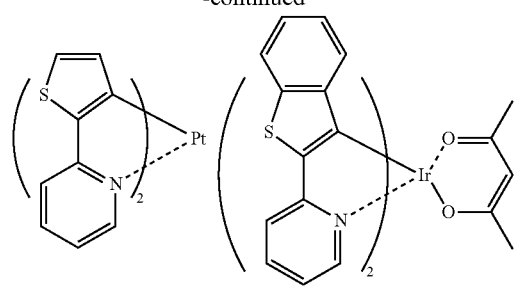
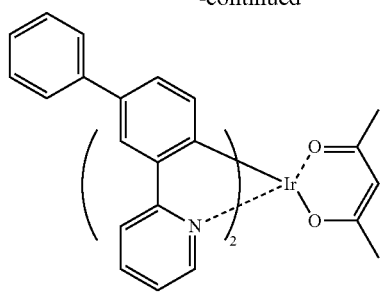
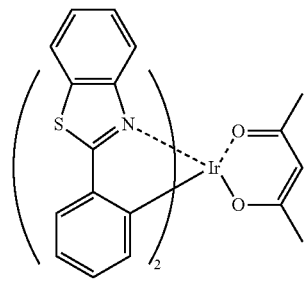
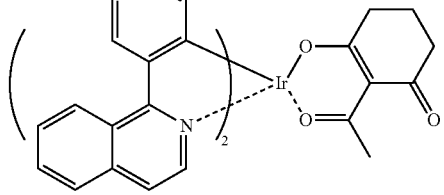
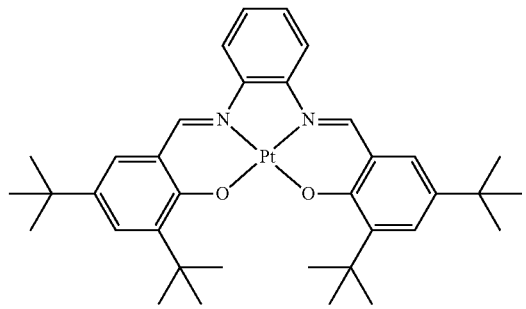
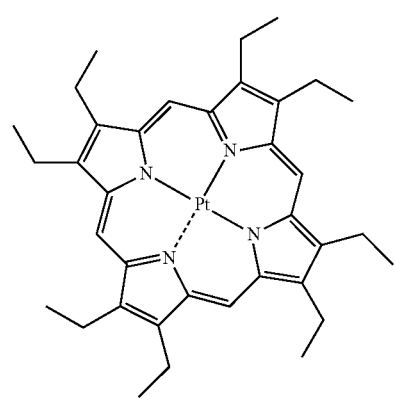
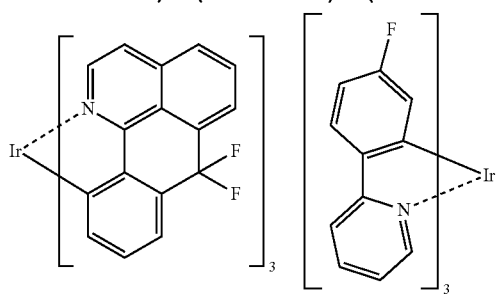
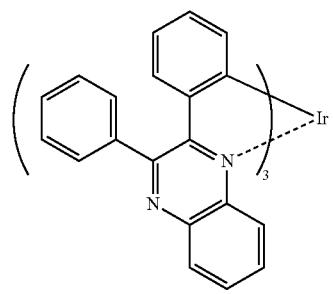
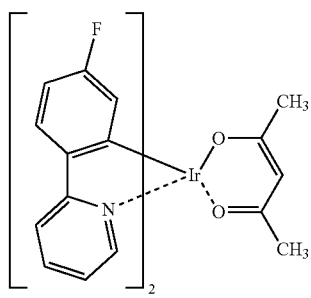
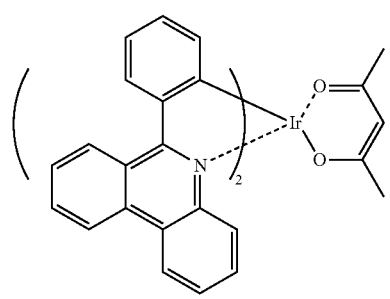
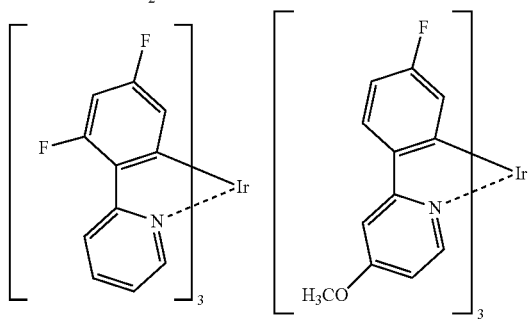

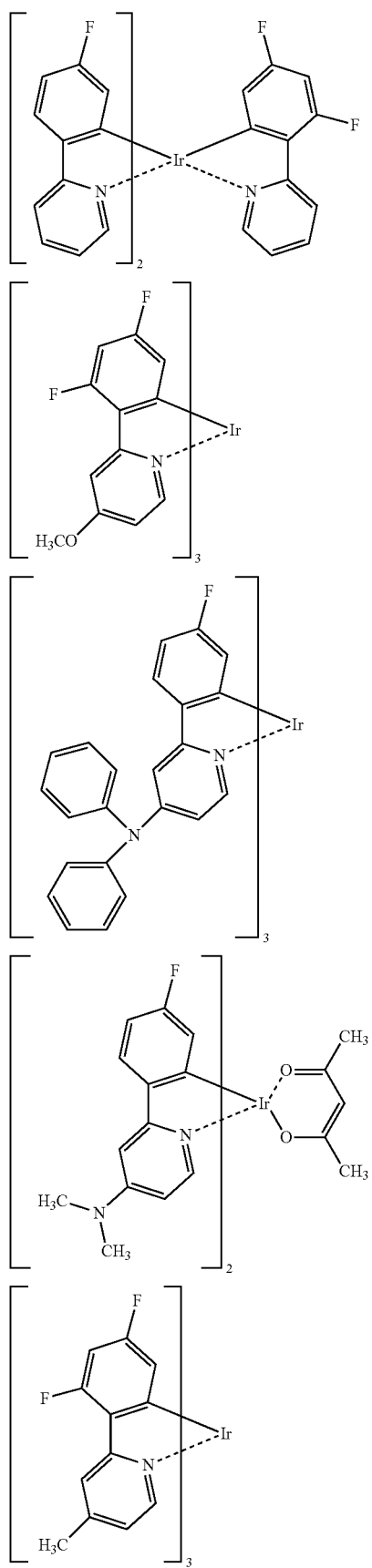
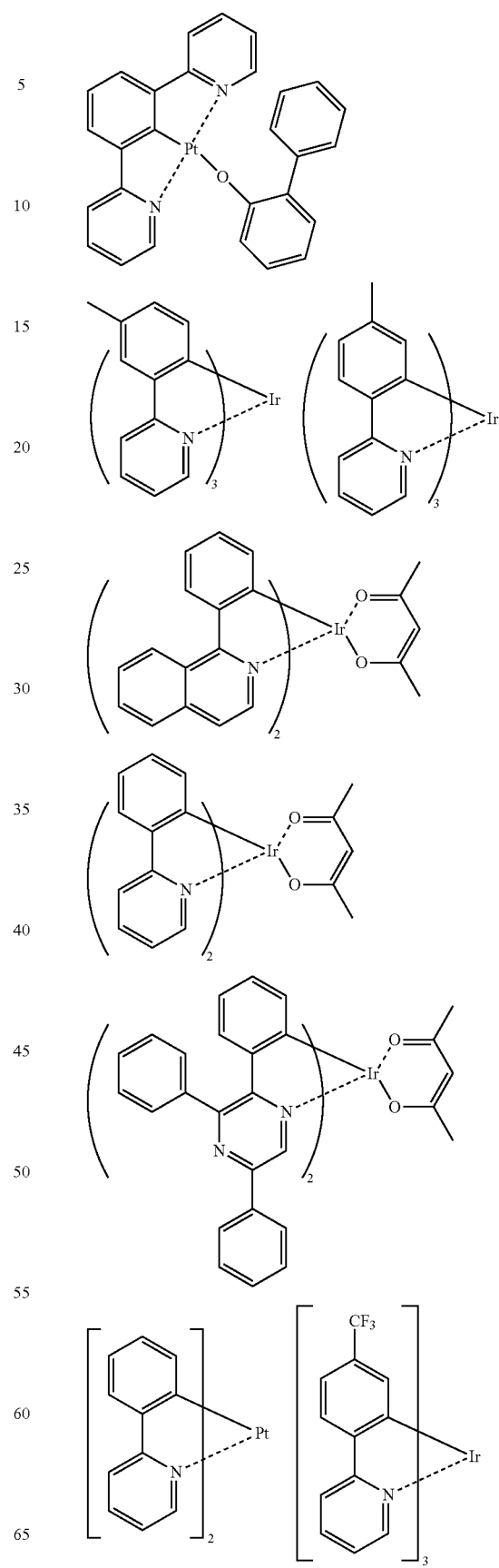

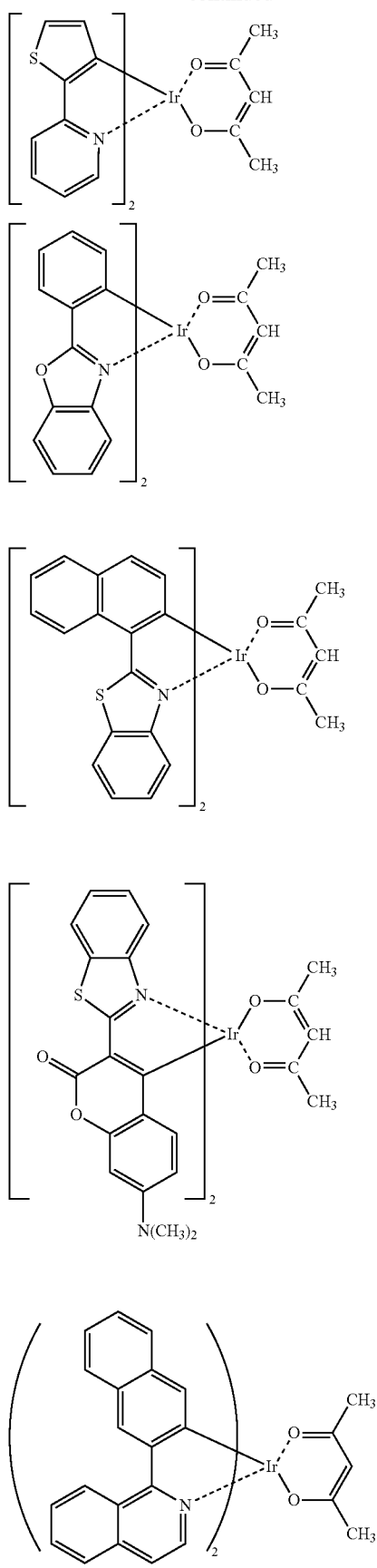
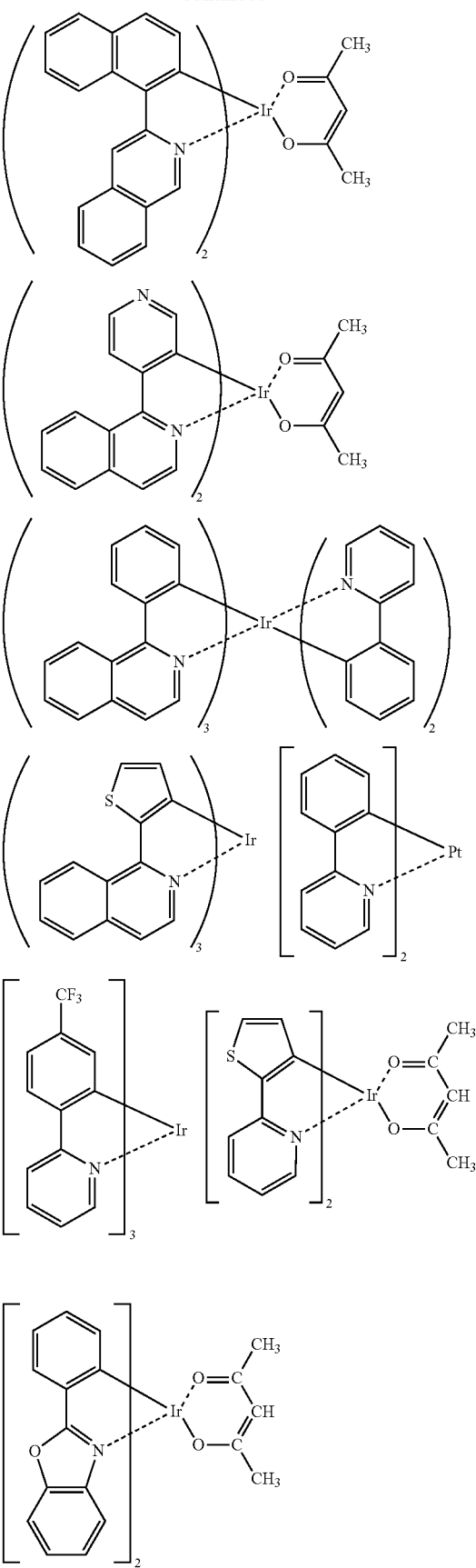

-continued

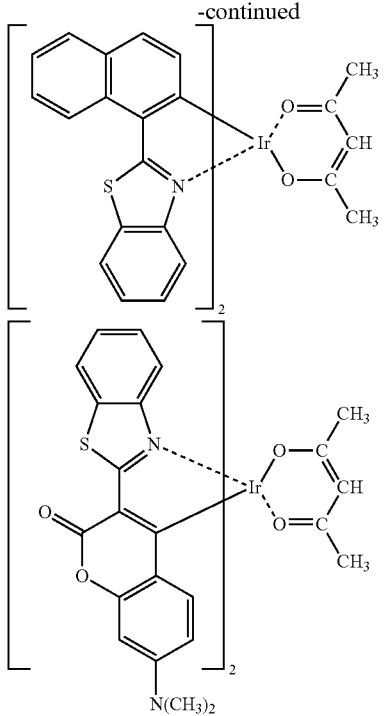

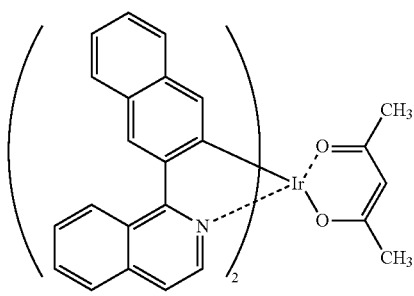

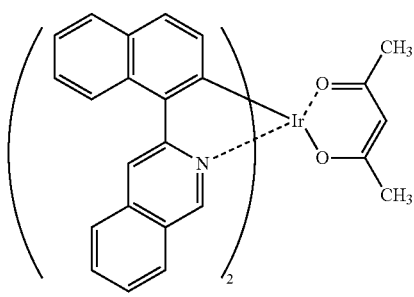

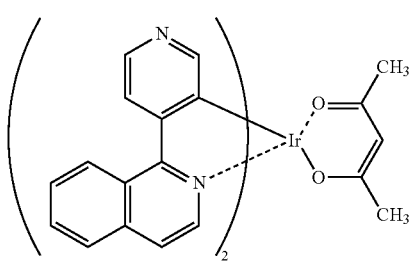

-continued

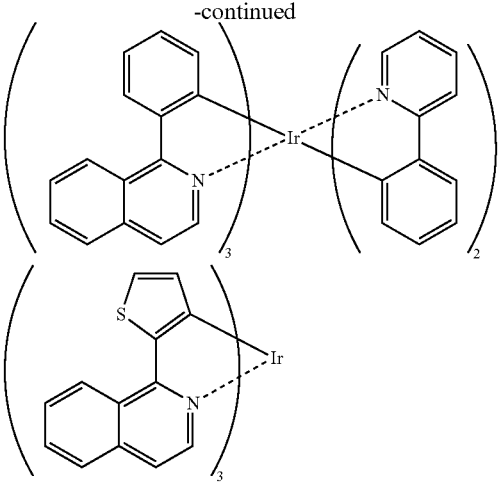

In addition, the complex represented by formula (X) or (Y) is also preferred as the phosphorescent dopant.

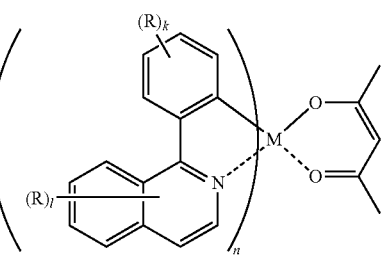

(X)

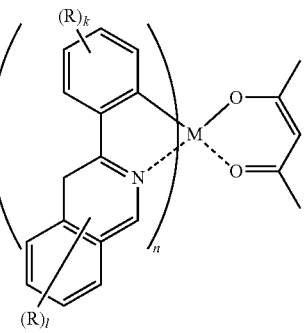

(Y)

wherein each R independently represents a hydrogen atom or a substituent group; k represents an integer of 1 to 4; l represents an integer of 1 to 6; n represents an integer of 2 to 4; and M represents Ir, Os, or Pt.

The substituent group represented by R is as defined above with respect to the substituent group of formula (1).

The phosphorescent host is a compound which confines the triplet energy of the phosphorescent dopant efficiently in the light emitting layer to cause the phosphorescent dopant to emit light efficiently. Although the material for organic EL device in an aspect of the invention is useful as a phosphorescent host, a compound other than the material for organic EL device may be used as the phosphorescent host according to the use of the device.

The material for organic EL device in an aspect of the invention and the compound other than it may be combinedly used in the same light emitting layer as the phosphorescent host material. If two or more light emitting layers are formed, the material for organic EL device can be used in one of the light emitting layers as the phosphorescent host material and a compound other than the material for organic EL device can be used in another light emitting layer as the phosphorescent host material. The material for organic EL device may be used in an organic layer other than the light emitting layer. In this case, a compound other than the material for organic EL device may be used as a phosphorescent host of the light emitting layer.

Examples of the preferred phosphorescent host other than the material for organic EL device in an aspect of the invention include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

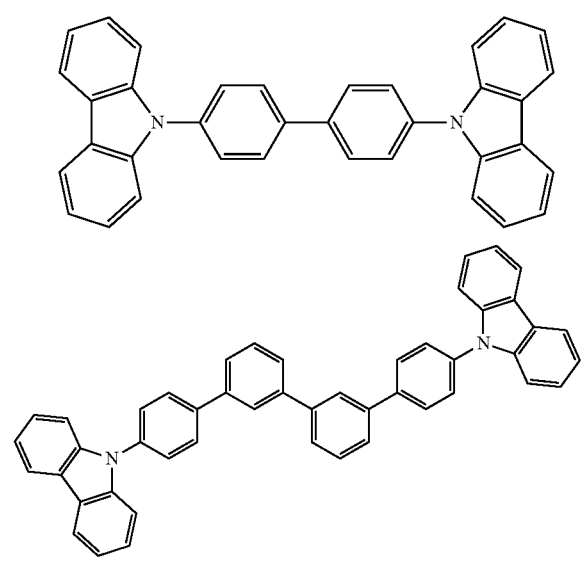

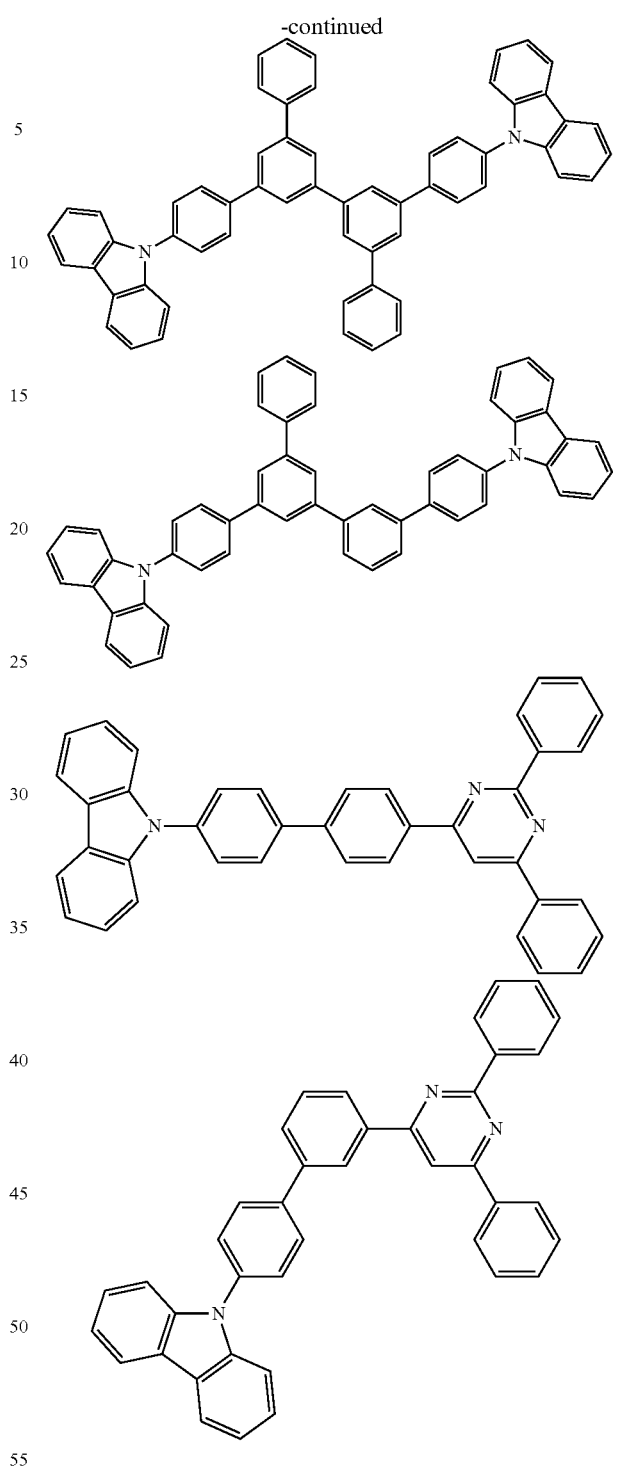

The organic EL device in an aspect of the invention may comprise a light emitting layer comprising a fluorescent material, i.e., a fluorescent emitting layer. The fluorescent emitting layer may be formed from a known fluorescent material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as the host material and the arylamine derivative is preferably used as the dopant. The materials described in WO 2010/134350 and WO 2010/134352 are preferably used. The material for organic EL device may be used in a fluorescent emitting layer as a fluorescent emitting material or a host material.

The anthracene derivative for use as a fluorescent material has preferably 26 to 100, more preferably 26 to 80, and still more preferably 26 to 60 ring carbon atoms. The anthracene derivative is preferably represented by formula (10):

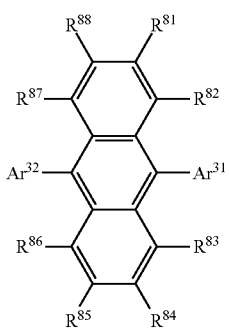

(10)

wherein:

each of $Ar^{31}$ and $Ar^{32}$ independently represents a substituted or unsubstituted aryl group having 6 to 50 ring carbon atoms or a substituted or unsubstituted heteroaryl group having 5 to 50 ring atoms; and each of $R^{81}$ to $R^{88}$ independently represents a hydrogen atom, a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group, or a hydroxyl group.

The aryl group having 6 to 50 ring carbon atoms is preferably an aryl group having 6 to 40 ring carbon atoms and more preferably an aryl group having 6 to 30 ring carbon atoms.

The heteroaryl group having 5 to 50 ring atoms is preferably a heteroaryl group having 5 to 40 ring atoms and more preferably a heteroaryl group having 5 to 30 ring atoms.

The alkyl group having 1 to 50 carbon atoms is preferably an alkyl group having 1 to 30 carbon atoms, more preferably an alkyl group having 1 to 10 carbon atoms, and still more preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, and still more preferably an alkoxy group having 1 to 5 carbon atoms.

The aralkyl group having 7 to 50 carbon atoms is preferably an aralkyl group having 7 to 30 carbon atoms and more preferably an aralkyl group having 7 to 20 carbon atoms.

The aryloxy group having 6 to 50 ring carbon atoms is preferably an aryloxy group having 6 to 40 ring carbon atoms and more preferably an aryloxy group having 6 to 30 ring carbon atoms.

The arylthio group having 6 to 50 ring carbon atoms is preferably an arylthio group having 6 to 40 ring carbon atoms and more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, and still more preferably an alkoxycarbonyl group having 2 to 5 carbon atoms.

Examples of the halogen atom include a fluorine atom, a chlorine atom, and a bromine atom.

Each of $Ar^{31}$ and $Ar^{32}$ particularly preferably represents a substituted or unsubstituted aryl group having 6 to 50 ring carbon atoms.

The anthracene derivative represented by formula (10) is preferably represented by formula (10-1);

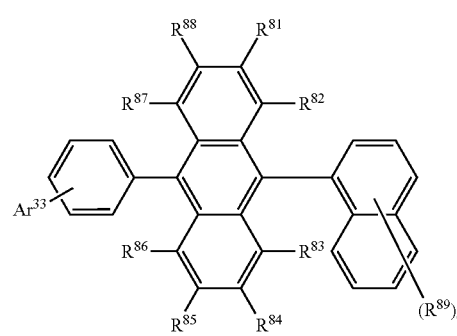

(10-1)

wherein:

$Ar^{33}$ represents a substituted or unsubstituted aryl group having 6 to 50 ring carbon atoms or a substituted or unsubstituted heteroaryl group having 5 to 50 ring atoms;

each of $R^{81}$ to $R^{88}$ is as defined above;

$R^{89}$ is defined in the same manner as in $R^{81}$ to $R^{88}$; and a is an integer of 1 to 7.

Preferred examples of $R^{81}$ to $R^{88}$ are as described above. Preferred examples of $R^{89}$ are the same as those of $R^{81}$ to $R^{88}$. The subscript a is preferably an integer of 1 to 3 and more preferably 1 or 2.

The aryl group having 6 to 50 ring carbon atoms for $Ar^{33}$ is preferably an aryl group having 6 to 40 ring carbon atoms, more preferably an aryl group having 6 to 30 ring carbon atoms, still more preferably an aryl group having 6 to 20 ring carbon atoms, and particularly preferably an aryl group having 6 to 12 ring carbon atoms.

The arylamine derivative for use as the fluorescent material is preferably an aryldiamine derivative, more preferably an aryldiamine derivative comprising a pyrene skeleton, and still more preferably an aryldiamine derivative having a pyrene skeleton and a dibenzofuran skeleton.

The aryldiamine derivative is preferably an aryldiamine derivative represented by formula (11):

(11)

wherein:

each of $Ar^{34}$ to $Ar^{37}$ independently represents a substituted or unsubstituted aryl group having 6 to 50 ring carbon atoms or a substituted or unsubstituted heteroaryl group having 5 to 50 ring atoms; and $L^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, still more preferably an aryl group having 6 to 12 ring carbon atoms, with a phenyl group and a naphthyl group being particularly preferred.

The heteroaryl group having 5 to 50 ring atoms is preferably a heteroaryl group having 5 to 40 ring atoms, more preferably a heteroaryl group having 5 to 30 ring atoms, and still more preferably a heteroaryl group having 5 to 20 ring atoms, for example, a carbazolyl group, a dibenzofuranyl group and dibenzothiophenyl group, with a dibenzofuranyl group being preferred. Preferred examples of the substituent for the heteroaryl group include an aryl group having 6 to 30, preferably 6 to 20, and more preferably 6 to 12 ring carbon atoms, with a phenyl group and a naphthyl group being more preferred.

The arylene group having 6 to 50 ring carbon atoms is preferably an arylene group having 6 to 40 ring carbon atoms, more preferably an arylene group having 6 to 30 ring carbon atoms, and still more preferably an arylene group having 6 to 20 ring carbon atoms, with a pyrenyl group being particularly preferred.

A double host (host/co-host) system may be used for the light emitting layer. For example, to control the carrier balance in the light emitting layer, an electron transporting host and a hole transporting host may be combinedly used.

The light emitting layer may be also made into a double dopant layer. When two or more kinds of dopant materials having high quantum yield are used in the light emitting layer, each dopant emits light with its own color. For example, a yellow light emitting layer can be obtained by co-depositing a host, a red-emitting dopant and a green-emitting dopant.

The light emitting layer may further comprise a hole transporting material, an electron transporting material, and a polymer binder, if necessary.

The thickness of the light emitting layer is preferably 5 to 50 nm, more preferably 7 to 50 nm and most preferably 10 to 50 nm. If less than 5 nm, the light emitting layer may be difficult to form and the color may be difficult to control. If exceeding 50 nm, the driving voltage is likely to increase.

Electron-Donating Dopant

The organic EL device in an aspect of the invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device in an aspect of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently. The material for organic EL device in an aspect of the invention may be used in the electron transporting layer as the electron transporting material.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

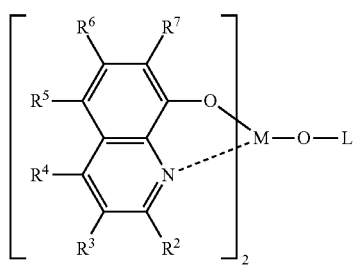
(A)

wherein each of $R^2$ to $R^7$ independently represents a hydrogen atom, a heavy hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heteroaryl group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom or a heavy hydrogen atom.

The arylamino group is represented by $-NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom or a heavy hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $-COOY'$, wherein $Y'$ is an alkyl group having 1 to 20 carbon atoms.

M is aluminum (Al), gallium (Ga), or indium (In), with In being preferred.

L is a group represented by formula (A') or (A''):

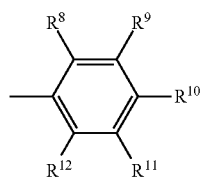
(A')

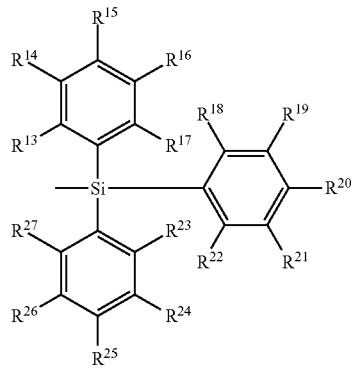
(A'')

wherein each $R^8$ to $R^{12}$ independently represents a hydrogen atom, a heavy hydrogen atom or a substituted or unsubstituted hydrocarbon group having 1 to 40 carbon atoms. Two neighboring groups may form a ring structure. Each of $R^{13}$ to $R^{27}$ independently represents a hydrogen atom, a heavy hydrogen atom or a substituted or unsubstituted hydrocarbon group having 1 to 40 carbon atoms. Two neighboring groups may form a ring structure.

Examples of the hydrocarbon group having 1 to 40 carbon atoms for $R^8$ to $R^{12}$ and $R^{13}$ to $R^{27}$ in formulae (A') and (A'') are the same as those described above with respect to $R^2$ to $R^7$ of formula (A). Examples of the divalent group formed by two neighboring groups of $R^8$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

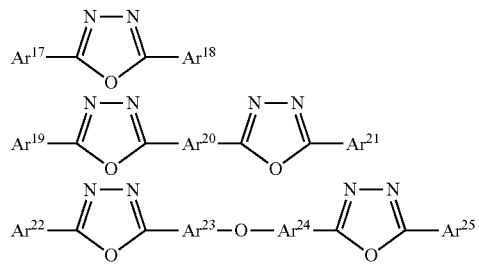

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

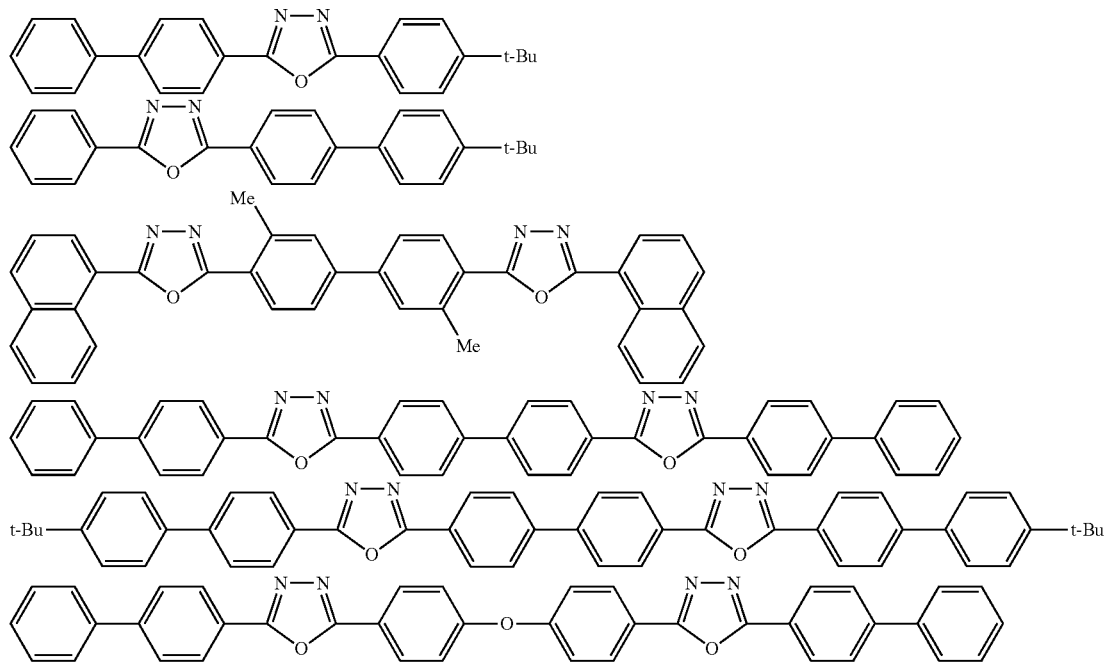

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

 (B)

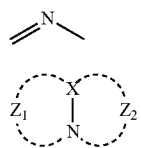 (C)

wherein X is a carbon atom or a nitrogen atom and each of $Z_1$ and $Z_2$ independently represents a group of atoms for completing the nitrogen-containing heterocyclic ring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

(D)

The nitrogen-containing group of the nitrogen-containing aromatic polycyclic compound is selected, for example, from the nitrogen-containing heterocyclic groups shown below:

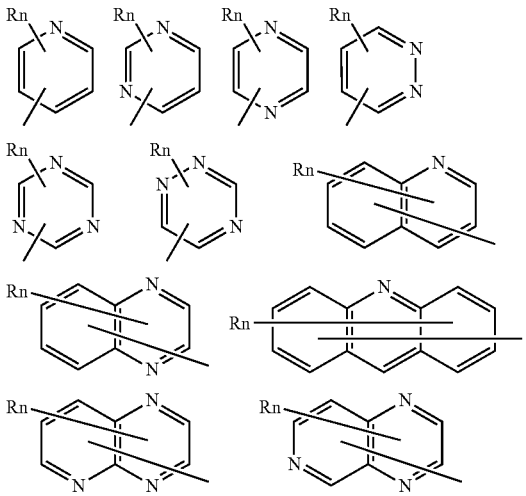

-continued

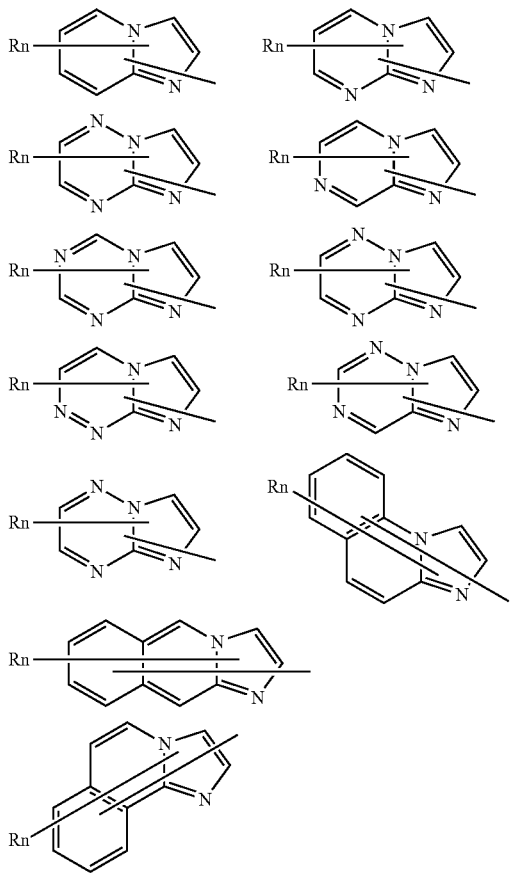

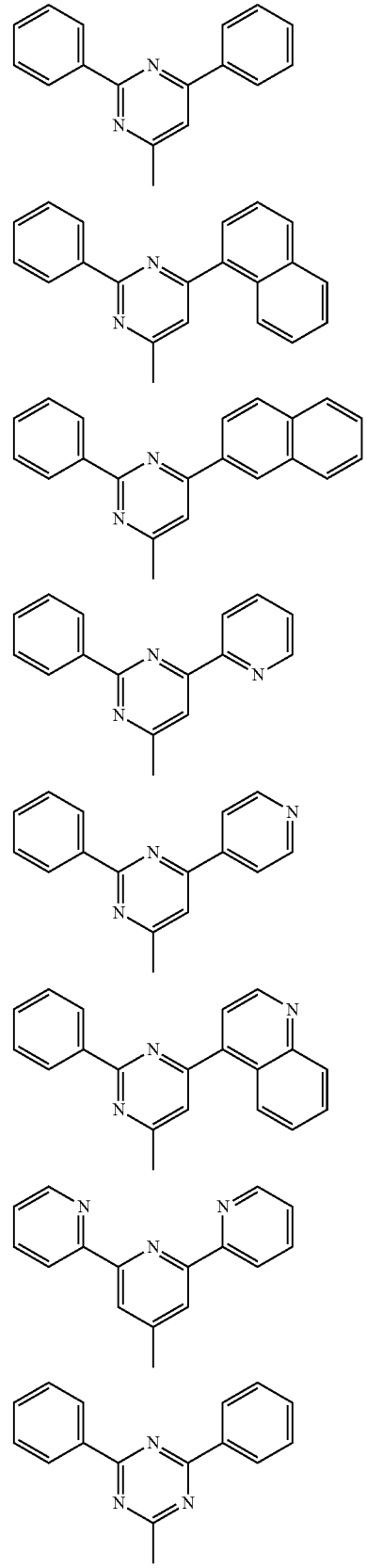

HAr is selected, for example, from the following groups:

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, groups R may be the same or different.

More preferred is a nitrogen-containing heterocyclic derivative represented by formula (D1):

wherein HAr is a substituted or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substituted or unsubstituted divalent aromatic hydrocarbon group having 6 to 40 carbon atoms; and $Ar^2$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

-continued

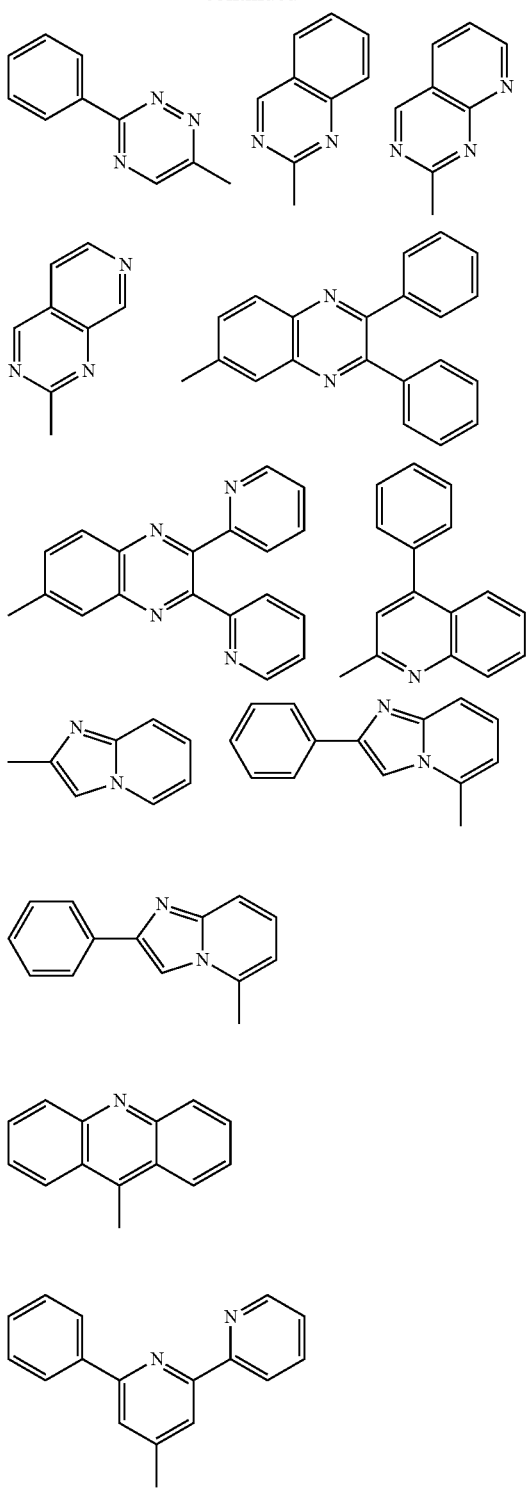

L¹ is selected, for example, from the following groups:

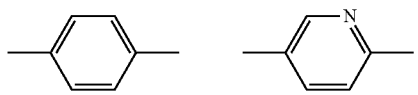

Ar¹ is selected, for example, from the group represented by formula (D2) or (D3):

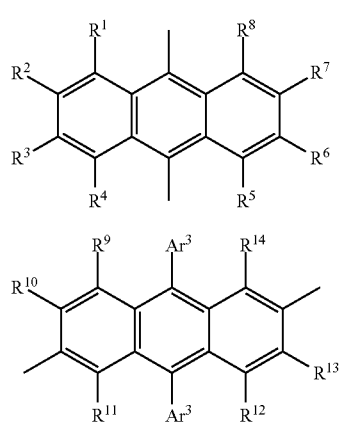

wherein $R^1$ to $R^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar_3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms. Each of $R^1$ to $R^8$ may be selected from a hydrogen atom and a heavy hydrogen atom.

$Ar^2$ is selected, for example, from the following groups:

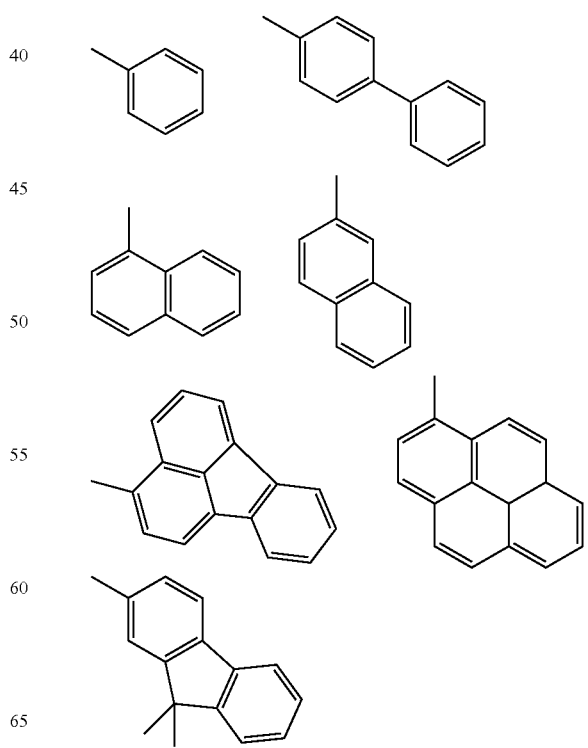

In addition, the following compound is preferably used as the nitrogen-containing aromatic polycyclic compound for use as the electron transporting compound:

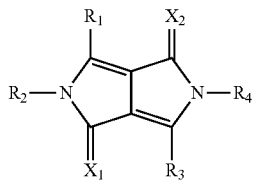

(D4)

wherein $R_1$ to $R_4$ each independently represent a hydrogen atom, a heavy hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound:

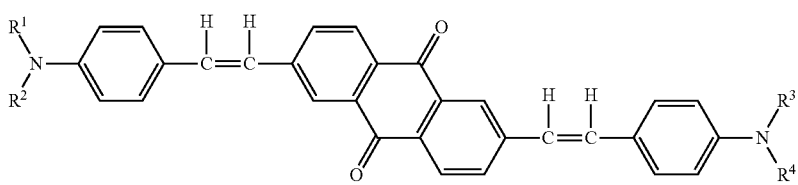

(D5)

wherein $R^1$, $R^2$, $R^3$, and $R^4$ may be the same or different and each represents an aromatic hydrocarbon group or a fused aromatic hydrocarbon group each represented by formula (D6):

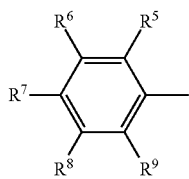

(D6)

wherein $R^5$, $R^6$, $R^7$, $R^8$, and $R^9$ may be the same or different and each represents a hydrogen atom, a heavy hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom and a heavy hydrogen atom.

Further, a polymer including the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (E) to (G):

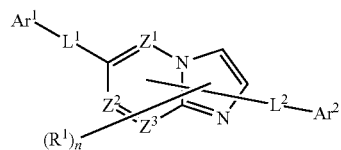

(E)

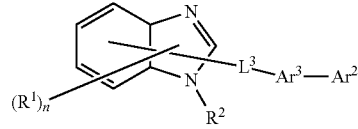

(F)

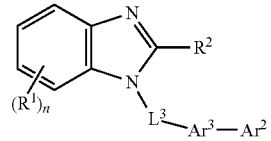

(G)

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, groups $R^1$ may be the same or different, and neighboring two groups $R^1$ may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon ring group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, and an imidazo[1,2-a]pyrimidinyl.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably, but not particularly limited to, 1 to 100 nm.

Preferred examples of the material for an electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed.

Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in an aspect of the invention may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit. The material for organic EL device in an aspect of the invention may be used in the hole transporting layer as a hole transporting material.

Another preferred material for the hole transporting layer may include an aromatic amine compound, for example, an aromatic amine derivative represented by formula (H):

wherein:

each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group; and L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (H) are shown below.

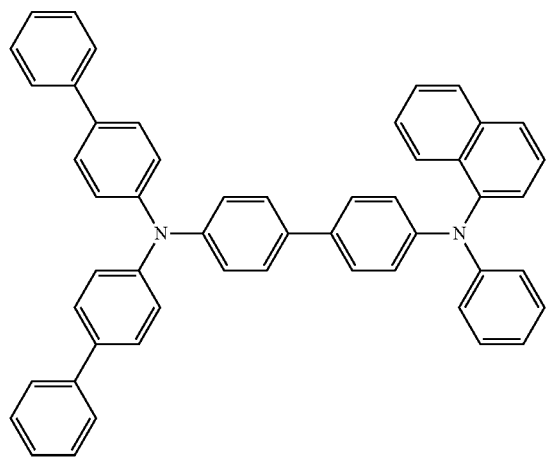

115
-continued
116
-continued
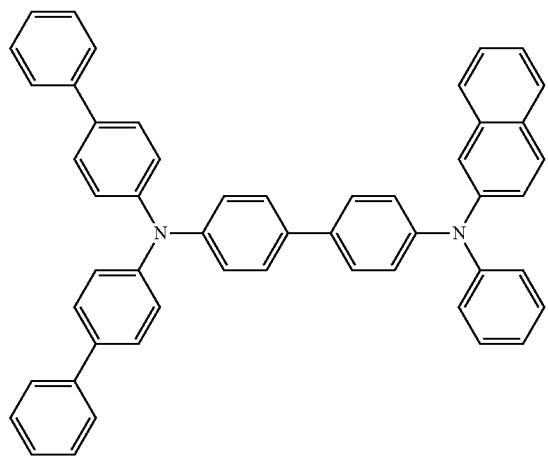
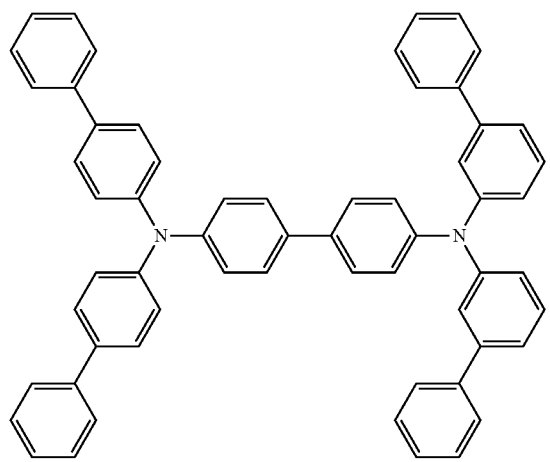
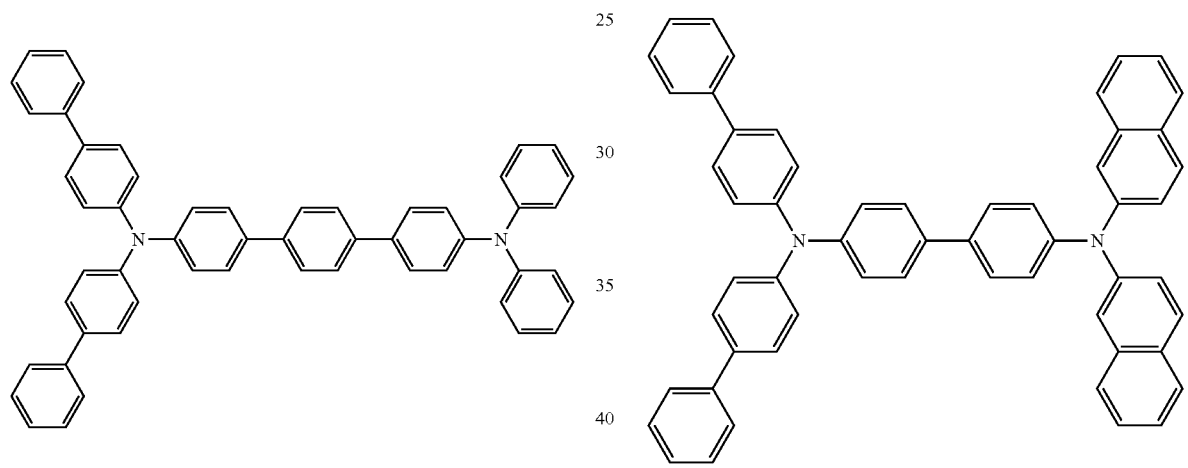
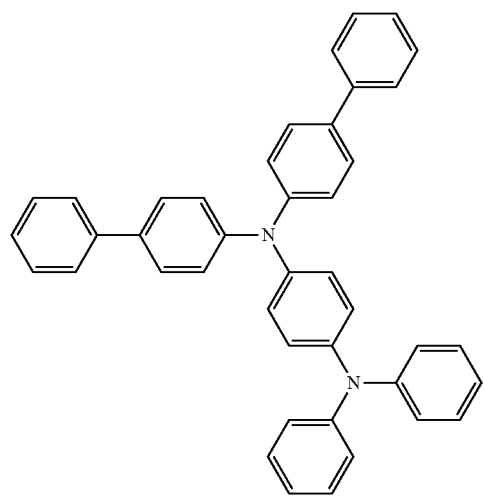
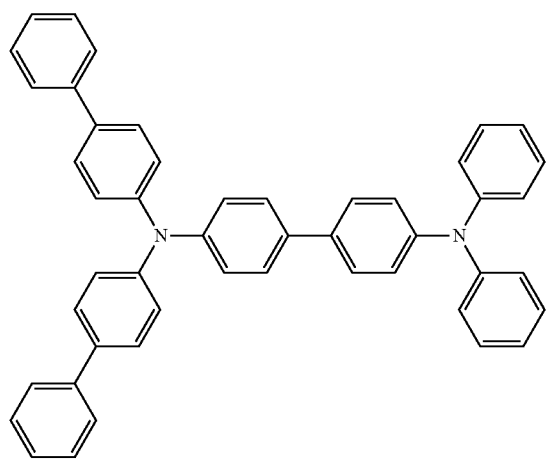

117
-continued
118
-continued
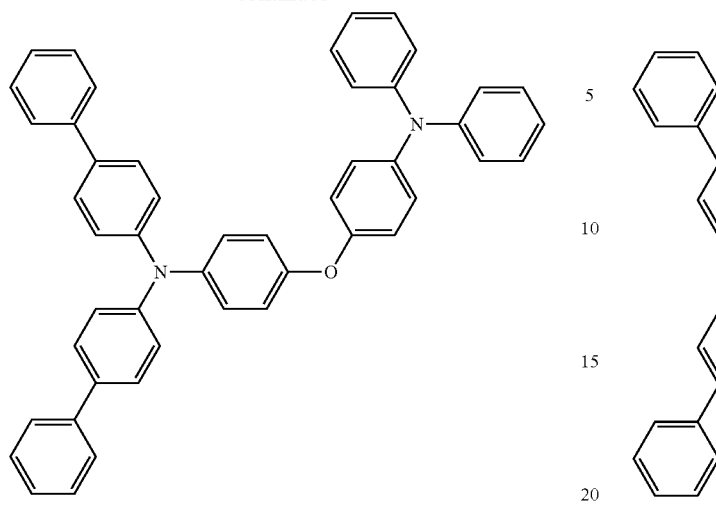
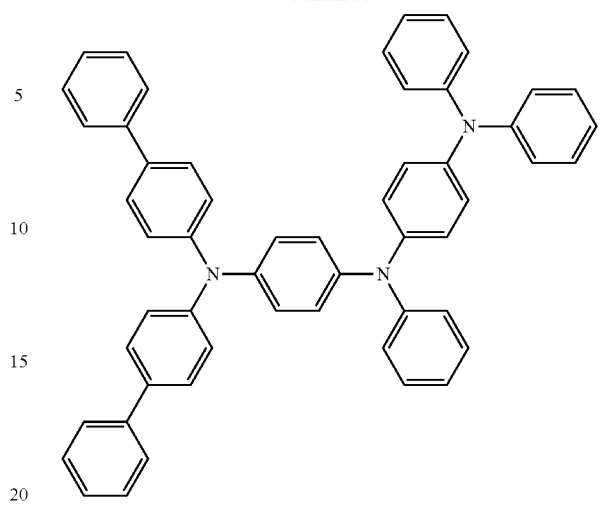
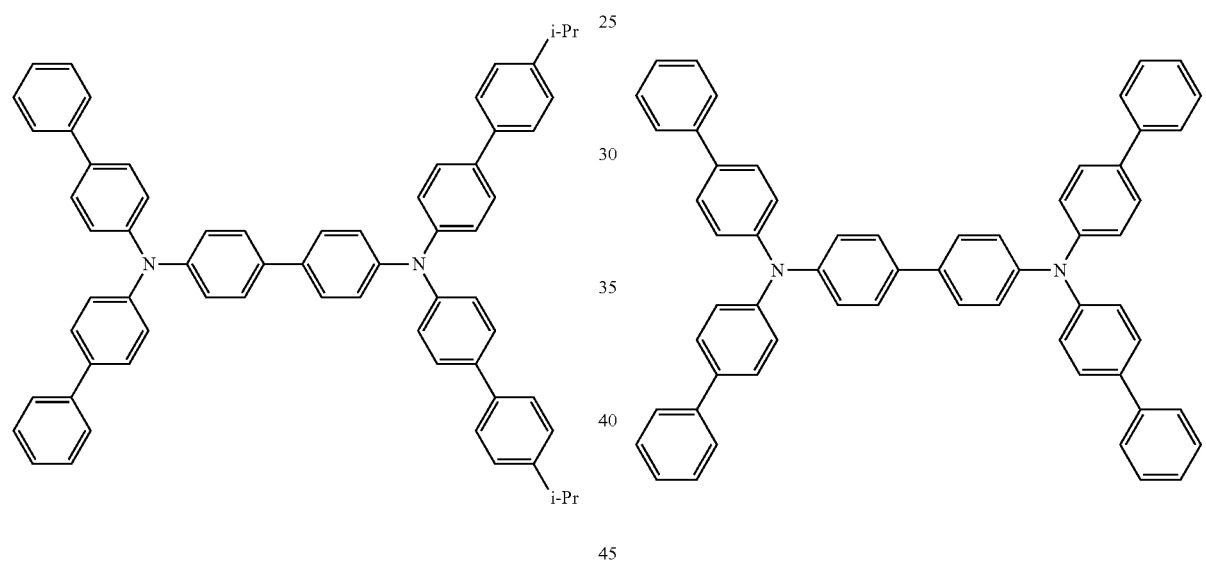
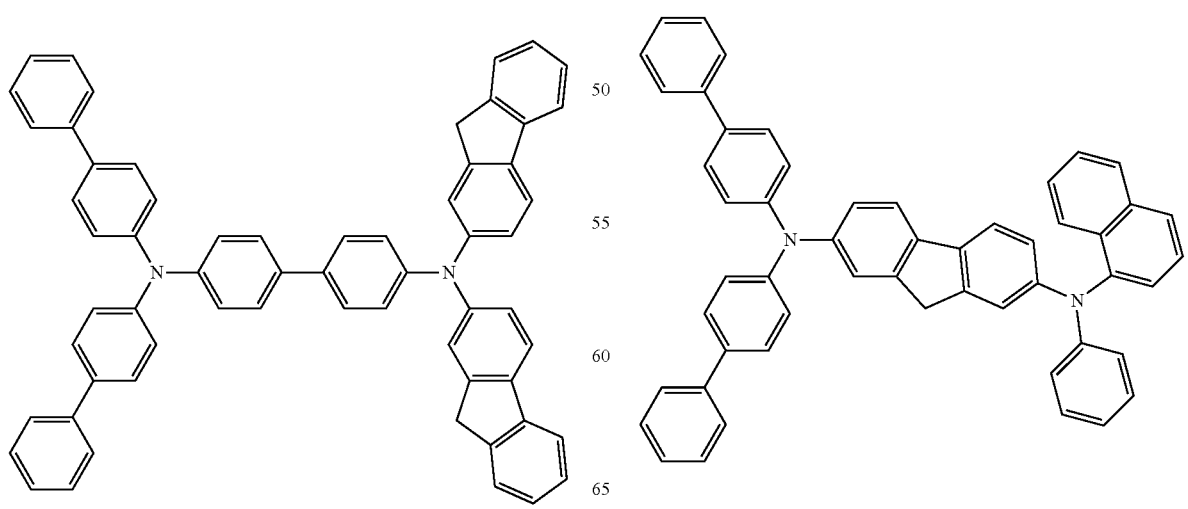

119
-continued
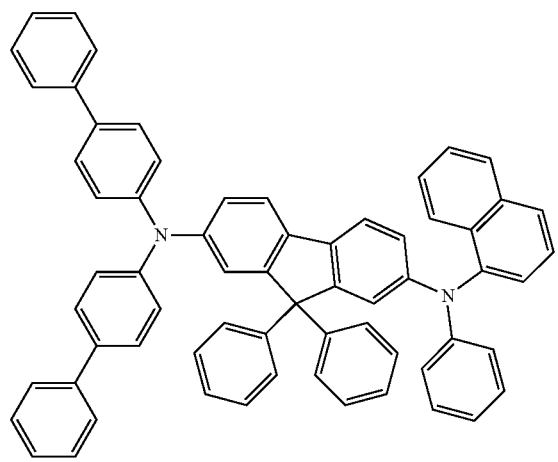
120
-continued
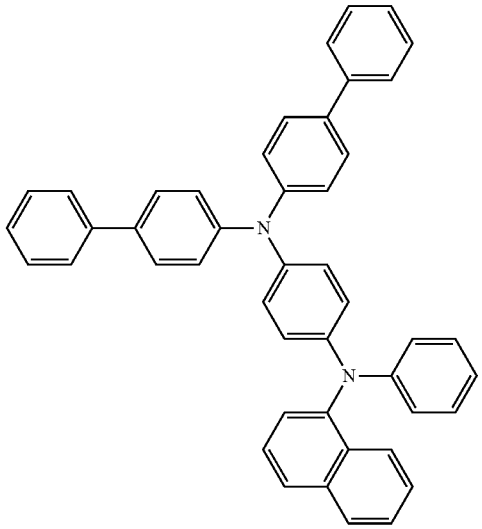
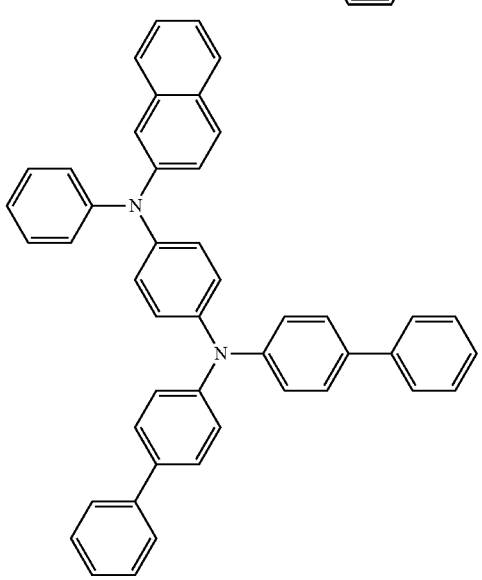
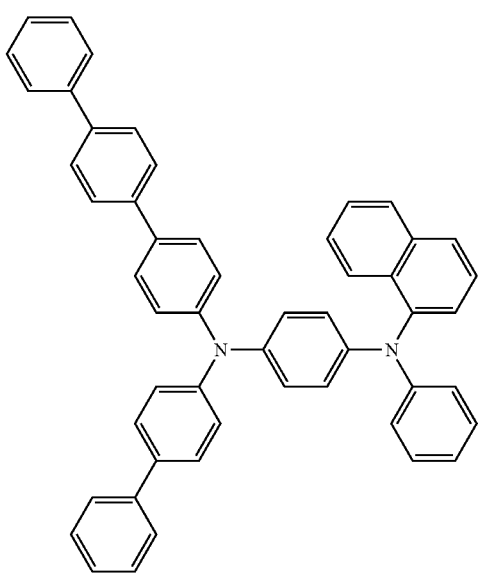

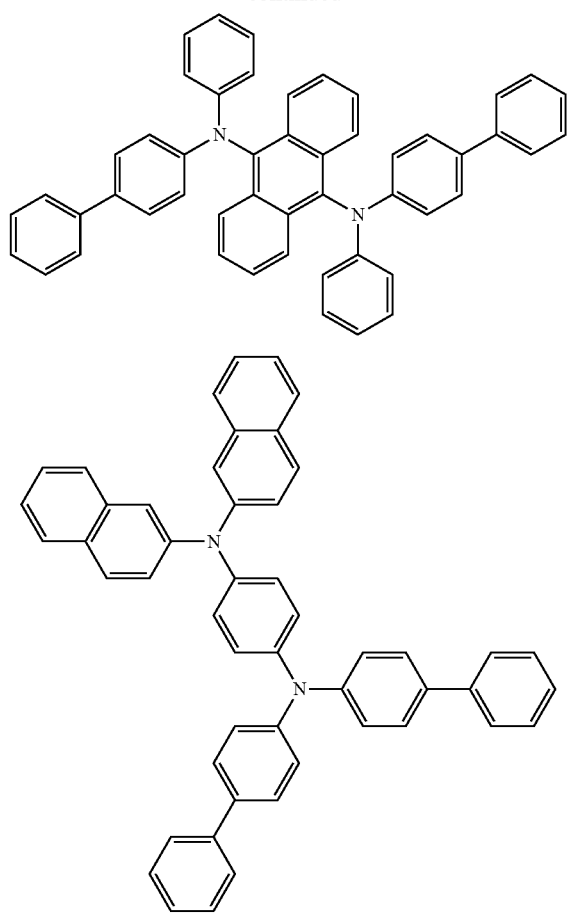
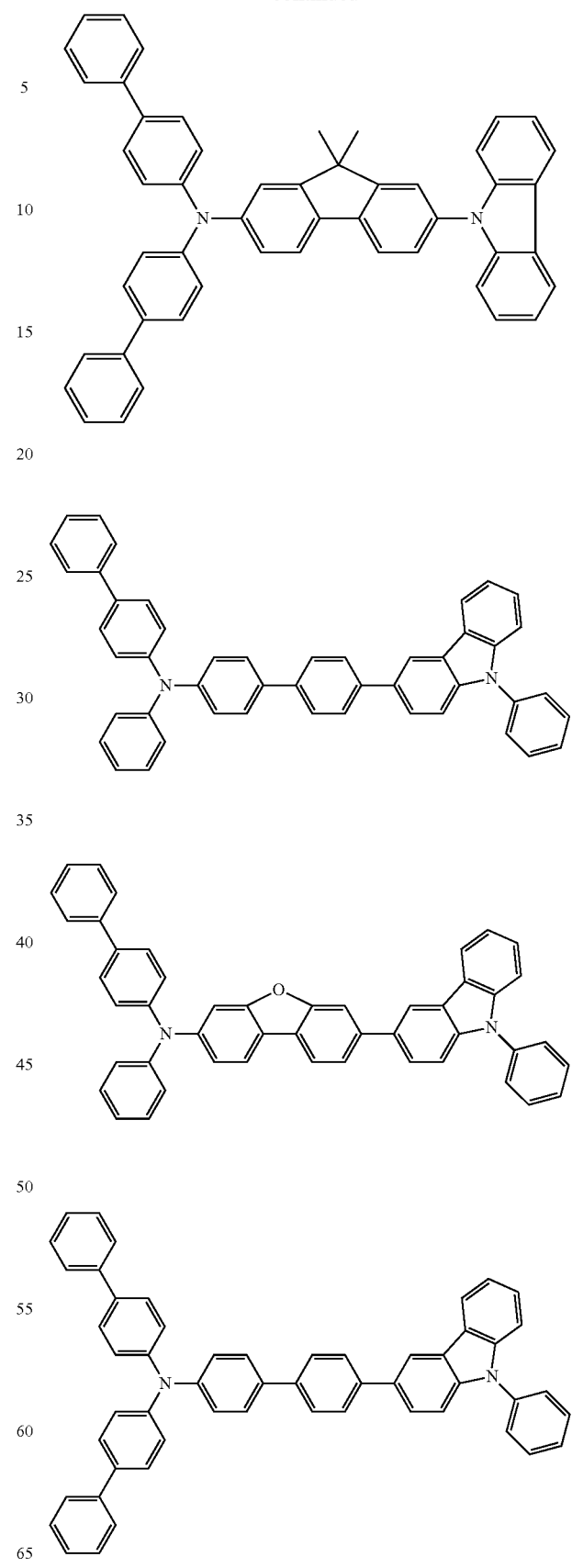

-continued
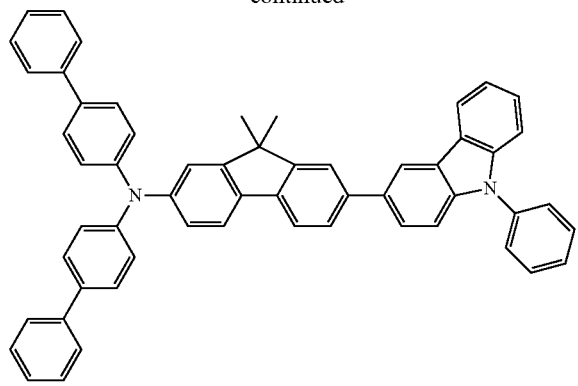
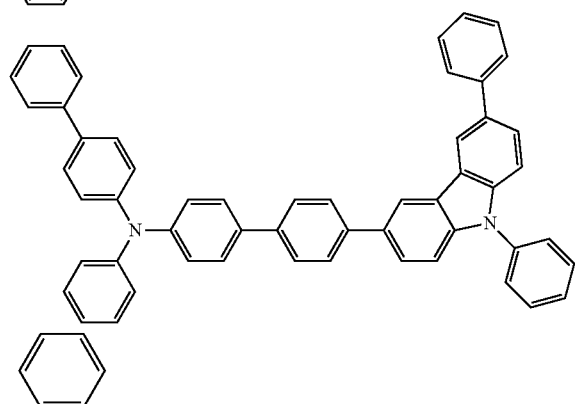
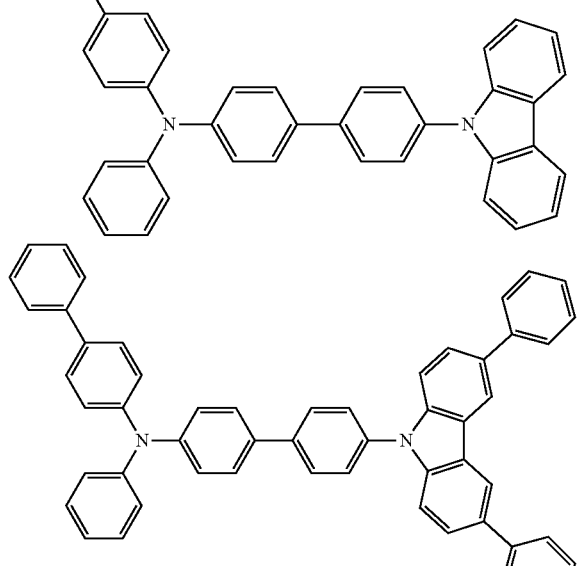
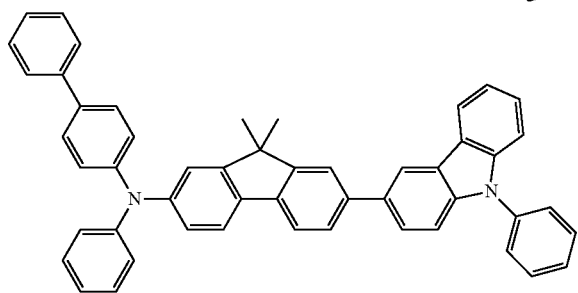
An aromatic amine represented by formula (J) is also preferably used to form the hole transporting layer:
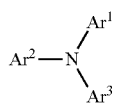
wherein $Ar^1$ to $Ar^3$ are the same as defined with respect to $Ar^1$ to $Ar^4$ of formula (H). Examples of the compound represented by formula (J) are shown below, although not limited thereto.
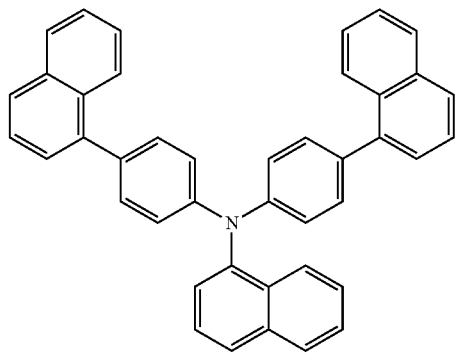
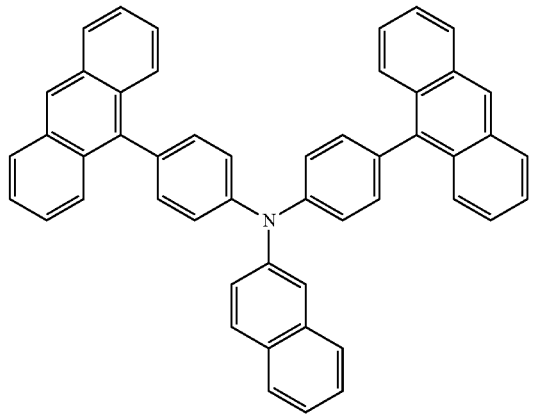
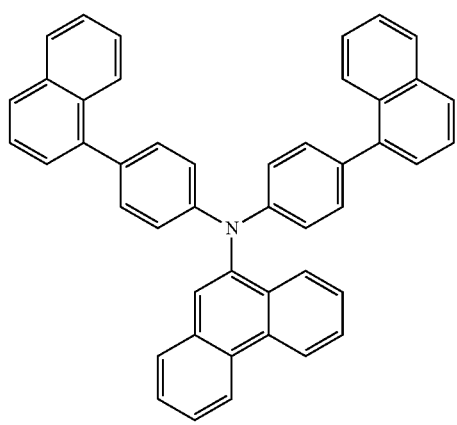

125
-continued
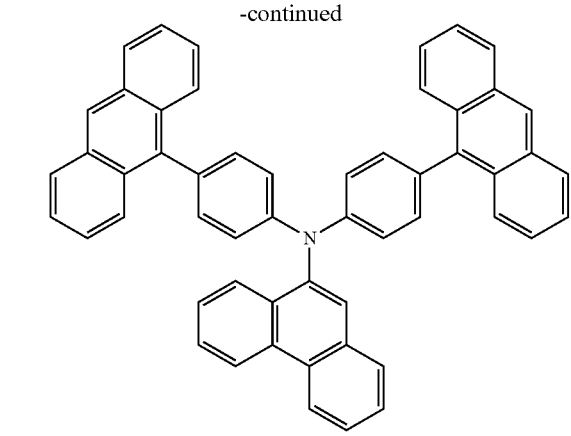
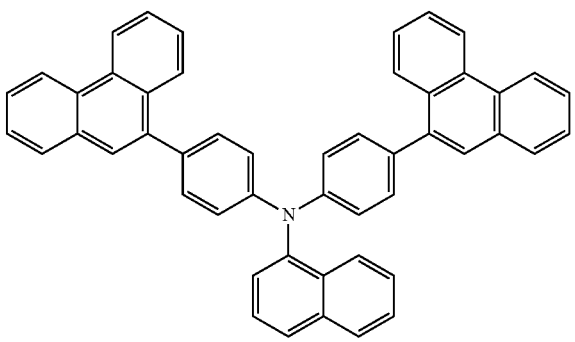
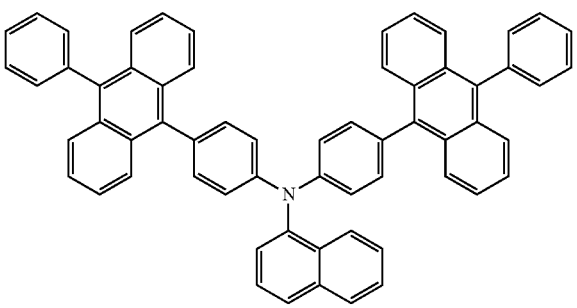
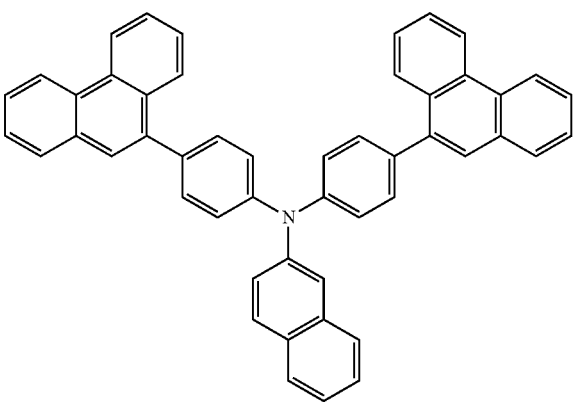
126
-continued
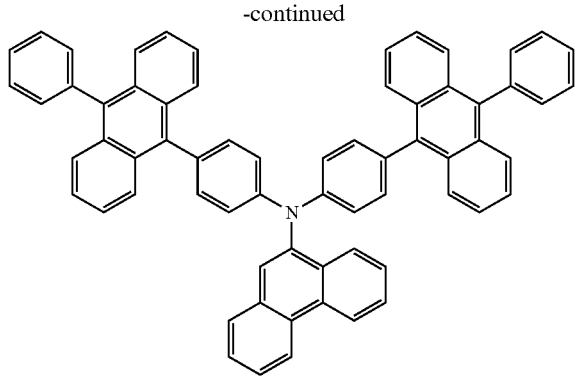
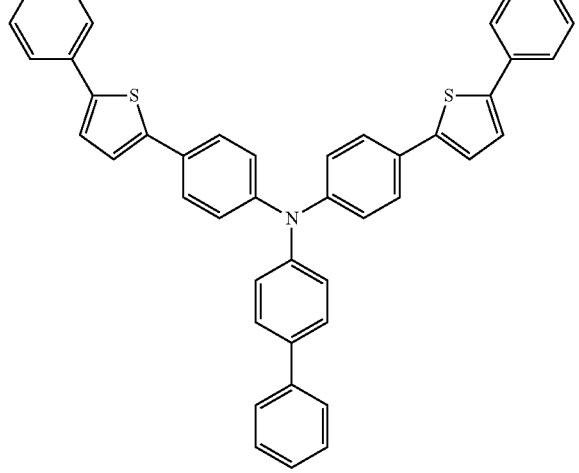

127
-continued

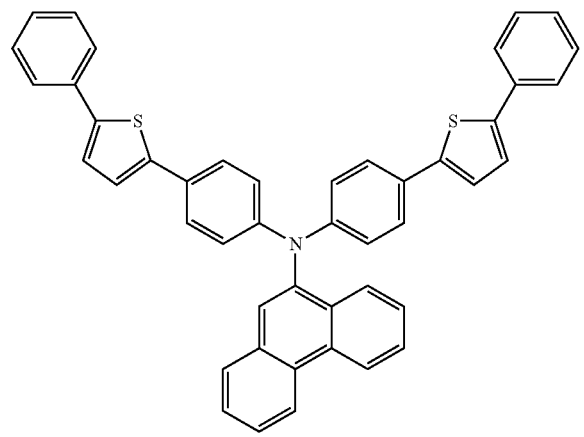

128
-continued

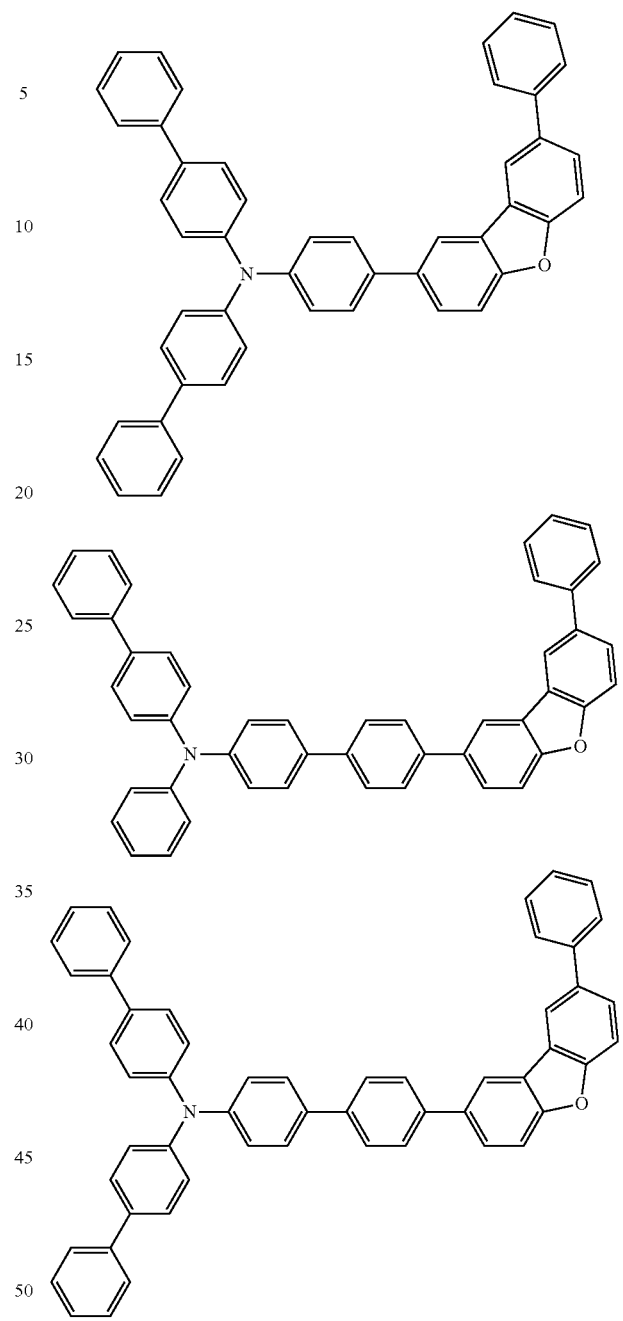

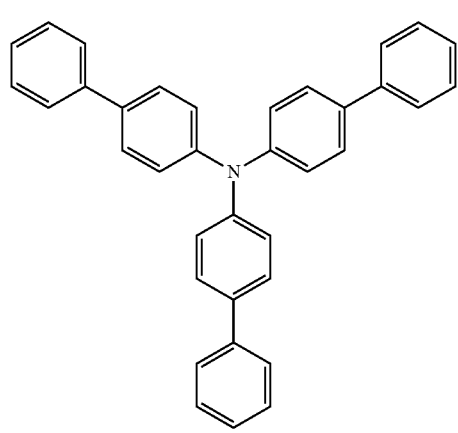

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device in an aspect of the invention may have a layer comprising an acceptor material which is disposed in contact with the anode side of each of the hole transporting layer and the first hole transporting layer. With such a layer, it is expected that the driving voltage is lowered and the production cost is reduced.

The acceptor material is preferably a compound represented by formula (K):

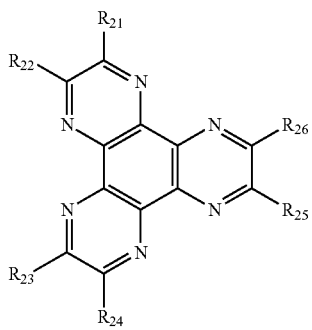

(K)

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer. The material for organic EL device in an aspect of the invention may be used as the material for the space layer.

Blocking Layer

The organic EL device in an aspect of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device in an aspect of the invention may be used as the material for the hole blocking layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device in an aspect of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The organic electroluminescence device in an aspect of the invention is usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described below in more detail with reference to the following examples. However, it should be noted that the scope of the invention is not limited thereto.

Synthesis Example 1 (Synthesis of Intermediate A)

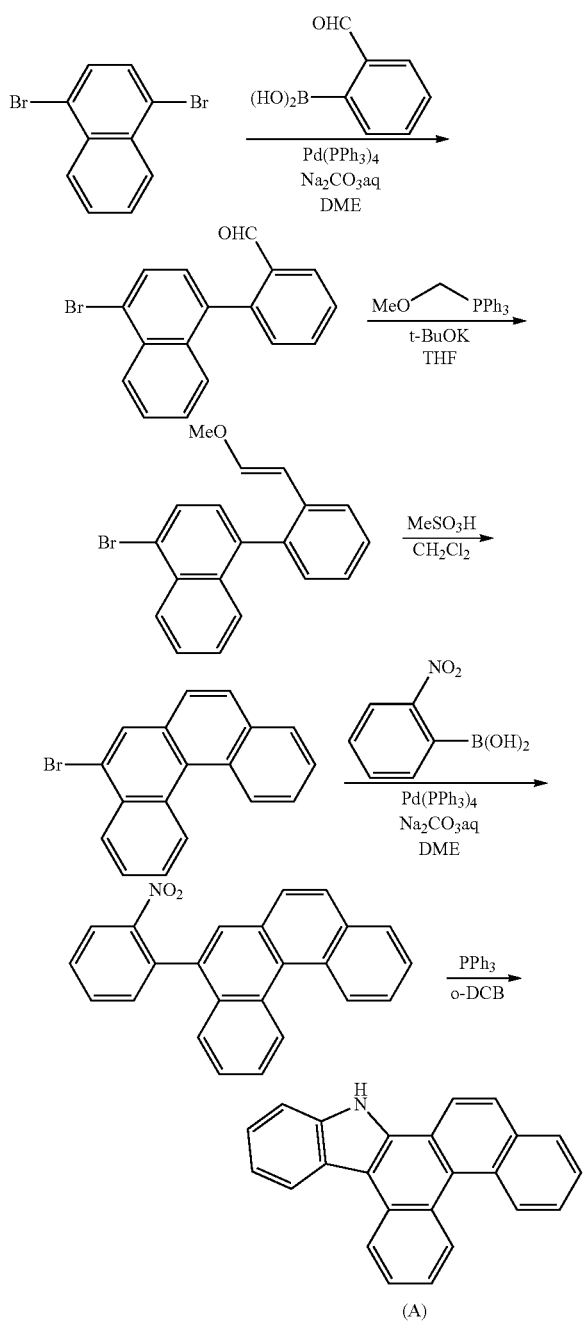

(1) Synthesis of 1-bromo-4-(2-formylphenyl)naphthalene

Under an argon atmosphere, 230 g of 1,4-dibromonaphthalene, 121 g of 2-formylphenyl boronic acid, and 18.5 g of tetrakis(triphenylphosphine) palladium(0) were charged in a flask. After adding 2.4 L of dimethoxyfuran (DME) and 1.2 L of a 2 M aqueous solution of sodium carbonate, the resultant mixture was refluxed for 8 h under heating and stirring. After cooling to room temperature (25° C.), the aqueous layer was removed. The organic layer was washed with water and then with a saturated saline and dried over magnesium sulfate. After removing magnesium sulfate by filtration, the organic layer was concentrated. The residue was purified by silica gel column chromatography to obtain 170 g of the target 1-bromo-4-(2-formylphenyl)naphthalene (yield: 67%).

(2) Synthesis of 1-bromo-4-[1-(2-methoxyvinyl)phenyl]naphthalene

Under an argon atmosphere, 170 g of 1-bromo-4-(2-formylphenyl)naphthalene, 207 g of methoxymethyltriphenylphosphonium chloride and 2.0 L of tetrahydrofuran (THF) were charged in a flask. After adding 73.6 g of potassium t-butoxide at room temperature (25° C.), the mixture was stirred at room temperature (25° C.) for 2 h and then 1.5 L of water was added. The reaction solution was extracted with diethyl ether and then the aqueous layer was removed. The organic layer was washed with water and then with a saturated saline and dried over magnesium sulfate. After removing magnesium sulfate by filtration, the organic layer was concentrated. The residue was purified by silica gel column chromatography to obtain 180 g of the target 1-bromo-4-[1-(2-methoxyvinyl)phenyl]naphthalene (yield: 99%).

(3) Synthesis of 5-bromobenzo[c]phenanthrene

Into a mixture of 180 g of 1-bromo-4-[1-(2-methoxyvinyl)phenyl]naphthalene and 1.0 L of dichloromethane, 25 mL of methanesulfonic acid was added at room temperature (25° C.) under stirring. The stirring was continued at room temperature (25° C.) for 8 h. After the reaction, 1 L of a 10% aqueous solution of potassium carbonate was added. The aqueous layer was removed, and the organic layer was washed with water and then a saturated saline and dried over magnesium sulfate. After removing magnesium sulfate by filtration, the organic layer was concentrated. The residue was purified by silica gel column chromatography to obtain 24.4 g of the target 5-bromobenzo[c]phenanthrene (yield: 15%).

(4) Synthesis of 5-(2-nitrophenyl)benzo[c]phenanthrene

Under an argon atmosphere, 2.00 g of 2-nitrophenyl boronic acid, 6.12 g of 5-bromobenzo[c]phenanthrene, 0.462 g of tetrakisphenylphosphine palladium(0), 80 mL of DME, and 40 mL of a 2 M aqueous solution of sodium carbonate were charged in a flask, and the resultant mixture was refluxed for 24 h under heating and stirring. After cooling to room temperature (25° C.), the reaction solution was extracted with toluene. After removing the aqueous layer, the organic layer was washed with a saturated saline, dried over magnesium sulfate, and concentrated. The residue was purified by silica gel column chromatography to obtain 5.72 g of 5-(2-nitrophenyl)benzo[c]phenanthrene.

(5) Synthesis of Intermediate A

Under an argon atmosphere, a mixture of 5.72 g of 5-(2-nitrophenyl)benzo[c]phenanthrene, 10.7 g of triphenylphosphine, and 200 mL of o-dichlorobenzene was refluxed for 48 h under heating and stirring. After cooling to room temperature (25° C.), 1 L of hexane was added. The precipitated crystal was collected by filtration. The obtained solid was recrystallized from toluene to obtain 3.20 g of the intermediate A.

Synthesis Example 2 (Synthesis of Intermediate B)

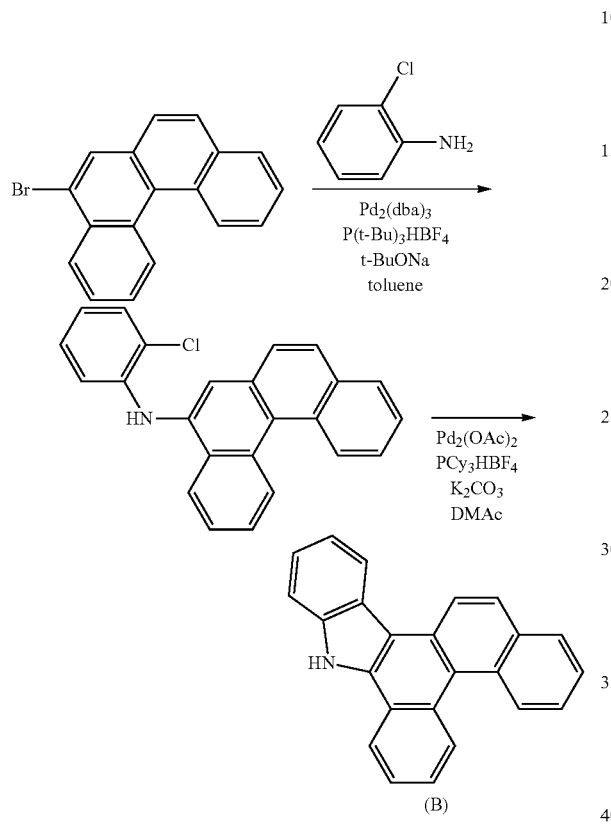

(1) Synthesis of 5-(2-chloroanilino)benzo[c]phenanthrene

Under an argon atmosphere, 12.3 g of 3-bromofluoranthene, 5.60 g of 2-chloroaniline, 0.732 g of trisdibenzylideneacetone dipalladium(0), 0.926 g of tri-t-butylphosphine tetrafluorohydroborate, 7.68 g of sodium t-butoxide, and 400 mL of dehydrated toluene were charged in a flask, and the resultant mixture was stirred at 80° C. for 8 h under stirring. After cooling to room temperature (25° C.), the reaction solution was extracted with toluene and filtered through celite. The filtrate was concentrated and then the residue was purified by silica gel column chromatography to obtain 11.32 g of 5-(2-chloroanilino)benzo[c]phenanthrene.

(2) Synthesis of Intermediate B

Under an argon atmosphere, 11.32 g of 5-(2-chloroanilino)benzo[c]phenanthrene, 0.22 g of palladium acetate, 8.84 g of potassium carbonate, 0.70 g of tricyclohexylphosphine tetrafluorohydroborate, and 80 mL N,N-dimethylacetamide were charged in a flask, and the resultant mixture was stirred at 140° C. for 24 h under heating. After cooling to room temperature (25° C.), the reaction solution was extracted with toluene and the insolubles were removed by filtration. The filtrate was concentrated and the residue was purified by silica gel column chromatography to obtain 4.20 g of the intermediate B.

Example 1 (Synthesis of Compound 1)

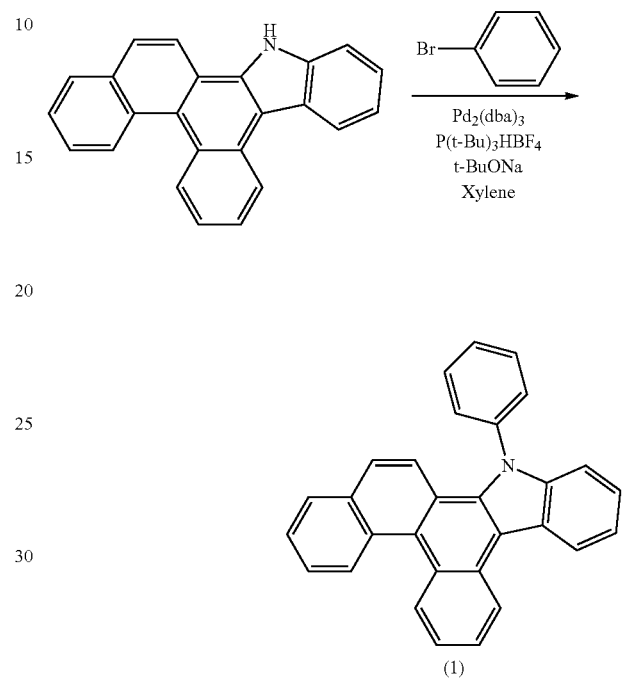

Under an argon stream, 1.57 g of bromobenzene, 3.80 g of the intermediate A, 0.183 g of tris(dibenzylideneacetone) dipalladium, 0.15 g of tri-t-butylphosphonium tetrafluoroborate, 1.9 g of sodium t-butoxide, and 50 mL of dehydrated xylene were successively added, and the resultant mixture was refluxed for 8 h under heating. After cooling the reaction solution to room temperature (25° C.), the organic layer was separated and the organic solvent was evaporated off under reduced pressure. The residue was purified by silica gel column chromatography to obtain 3.2 g of a compound, which was identified as the target compound 1 by mass spectrometric analysis which showed m/e=393 to the molecular weight of 393.15.

Example 2 (Synthesis of Compound 2)

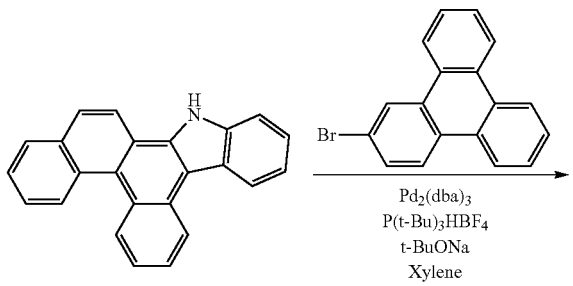

-continued

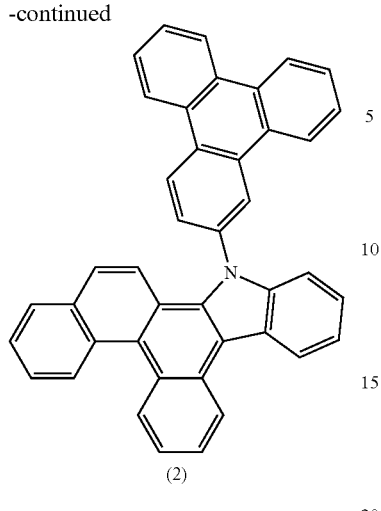
(2)

A compound was synthesized in the same manner as in Synthesis of Compound 1 except for using 2-bromotriphenylene in place of bromobenzene.

The obtained compound was identified as the target compound 2 by mass spectrometric analysis which showed m/e=543 to the molecular weight of 543.20.

Example 3 (Synthesis of Compound 3)

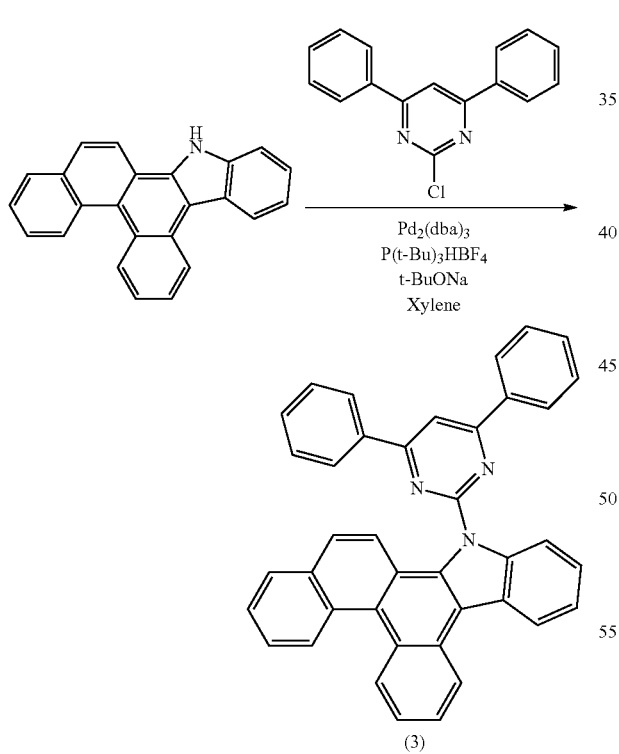
(3)

A compound was synthesized in the same manner as in Synthesis of Compound 1 except for using 2-chloro-4,6-diphenylpyrimidine in place of bromobenzene. The obtained compound was identified as the target compound 3 by mass spectrometric analysis which showed m/e=547 to the molecular weight of 547.20.

Example 4 (Synthesis of Compound 4)

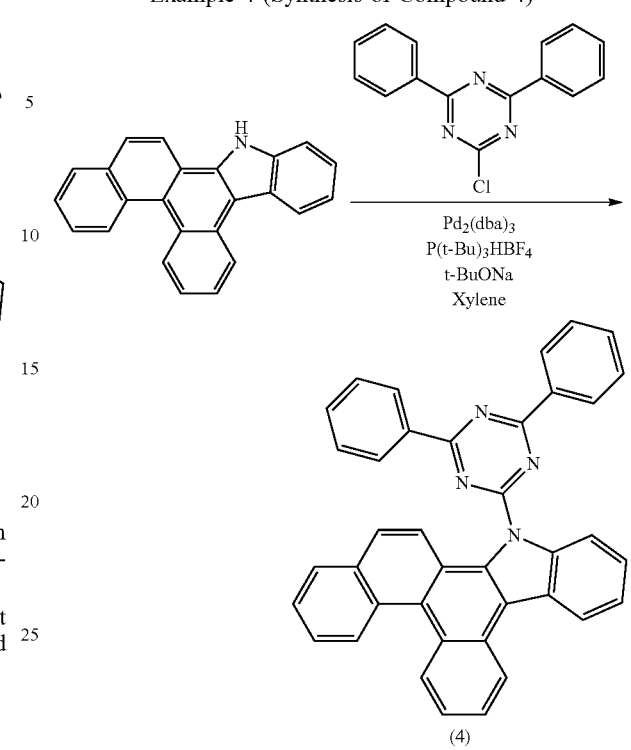
(4)

A compound was synthesized in the same manner as in Synthesis of Compound 1 except for using 2-chloro-4,6-diphenyltriazine in place of bromobenzene. The obtained compound was identified as the target compound 4 by mass spectrometric analysis which showed m/e=548 to the molecular weight of 548.20.

Example 5 (Synthesis of Compound 5)

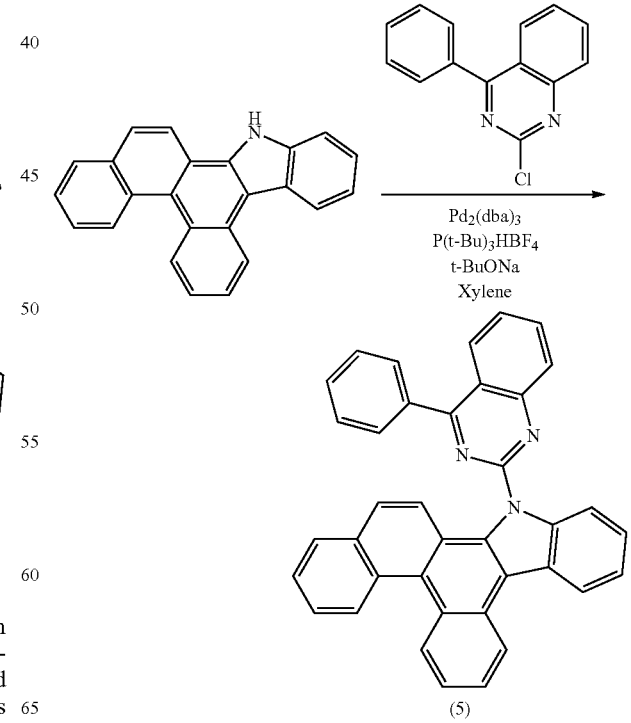
(5)

A compound was synthesized in the same manner as in Synthesis of Compound 1 except for using 2-chloro-4-phenylquinazoline which was synthesized by a known method in place of bromobenzene. The obtained compound was identified as the target compound 5 by mass spectrometric analysis which showed m/e=521 to the molecular weight of 521.61.

Example 6 (Synthesis of Compound 6)

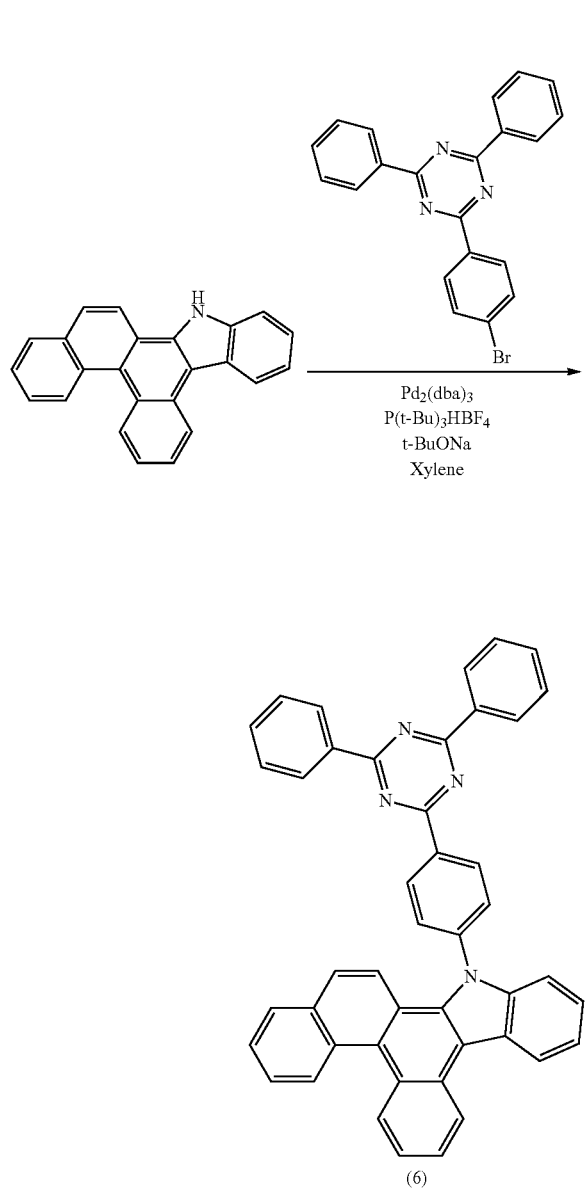

(6)

A compound was synthesized in the same manner as in Synthesis of Compound 1 except for using 2-(4-bromophenyl)-4,6-diphenyltriazine in place of bromobenzene. The obtained compound was identified as the target compound 6 by mass spectrometric analysis which showed m/e=624 to the molecular weight of 624.23.

Example 7 (Synthesis of Compound 7)

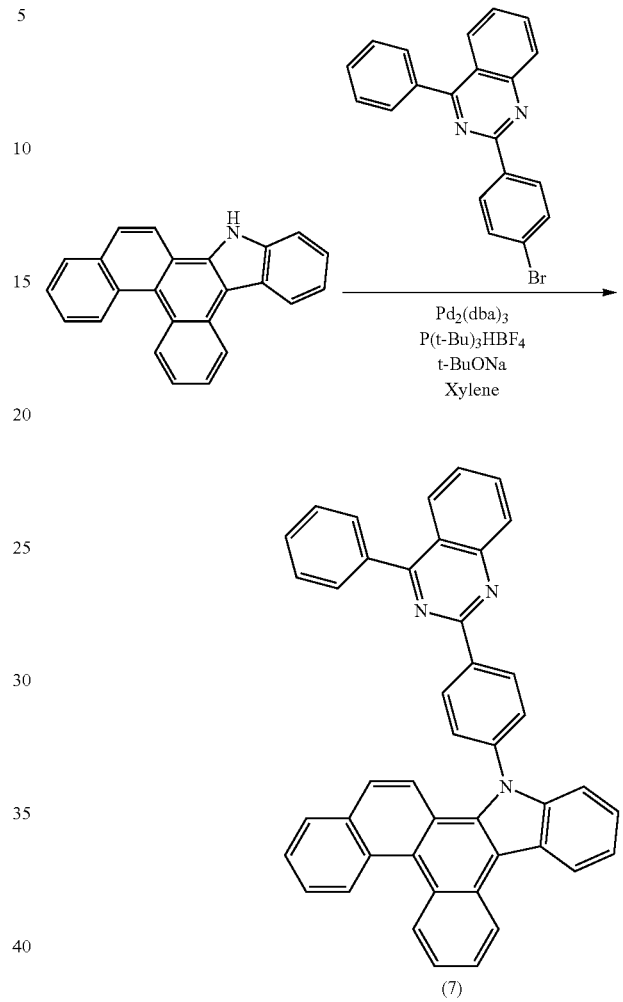

(7)

A compound was synthesized in the same manner as in Synthesis of Compound 1 except for using 2-(4-bromophenyl)-4-phenylquinazoline which was synthesized by a known method in place of bromobenzene. The obtained compound was identified as the target compound 7 by mass spectrometric analysis which showed m/e=597 to the molecular weight of 597.22.

Example 8 (Synthesis of Compound 8)

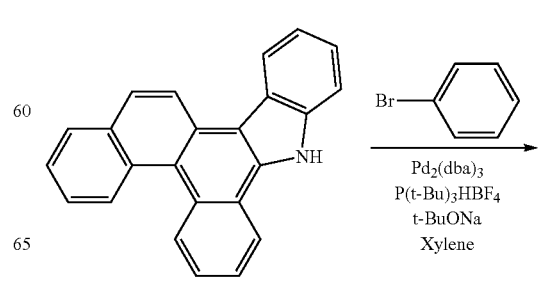

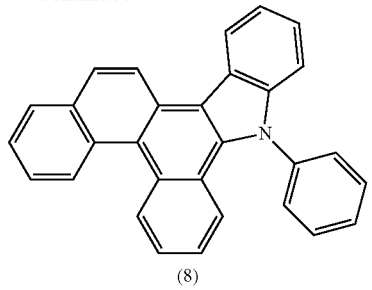

(8)

A compound was synthesized in the same manner as in Synthesis of Compound 1 except for using the intermediate B in place of the intermediate A. The obtained compound was identified as the target compound 8 by mass spectrometric analysis which showed m/e=393 to the molecular weight of 393.15.

Example 9 (Synthesis of Compound 9)

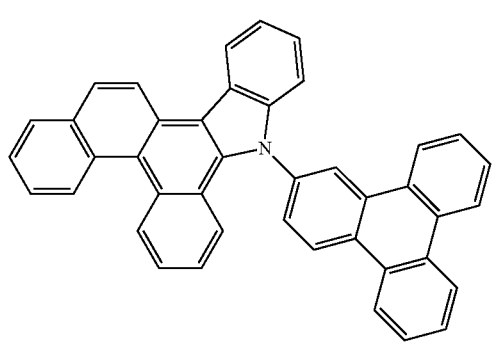

(9)

A compound was synthesized in the same manner as in Synthesis of Compound 1 except for using the intermediate B in place of the intermediate A and using 2-bromotriphenylene in place of bromobenzene. The obtained compound was identified as the target compound 9 by mass spectrometric analysis which showed m/e=543 to the molecular weight of 543.20.

Example 10 (Synthesis of Compound 10)

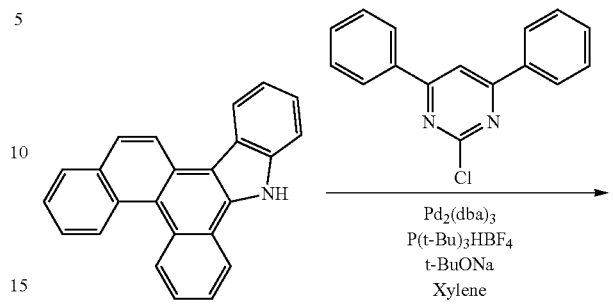

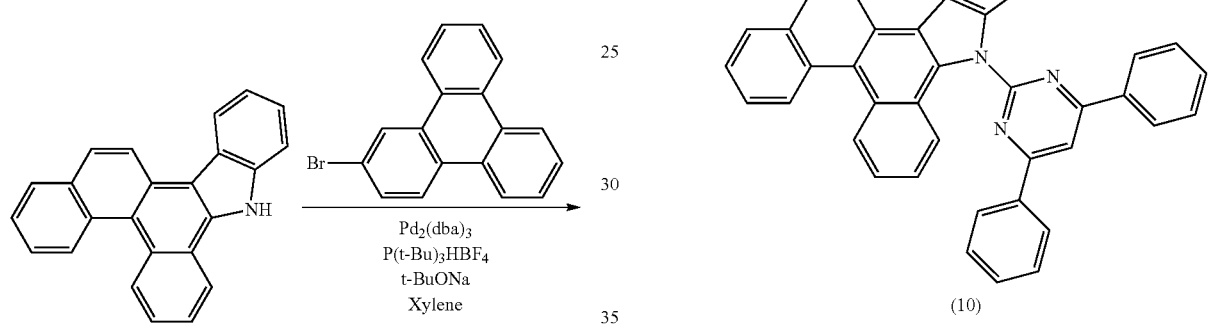

(10)

A compound was synthesized in the same manner as in Synthesis of Compound 1 except for using the intermediate B in place of the intermediate A and using 2-chloro-4,6-diphenylpyridine in place of bromobenzene. The obtained compound was identified as the target compound 10 by mass spectrometric analysis which showed m/e=547 to the molecular weight of 547.20.

Example 11 (Synthesis of Compound 11)

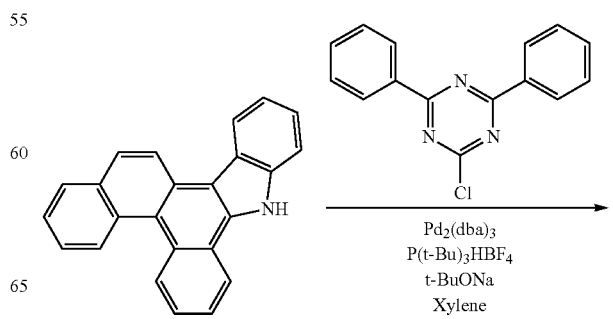

-continued

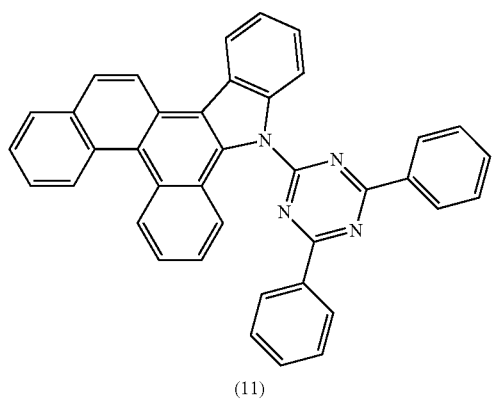

(11)

A compound was synthesized in the same manner as in Synthesis of Compound 1 except for using the intermediate B in place of the intermediate A and using 2-chloro-4,6-diphenyltriazine in place of bromobenzene. The obtained compound was identified as the target compound 11 by mass spectrometric analysis which showed m/e=548 to the molecular weight of 548.20.

Example 12 (Synthesis of Compound 12)

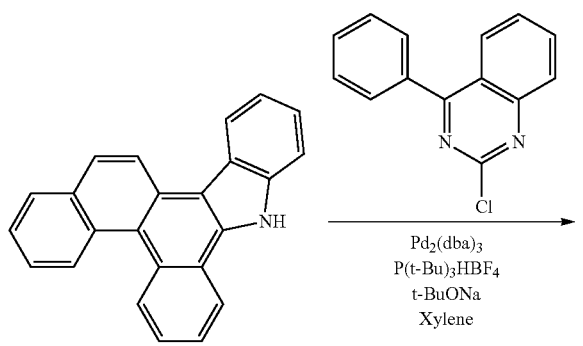

(12)

A compound was synthesized in the same manner as in Synthesis of Compound 1 except for using the intermediate B in place of the intermediate A and using 2-chloro-4-phenylquinazoline which was synthesized by a known method in place of bromobenzene. The obtained compound was identified as the target compound 12 by mass spectrometric analysis which showed m/e=521 to the molecular weight of 521.19.

Example 13 (Synthesis of Compound 13)

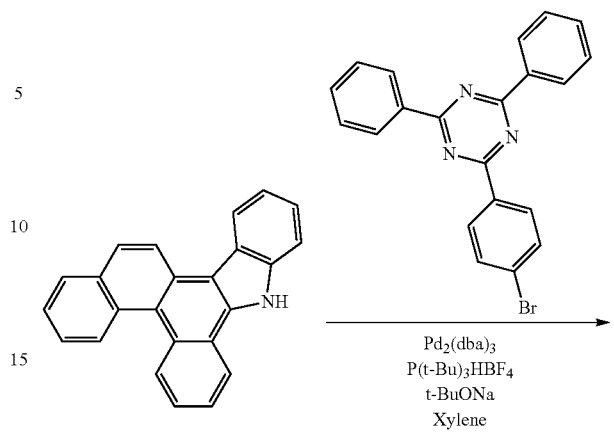

(13)

A compound was synthesized in the same manner as in Synthesis of compound 1 except for using the intermediate B in place of the intermediate A and using 2-(4-bromophenyl)-4,6-diphenyltriazine which was synthesized by a known method in place of bromobenzene. The obtained compound was identified as the target compound 13 by mass spectrometric analysis which showed m/e=624 to the molecular weight of 624.23.

Example 14 (Synthesis of Compound 14)

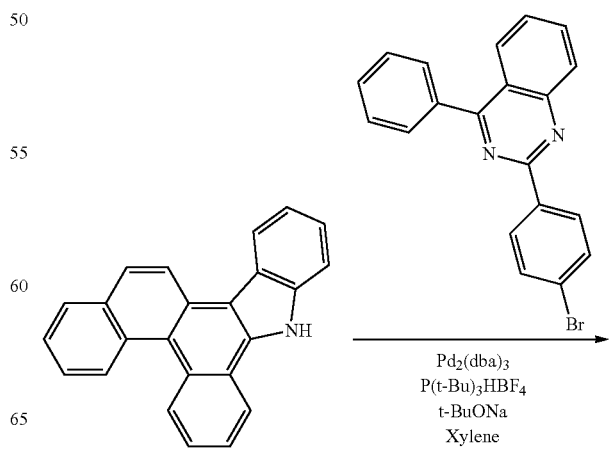

-continued

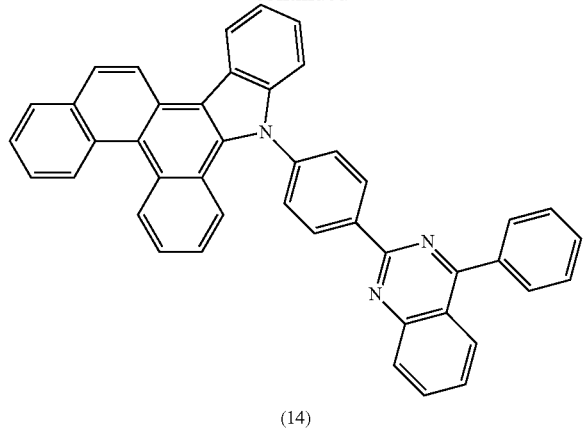

(14)

A compound was synthesized in the same manner as in Synthesis of Compound 1 except for using the intermediate B in place of the intermediate A and using 2-(4-bromophenyl)-4-phenylquinazoline which was synthesized by a known method in place of bromobenzene. The obtained compound was identified as the target compound 14 by mass spectrometric analysis which showed m/e=597 to the molecular weight of 597.22.

Other compounds within the scope of the present invention can be similarly synthesized according to the reactions mentioned above, while using a different reaction known in the art and starting materials corresponding to the target compound.

Example 15 (Production of Organic EL Device)

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate having a transparent electrode line with a thickness of 130 nm was mounted to a substrate holder of a vacuum vapor deposition apparatus. The following compound HT-1 as a first hole transporting material was vapor-deposited so as to cover the transparent electrode to form a first hole transporting layer with a thickness of 45 nm. Successively after forming the first hole transporting layer, the following compound HT-2 as a second hole transporting material was vapor-deposited to form a second hole transporting layer with a thickness of 10 nm.

On the second hole transporting layer, the compound 11 (host material) obtained in Example 11 and the following compound RD-1 (phosphorescent material) were vapor co-deposited to form a phosphorescent light emitting layer with a thickness of 40 nm. The concentration of the compound RD-1 in the light emitting layer was 5.0% by mass. The co-deposited film works as a light emitting layer.

Successively after forming the light emitting layer, the following compound ET-1 was vapor-deposited into a film with a thickness of 40 nm. The film of the compound ET-1 works as a first electron transporting layer.

Then, LiF was vapor-deposited into a film with a thickness of 1 nm at a film-forming speed of 0.01 nm/sec to form an electron injecting electrode (cathode). On the LiF film, metallic Al was vapor-deposited to form a metallic cathode with a thickness of 80 nm, thereby obtaining an organic EL device.

The compounds used in the examples and comparative example are shown below.

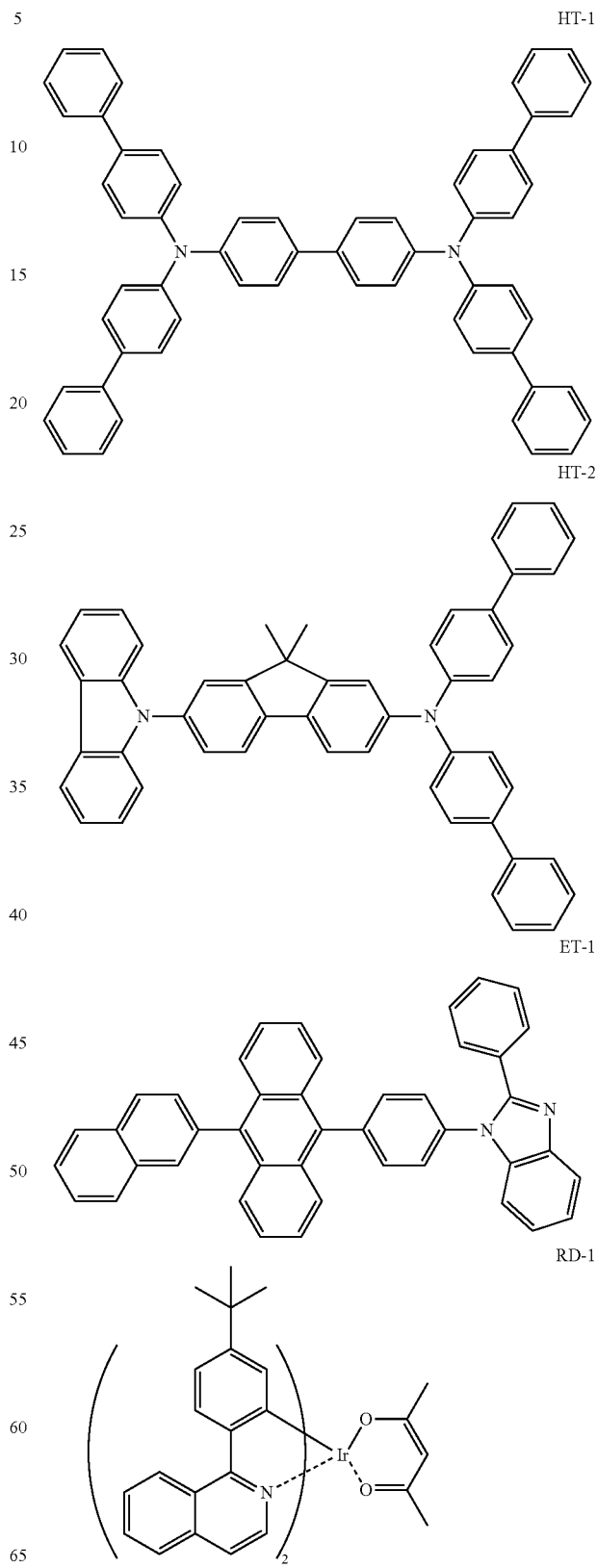

The organic EL device thus obtained was evaluated for the emission performance in the following manner.

Evaluation of Emission Performance of Organic EL Device

By driving the obtained organic EL device at room temperature by a constant direct current (current density: 10 mA/cm$^2$), the external quantum efficiency was measured using a spectroradiometer (CS-1000 manufactured by Minolta). The results are shown in Table 1.

Examples 16 to 22

Each device was produced in the same manner as in Example 15 except for using each compound shown in Table 1 in place of the compound 11 as a host material for the phosphorescent emitting layer. The evaluation of the emission performance was conducted in the same manner as in Example 15. The results are shown in Table 1.

Comparative Example 1

A device was produced in the same manner as in Example 15 except for using the comparative compound 1 shown below in place of the compound 11 as a host material for the phosphorescent emitting layer. The evaluation of the emission performance was conducted in the same manner as in Example 15. The results are shown in Table 1.

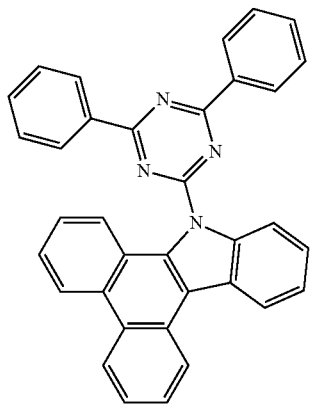

Comparative compound 1

TABLE 1

|  | Light emitting layer host material | Voltage (V) | External quantum efficiency (%) |
| --- | --- | --- | --- |
| Example 15 | compound 11 | 3.31 | 16.2 |
| Example 16 | compound 4 | 3.26 | 15.5 |
| Example 17 | compound 5 | 3.35 | 16.6 |
| Example 18 | compound 6 | 3.22 | 15.3 |
| Example 19 | compound 7 | 3.19 | 15.1 |
| Example 20 | compound 12 | 3.39 | 16.8 |
| Example 21 | compound 13 | 3.28 | 15.8 |
| Example 22 | compound 14 | 3.27 | 15.6 |
| Comparative Example 1 | comparative compound 1 | 3.50 | 13.1 |

Upon comparing Examples 15 to 22 with Comparative Example 1, it can be seen that the organic EL devices employing the nitrogen-containing heterocyclic derivative in an aspect of the invention are excellent in the emission efficiency as compared with the organic EL device of Comparative Example 1.

REFERENCE NUMERALS

1: Organic electroluminescence device
2: Substrate
3: Anode
4: Cathode
5: Light emitting layer
6: Anode-side organic thin film layer
7: Cathode-side organic thin film layer
10: Emission unit

What is claimed is:

1. A nitrogen-containing heterocyclic derivative represented by formula (6) or (7):

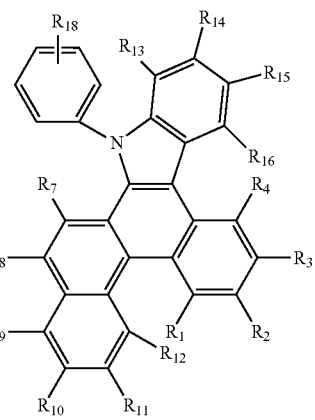

(6)

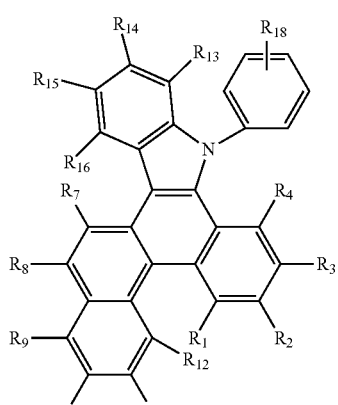

(7)

wherein $R_1$ to $R_4$ and $R_7$ to $R_{12}$ each represent a hydrogen atom; each of $R_{13}$ to $R_{16}$ independently represents a hydrogen atom or a substituent group, wherein the substituent group represented by $R_{13}$ to $R_{16}$ is independently selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a monoor disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group; $R_{18}$ represents a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{13}$ to $R_{16}$ and $R_{18}$ may be bonded to each other to form a saturated or unsaturated divalent group which completes a ring, with the proviso that the following compound is excluded from the nitrogen-containing heterocyclic derivative:

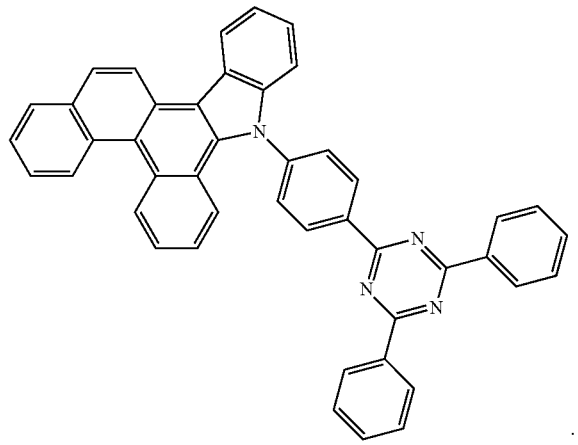 [SMILES: c1ccc(-c2nc(-c3ccccc3)nc(-c3ccc(-n4c5ccccc5c5c6ccc7ccccc7c6c6ccccc6c54)cc3)n2)cc1]

2. The nitrogen-containing heterocyclic derivative according to claim 1, wherein the nitrogen-containing heterocyclic derivative is represented by formula (10) or (11):

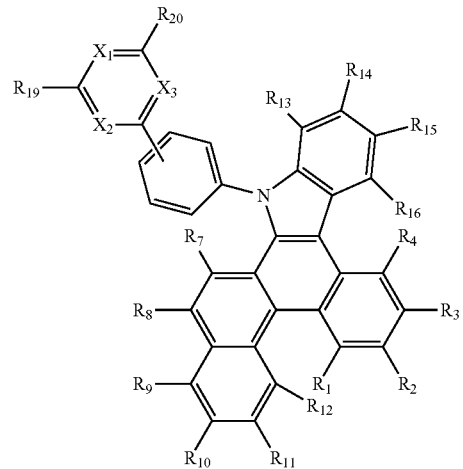

(10)

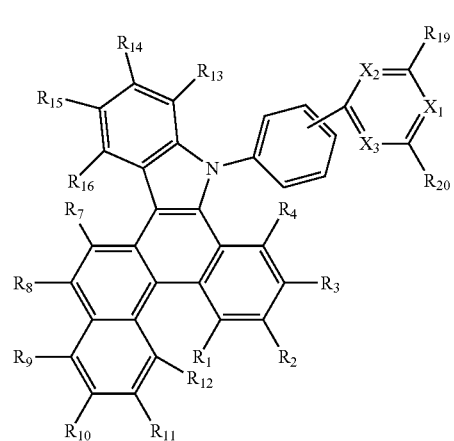

(11)

wherein each of $X_1$ to $X_3$ independently represents $C(R_{21})$ or a nitrogen atom; $R_1$ to $R_4$ and $R_7$ to $R_{16}$ are as defined in formula (6) and formula (7); a pair of adjacent two groups selected from $R_{13}$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ to $R_{21}$ may be bonded to each other to form a saturated or unsaturated divalent group which completes a ring.

3. The nitrogen-containing heterocyclic derivative according to claim 2, wherein the nitrogen-containing heterocyclic derivative is represented by formula (12) or (13):

(12)

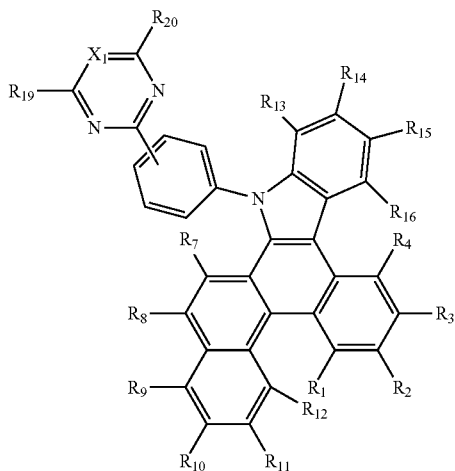

(13)

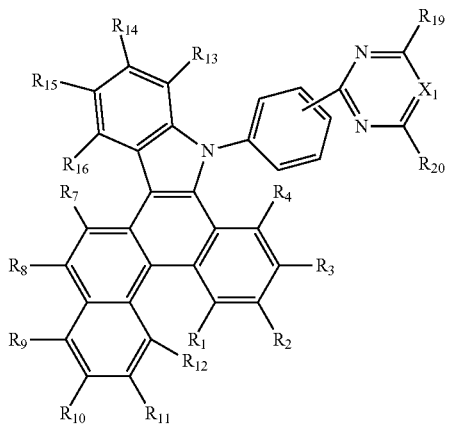

wherein $X_1$, $R_1$ to $R_4$, $R_7$ to $R_{16}$, $R_{19}$, and $R_{20}$ are each as defined in formula (10) and formula (11).

4. A nitrogen-containing heterocyclic derivative represented by formula (14) or (15):

(14)

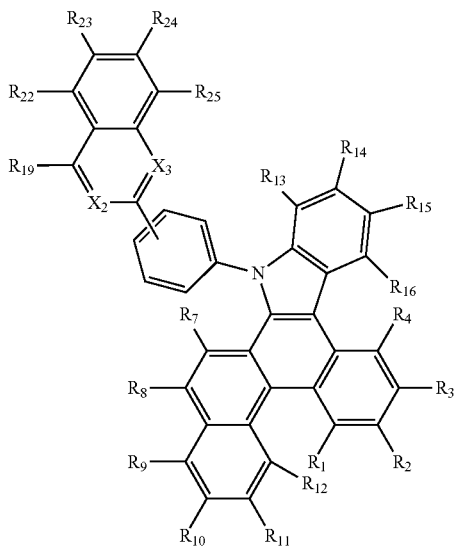

(15)

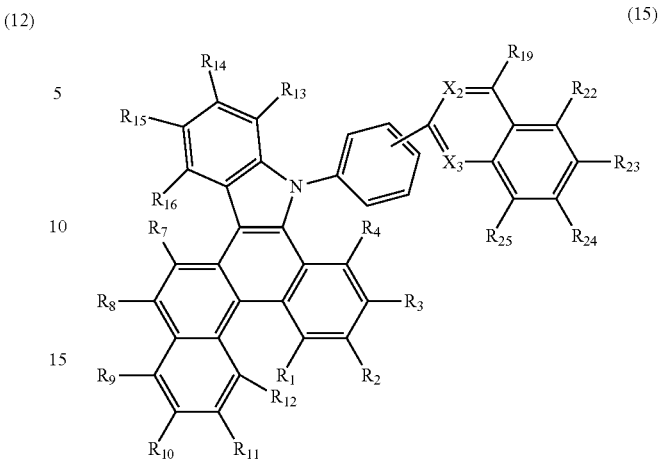

wherein:
each of $X_2$ to $X_3$ independently represents $C(R_{21})$ or a nitrogen atom;
each of $R_1$ to $R_4$ and $R_7$ to $R_{16}$ independently represents a hydrogen atom or a substituent group;
the substituent group represented by $R_1$ to $R_4$ and $R_7$ to $R_{16}$ is independently selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group;

a pair of adjacent two groups selected from $R_1$ to $R_4$ and $R_7$ to $R_{12}$ is not bonded to each other to form a ring structure;

a pair of adjacent two groups selected from $R_{13}$ to $R_{16}$ may be bonded to each other to form a saturated or unsaturated divalent group which completes a ring;

each of $R_{19}$, $R_{21}$ to $R_{25}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ and $R_{21}$ to $R_{25}$ may be bonded to each other to form a saturated or unsaturated divalent group which completes a ring.

5. A nitrogen-containing heterocyclic derivative represented by formula (16) or (17):

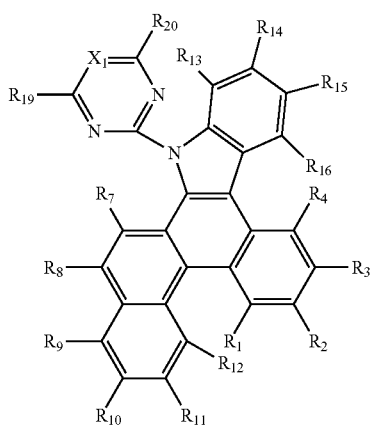

(16)

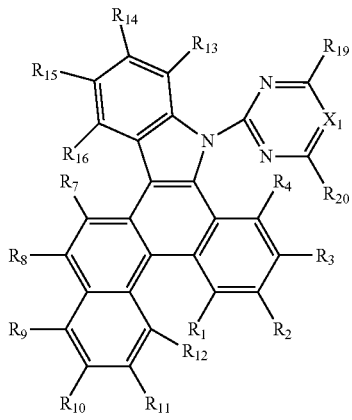

(17)

wherein $X_1$ represents $C(R_{21})$ or a nitrogen atom; $R_1$ to $R_4$ and $R_7$ to $R_{12}$ each represent a hydrogen atom; each of $R_{13}$ to $R_{16}$ independently represents a hydrogen atom or a substituent group, wherein the substituent group represented by $R_{13}$ to $R_{16}$ is independently selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group; a pair of adjacent two groups selected from $R_{13}$ to $R_{16}$ may be bonded to each other to form a saturated or unsaturated divalent group which completes a ring; each of $R_{19}$ to $R_{21}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ to $R_{21}$ may be bonded to each other to form a saturated or unsaturated divalent group which completes a ring.

6. A nitrogen-containing heterocyclic derivative represented by formula (18) or (19):

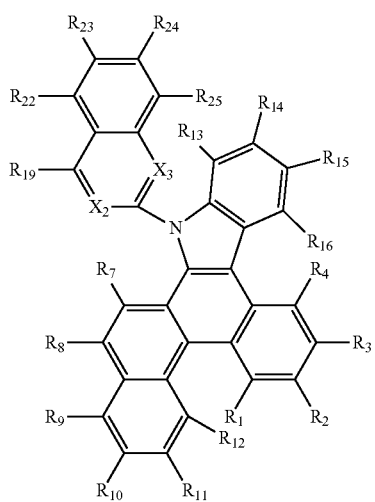

(18)

-continued

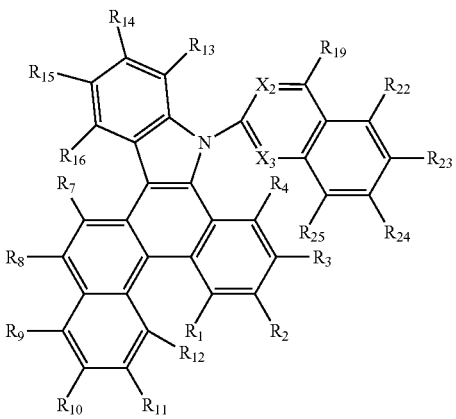

(19)

wherein each of $X_2$ to $X_3$ independently represents $C(R_{21})$ or a nitrogen atom; $R_1$ to $R_4$ and $R_7$ to $R_{12}$ each represent a hydrogen atom; each of $R_{13}$ to $R_{16}$ independently represents a hydrogen atom or a substituent group, wherein the substituent group represented by $R_{13}$ to $R_{16}$ is independently selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group; $R_{18}$ represents a substituted or unsubstituted aryl group having 6 to 30 ring carbon atoms or a substituted or unsubstituted nitrogen-containing heterocyclic group having 5 to 30 ring atoms; a pair of adjacent two groups selected from $R_{13}$ to $R_{16}$ may be bonded to each other to form a saturated or unsaturated divalent group which completes a ring; each of $R_{19}$ and $R_{21}$ to $R_{25}$ independently represents a hydrogen atom, a substituted or unsubstituted aryl group having 6 to 30 ring carbon atoms or a substituted or unsubstituted nitrogen-containing heterocyclic group having 5 to 30 ring atoms; and a pair of adjacent two groups selected from $R_{19}$ and $R_{21}$ to $R_{25}$ may be bonded to each other to form a saturated or unsaturated divalent group which completes a ring, with the proviso that the following compound is excluded from the nitrogen-containing heterocyclic derivative:

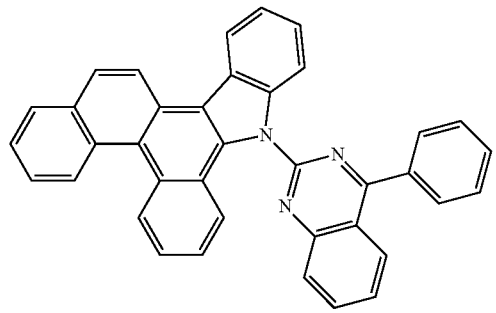

7. A material for organic electroluminescence devices which comprises the nitrogen-containing heterocyclic derivative according to claim 1.

8. An organic electroluminescence device which comprises an organic thin film layer between a cathode and an anode, wherein the organic thin film layer comprises one or more layers and comprises a light emitting layer, and at least one layer of the organic thin film layer comprises the nitrogen-containing heterocyclic derivative according to claim 1.

9. The organic electroluminescence device according to claim 8, wherein the light emitting layer comprises the nitrogen-containing heterocyclic derivative.

10. The organic electroluminescence device according to claim 8, wherein the organic electroluminescence device further comprises an anode-side organic thin film layer between the anode and the light emitting layer, and the anode-side organic thin film layer comprises the nitrogen-containing heterocyclic derivative.

11. The organic electroluminescence device according to claim 8, wherein the organic electroluminescence device further comprises a cathode-side organic thin film layer between the cathode and the light emitting layer, and the cathode-side organic thin film layer comprises the nitrogen-containing heterocyclic derivative.

12. The organic electroluminescence device according to claim 8, wherein the light emitting layer comprises a phosphorescent material.

13. The organic electroluminescence device according to claim 8, wherein the light emitting layer comprises a fluorescent material.

14. The organic electroluminescence device according to claim 12, wherein the phosphorescent material is an ortho-metallated complex comprising a metal atom selected from iridium (Ir), osmium (Os) and platinum (Pt).

15. The organic electroluminescence device according to claim 14, wherein the phosphorescent material is a complex represented by formula (X) or (Y):

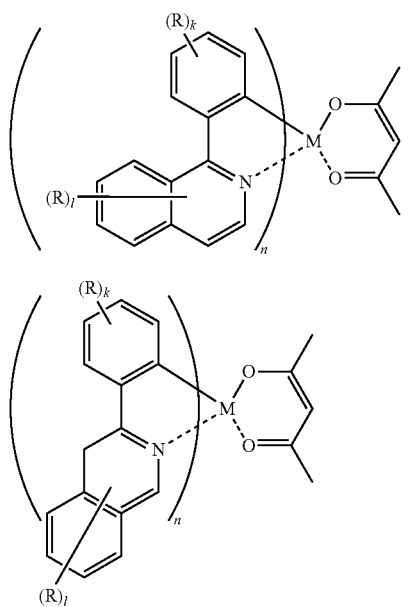

(X)

(Y)

wherein R independently represents a hydrogen atom or a substituent group, k represents an integer of 1 to 4, l represents an integer of 1 to 6, n represents an integer of 2 to 4, and M represents Ir, Os, or Pt.

16. An electronic equipment which comprises the organic electroluminescence device according to claim 8.

17. A nitrogen-containing heterocyclic derivative represented by formula (1):

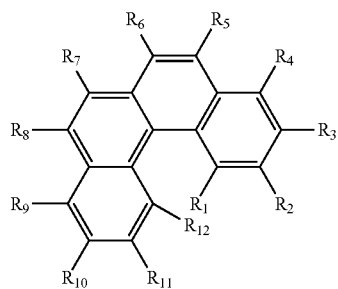

(1)

wherein each of $R_1$ to $R_{12}$ independently represents a hydrogen atom or a substituent group, one pair of adjacent two groups selected from $R_1$ to $R_{12}$ are bonded to each other to form a ring structure represented by formula (a), at least one of $R_1$ to $R_{12}$ other than the one pair of adjacent two groups represents the substituent group, and a pair of adjacent two groups selected from $R_1$ to $R_{12}$ other than the one pair of the adjacent two groups is not bonded to form a ring structure:

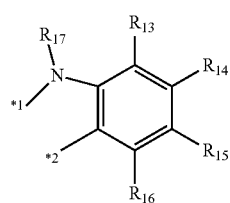

(a)

wherein each of $R_{13}$ to $R_{17}$ independently represents a hydrogen atom or a substituent group, a pair of adjacent two groups selected from $R_{13}$ to $R_{17}$ may be bonded to each other to form a saturated or unsaturated divalent group which completes a ring, and *1 and *2 are bonded to carbon atoms to which the at least one pair of the adjacent two groups selected from $R_1$ to $R_{12}$ are bonded;

wherein the substituent group represented by $R_1$ to $R_{17}$ is independently selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group.

18. The nitrogen-containing heterocyclic derivative according to claim 1, wherein a pair of adjacent two groups selected from $R_{13}$ to $R_{16}$ and $R_{18}$ is not bonded to each other to form a saturated or unsaturated divalent group which completes a ring.

19. A nitrogen-containing heterocyclic derivative represented by formula (2) or (3):

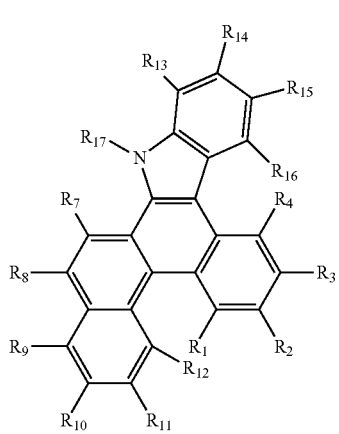

(2)

-continued (3)

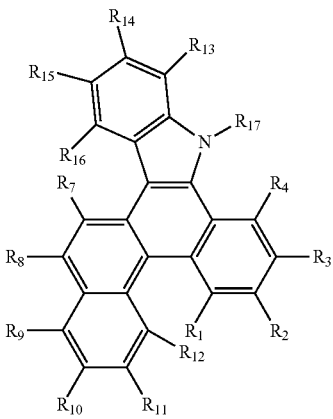

wherein $R_1$ to $R_4$ and $R_7$ to $R_{12}$ represent a hydrogen atom; each of $R_{13}$ to $R_{16}$ independently represents a hydrogen atom or a substituent group, wherein the substituent group represented by $R_{13}$ to $R_{16}$ is selected from the group consisting of a substituted or unsubstituted alkyl group having 1 to 50 carbon atoms, a substituted or unsubstituted cycloalkyl group having 3 to 50 ring carbon atoms, a substituted or unsubstituted aryl group having 6 to 60 ring carbon atoms, a substituted or unsubstituted aralkyl group having 7 to 61 carbon atoms, an amino group, a mono- or disubstituted amino group having a substituent selected from a substituted or unsubstituted alkyl group having 1 to 50 carbon atoms and a substituted or unsubstituted aryl group having 6 to 60 ring carbon atoms, a substituted or unsubstituted alkoxy group having 1 to 50 carbon atoms, a substituted or unsubstituted aryloxy group having 6 to 60 ring carbon atoms, a mono-, di-, or trisubstituted silyl group having a substituent selected from a substituted or unsubstituted alkyl group having 1 to 50 carbon atoms and a substituted or unsubstituted aryl group having 6 to 60 ring carbon atoms, a substituted or unsubstituted heteroaryl group having 5 to 60 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 60 ring carbon atoms, a disubstituted phosphoryl group having a substituent selected from a substituted or unsubstituted alkyl group having 1 to 50 carbon atoms and a substituted or unsubstituted aryl group having 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl- or aryl-substituted carbonyl group, a carboxyl group, a vinyl group, a (meth)acryloyl group, an epoxy group, and an oxetanyl group; a pair of adjacent two groups selected from $R_{13}$ to $R_{16}$ may be bonded to each other to form a saturated or unsaturated divalent group which completes a ring; and $R_{17}$ represents a substituted or unsubstituted aryl group having 6 to 30 ring carbon atoms, with the proviso that the following compound is excluded from the nitrogen-containing heterocyclic derivative:

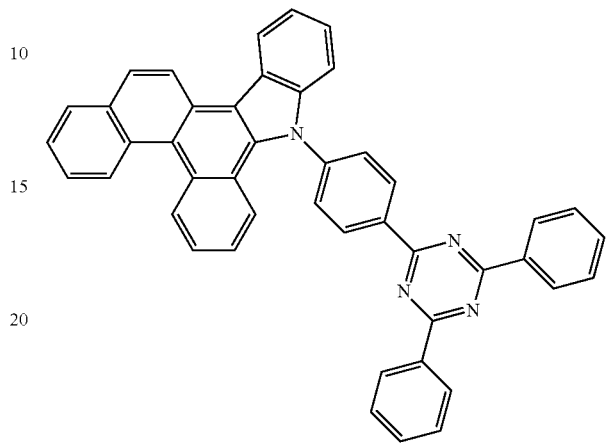

20. The nitrogen-containing heterocyclic derivative according to claim 19, wherein the substituted or unsubstituted aryl group having 6 to 30 ring carbon atoms represented by $R^{17}$ is selected from the group consisting of a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, and a dibenzanthryl group.

21. The nitrogen-containing heterocyclic derivative according to claim 20, wherein the substituted or unsubstituted aryl group having 6 to 30 ring carbon atoms represented by $R^{17}$ is selected from the group consisting of a naphthyl group, a naphthylphenyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, and a dibenzanthryl group.

* * * * *